US012582451B2

(12) United States Patent (10) Patent No.: US 12,582,451 B2

Palmer et al. (45) Date of Patent: Mar. 24, 2026

(54) ACTIVE COMPRESSION DEVICES, METHODS OF ASSEMBLY AND METHODS OF USE

(71) Applicant: Conventus Orthopaedics, Inc., Horsham, PA (US)

(72) Inventors: Andrew K. Palmer, Plymouth, MN (US); William Ogilvie, Plymouth, MN (US)

(73) Assignee: Conventus Orthopaedics, Inc., Horsham, PA (US)

( * ) Notice: Subject to any disclaimer, the term of this patent is extended or adjusted under 35 U.S.C. 154(b) by 595 days.

(21) Appl. No.: 17/651,227

(22) Filed: Feb. 15, 2022

(65) Prior Publication Data

US 2022/0168032 A1 Jun. 2, 2022

Related U.S. Application Data

(63) Continuation of application No. 16/599,077, filed on Oct. 10, 2019, now Pat. No. 11,278,333, which is a
(Continued)

(51) Int. Cl.
*A61B 17/72* (2006.01)
*A61B 17/80* (2006.01)
(Continued)

(52) U.S. Cl.
CPC ...... *A61B 17/7225* (2013.01); *A61B 17/7216* (2013.01); *A61B 17/8004* (2013.01);
(Continued)

(58) Field of Classification Search
CPC .......................... A61B 17/7216; A61B 17/7225
See application file for complete search history.

(56) References Cited

U.S. PATENT DOCUMENTS 972,787 A 10/1910 Huyck
2,382,019 A 8/1945 Miller
(Continued)

FOREIGN PATENT DOCUMENTS

AU 648723 B 10/1992
CN 103099667 A 3/2013
(Continued)

OTHER PUBLICATIONS

WIPO, U.S. International Search Authority, International Search Report and Written Opinion mailed Jun. 9, 2017 in International Patent Application No. PCT/US2017/019530, 9 pages.
(Continued)

*Primary Examiner* — Julianna N Harvey

(74) *Attorney, Agent, or Firm* — Husch Blackwell LLP; Andrew C. Landsman; Beatrice Kealy

(57) ABSTRACT

Active compression devices, methods of assembly and methods of use are disclosed. A bone fixation device may include a first member, a second member shaped to engage the first member, and at least one deformable member. A bone fusion device including a female member with a proximal and distal end, a male member with a proximal and distal end, and at least one elastic element positioned between the female member and the male member. A bone plating device including a first member, a second member shaped to engage the first member, and at least one deformable member positioned between the first member and the second member. Methods of assembling and using the bone fixation devices, bone fusion devices, and bone plating devices are also disclosed.

20 Claims, 36 Drawing Sheets

Related U.S. Application Data continuation of application No. 15/532,484, filed as application No. PCT/US2015/063472 on Dec. 2, 2015, now Pat. No. 10,478,238.

(60) Provisional application No. 62/086,311, filed on Dec. 2, 2014.

(51) Int. Cl.

| | |
|---|---|
| *A61B 17/00* | (2006.01) |
| *A61B 17/68* | (2006.01) |
| *A61B 17/70* | (2006.01) |
| *A61B 17/86* | (2006.01) |
| *A61B 90/00* | (2016.01) |

(52) U.S. Cl.
CPC .................... *A61B 17/8023* (2013.01); *A61B 2017/00862* (2013.01); *A61B 2017/681* (2013.01); *A61B 17/7014* (2013.01); *A61B 17/7019* (2013.01); *A61B 17/7025* (2013.01); *A61B 17/7059* (2013.01); *A61B 17/863* (2013.01); *A61B 17/864* (2013.01); *A61B 2090/034* (2016.02)

(56) References Cited

U.S. PATENT DOCUMENTS

| | | | |
|---|---|---|---|
| 2,397,545 | A | 4/1946 | Hardinge |
| 2,414,882 | A | 1/1947 | Longfellow |
| 2,526,959 | A | 10/1950 | Lorenzo |
| 2,563,976 | A | 8/1951 | Torosian |
| 2,612,159 | A | 9/1952 | Collison |
| 2,621,653 | A | 12/1952 | Briggs |
| 2,699,774 | A | 1/1955 | Livingston |
| 2,801,631 | A | 8/1957 | Charnley |
| 2,952,254 | A | 9/1960 | Keating |
| 2,985,168 | A | 5/1961 | Jonas et al. |
| 3,051,169 | A | 8/1962 | Grath |
| 3,076,453 | A | 2/1963 | Tronzo |
| 3,435,526 | A | 4/1969 | Brancato |
| 3,441,017 | A | 4/1969 | Kaessmann |
| 3,678,925 | A | 7/1972 | Fischer |
| 3,716,051 | A | 2/1973 | Fischer |
| 3,760,802 | A | 9/1973 | Fischer et al. |
| 3,915,162 | A | 10/1975 | Miller |
| 3,990,438 | A | 11/1976 | Pritchard |
| 4,095,591 | A | 6/1978 | Graham, Jr. et al. |
| 4,175,555 | A | 11/1979 | Herbert |
| 4,463,753 | A | 8/1984 | Gustilo |
| 4,621,629 | A | 11/1986 | Koeneman |
| 4,653,486 | A | 3/1987 | Coker |
| 4,711,232 | A | 12/1987 | Fischer et al. |
| 4,799,841 | A | 1/1989 | Ramsbro |
| 4,858,601 | A | 8/1989 | Glisson |
| 4,940,467 | A | 7/1990 | Tronzo |
| RE33,348 | E | 9/1990 | Lower |
| 4,959,064 | A * | 9/1990 | Engelhardt ............. B23P 13/00 |
| | | | 606/65 |
| 5,019,079 | A | 5/1991 | Ross |
| 5,041,116 | A | 8/1991 | Wilson |
| 5,098,434 | A | 3/1992 | Serbousek |
| 5,100,405 | A | 3/1992 | McClaren |
| 5,209,753 | A | 5/1993 | Biedermann et al. |
| 5,334,204 | A | 8/1994 | Clewett et al. |
| 5,397,328 | A | 3/1995 | Behrens et al. |
| 5,593,410 | A | 1/1997 | Vrespa |
| 5,919,193 | A | 7/1999 | Slavitt |
| 5,944,302 | A | 8/1999 | Loc et al. |
| 6,001,101 | A | 12/1999 | Augagneur et al. |
| 6,048,344 | A | 4/2000 | Schenk et al. |
| 6,053,922 | A | 4/2000 | Krause et al. |
| 6,258,093 | B1 | 7/2001 | Edwards et al. |
| 6,319,254 | B1 | 11/2001 | Giet et al. |
| 6,447,518 | B1 | 9/2002 | Krause et al. |
| 6,458,134 | B1 | 10/2002 | Songer et al. |
| 6,656,184 | B1 | 12/2003 | White et al. |
| 6,743,233 | B1 | 6/2004 | Baldwin et al. |
| 6,949,101 | B2 | 9/2005 | McCleary et al. |
| 6,955,513 | B2 | 10/2005 | Niku |
| 7,063,706 | B2 | 6/2006 | Wittenstein |
| 7,122,037 | B2 | 10/2006 | Happonen |
| 7,135,023 | B2 | 11/2006 | Watkins et al. |
| 7,175,626 | B2 | 2/2007 | Neff |
| 7,329,258 | B2 | 2/2008 | Studer |
| 7,569,055 | B2 | 8/2009 | Zander et al. |
| 7,578,836 | B2 | 8/2009 | Justin et al. |
| 7,582,107 | B2 | 9/2009 | Trail et al. |
| 7,608,097 | B2 | 10/2009 | Kyle |
| 7,611,521 | B2 | 11/2009 | Lubbers et al. |
| 7,686,807 | B2 | 3/2010 | Padget |
| 7,833,256 | B2 | 11/2010 | Biederman et al. |
| 7,951,198 | B2 | 5/2011 | Sucec et al. |
| 8,029,524 | B1 | 10/2011 | Mitusina |
| 8,043,333 | B2 | 10/2011 | Frigg et al. |
| 8,048,134 | B2 | 11/2011 | Partin |
| 8,052,706 | B2 | 11/2011 | Mitusina |
| 8,057,500 | B2 | 11/2011 | Mitusina |
| 8,118,952 | B2 | 2/2012 | Gall et al. |
| 8,142,464 | B2 | 3/2012 | Mitusina |
| 8,298,273 | B2 | 10/2012 | Pathak |
| 8,308,783 | B2 | 11/2012 | Morris et al. |
| 8,323,272 | B2 | 12/2012 | Rusly |
| 8,343,197 | B2 | 1/2013 | Gonzalez-Hernandez |
| 8,366,559 | B2 | 2/2013 | Papenfuss et al. |
| 8,394,127 | B2 | 3/2013 | Winslow et al. |
| 8,398,690 | B2 | 3/2013 | Bottlang et al. |
| 8,414,585 | B2 | 4/2013 | Meneghini et al. |
| 8,518,044 | B2 | 8/2013 | Sidebotham et al. |
| 8,529,611 | B2 | 9/2013 | Champagne et al. |
| 8,591,579 | B2 | 11/2013 | Pellegrino et al. |
| 8,685,067 | B2 | 4/2014 | King et al. |
| 8,715,326 | B2 | 5/2014 | Champagne et al. |
| 8,845,649 | B2 | 9/2014 | Jackson |
| 8,852,239 | B2 | 10/2014 | Jackson et al. |
| 8,956,356 | B2 | 2/2015 | Zurschmiede |
| 8,968,415 | B2 | 3/2015 | Meridew et al. |
| 8,998,925 | B2 | 4/2015 | Schwappach |
| 9,078,716 | B2 | 7/2015 | Pech |
| 9,161,793 | B2 | 10/2015 | Huebner |
| 9,168,076 | B2 | 10/2015 | Patty et al. |
| 9,173,693 | B2 | 11/2015 | McDaniel et al. |
| 9,204,886 | B2 | 12/2015 | May et al. |
| 9,204,910 | B2 | 12/2015 | Epperly |
| 9,283,006 | B2 | 3/2016 | Fonte |
| 9,314,286 | B2 | 4/2016 | Bottlang et al. |
| 9,345,520 | B2 | 5/2016 | Biedermann et al. |
| 9,381,052 | B2 | 7/2016 | Ziran |
| 9,408,648 | B2 | 8/2016 | Culbert |
| 9,421,051 | B2 | 8/2016 | Finley |
| 9,445,850 | B2 | 9/2016 | Kinmon |
| 9,456,857 | B2 | 10/2016 | Labitzke |
| 9,482,260 | B1 | 11/2016 | Krause |
| 9,492,202 | B2 | 11/2016 | Wilfried et al. |
| 9,526,542 | B2 | 12/2016 | Ehmke |
| 9,700,361 | B2 | 7/2017 | Bottlang et al. |
| 9,763,712 | B2 | 9/2017 | Appenzeller et al. |
| 9,788,868 | B2 | 10/2017 | Jackson |
| 9,801,663 | B2 | 10/2017 | Krause |
| 9,808,867 | B2 | 11/2017 | Krause et al. |
| 9,820,788 | B2 | 11/2017 | Vrionis et al. |
| 9,827,029 | B2 | 11/2017 | Hulliger |
| 9,848,930 | B2 | 12/2017 | Huebner et al. |
| 9,861,413 | B2 | 1/2018 | Palmer et al. |
| 9,980,762 | B2 | 5/2018 | Anapliotis |
| 2002/0055740 | A1 | 5/2002 | Lieberman |
| 2002/0095154 | A1 | 7/2002 | Atkinson et al. |
| 2005/0152770 | A1 | 7/2005 | Tschakaloff et al. |
| 2005/0165402 | A1 | 7/2005 | Taras |
| 2005/0197660 | A1 | 9/2005 | Haid et al. |
| 2005/0277940 | A1 * | 12/2005 | Neff .................. A61B 17/8875 |
| | | | 606/310 |
| 2006/0264954 | A1 | 11/2006 | Sweeney et al. |
| 2007/0016204 | A1 | 1/2007 | Martinez et al. |

(56)　　　　References Cited

U.S. PATENT DOCUMENTS

| | | |
|---|---|---|
| 2007/0270855 A1 * | 11/2007 | Partin ................. A61B 17/863 |
| | | 606/279 |
| 2007/0282342 A1 | 12/2007 | Niederberger et al. |
| 2008/0147127 A1 | 6/2008 | Tipirneni et al. |
| 2008/0177333 A1 | 7/2008 | Ferguson |
| 2008/0188854 A1 | 8/2008 | Moser |
| 2008/0236601 A1 | 10/2008 | Jacobus |
| 2008/0262497 A1 | 10/2008 | Nijenbanning et al. |
| 2009/0062868 A1 | 3/2009 | Casutt |
| 2009/0245089 A1 | 10/2009 | Kandukuri Narayan et al. |
| 2009/0254089 A1 | 10/2009 | Tipirneni et al. |
| 2009/0264937 A1 | 10/2009 | Parrott et al. |
| 2009/0275966 A1 | 11/2009 | Mitusina |
| 2010/0139182 A1 | 6/2010 | Wernersson et al. |
| 2010/0145499 A1 | 6/2010 | Sato et al. |
| 2010/0152786 A1 | 6/2010 | Behrbalk |
| 2010/0256690 A1 | 10/2010 | Appenzeller et al. |
| 2010/0318130 A1 | 12/2010 | Parlato et al. |
| 2011/0092992 A1 | 4/2011 | Darois et al. |
| 2012/0053639 A1 | 3/2012 | Grant |
| 2012/0245704 A1 | 9/2012 | Childs |
| 2013/0041469 A1 | 2/2013 | Phelps |
| 2013/0317503 A1 | 11/2013 | Songer et al. |
| 2014/0005669 A1 | 1/2014 | Graham |
| 2014/0050550 A1 | 2/2014 | Stempniewski et al. |
| 2014/0081338 A1 | 3/2014 | Biedermann et al. |
| 2015/0223843 A1 | 8/2015 | Tipirneni et al. |
| 2015/0230843 A1 | 8/2015 | Palmer et al. |
| 2015/0238232 A1 | 8/2015 | Biedermann et al. |
| 2015/0250507 A1 | 9/2015 | Harrison et al. |
| 2015/0250604 A1 | 9/2015 | Fonte |
| 2015/0305819 A1 | 10/2015 | Krause |
| 2015/0374387 A1 | 12/2015 | Courtney, Jr. et al. |
| 2016/0213368 A1 | 7/2016 | Stecco et al. |
| 2016/0310190 A1 | 10/2016 | Gonzalez Blohm et al. |
| 2017/0020585 A1 | 1/2017 | Harshman et al. |
| 2017/0100171 A1 | 4/2017 | Palmer et al. |
| 2017/0189085 A1 | 7/2017 | Krause |
| 2017/0202563 A1 | 7/2017 | Leroy et al. |
| 2017/0245905 A1 | 8/2017 | Reimels |
| 2017/0311984 A1 | 11/2017 | Stecco et al. |
| 2017/0360489 A1 | 12/2017 | Palmer et al. |
| 2022/0142691 A1 * | 5/2022 | Smith ................ A61B 17/8685 |

FOREIGN PATENT DOCUMENTS

| | | | |
|---|---|---|---|
| DE | 2906068 A1 | 6/1980 | |
| DE | 3936703 A1 | 5/1991 | |
| DE | 102013111354 A1 * | 4/2014 | ......... A61B 17/7216 |
| EP | 1967151 A1 | 9/2008 | |
| EP | 1430845 B1 | 7/2009 | |
| EP | 1753355 B1 | 11/2011 | |
| EP | 2626019 A1 | 8/2013 | |
| EP | 1937172 B1 | 3/2014 | |
| EP | 2858585 B1 | 5/2017 | |
| JP | 1995049082 A | 2/1995 | |
| JP | 2018502694 A | 2/2018 | |
| NL | 1030218 C2 | 4/2007 | |
| SU | 923533 A1 | 4/1982 | |
| SU | 1061807 A1 | 12/1983 | |
| WO | WO 91/009572 A1 | 7/1991 | |
| WO | WO97/03611 A1 | 2/1997 | |
| WO | WO 01/054598 A1 | 8/2001 | |
| WO | WO 03/047442 A1 | 6/2003 | |
| WO | WO 2010/017631 A1 | 2/2010 | |
| WO | WO 2012/154119 A1 | 11/2012 | |
| WO | WO2014/076157 A1 | 5/2014 | |
| WO | WO2015/168311 A1 | 11/2015 | |
| WO | WO 2016/081528 A1 | 5/2016 | |
| WO | WO 2017/117092 A1 | 7/2017 | |
| WO | WO 2017/147537 A1 | 8/2017 | |

OTHER PUBLICATIONS

WIPO, U.S. International Search Authority, International Search Report and Written Opinion mailed Mar. 3, 2016 in International Patent Application No. PCT/US2015/063472, 8 pages.

* cited by examiner

100

100

100

134

130

148

142   114   174   110

104   140   138   146   150   124   174   160   120   160   126   102   122   118   116   128   122   136

134

130

138   170   172   160   146   144   132

140   148   142   174   174   160   150   144   136

130

110

170

170

OBTAINING A BONE FIXATION DEVICE — 300

OBTAINING AN INSERTION TOOL — 310

INSERTING A PORTION OF THE FIRST MEMBER INTO THE INSERTION TOOL — 320

MOVING THE SECOND MEMBER AS THE INSERTION TOOL ENGAGES THE FIRST MEMBER — 330

INSERTING THE BONE FIXATION DEVICE INTO AT LEAST ONE BONE — 340

REMOVING THE INSERTION TOOL FROM THE BONE FIXATION DEVICE — 350

410

410

410

410

500

500

500

530

534

542

546

544

538

540

532

544

510

510

600

630

630

610

610

ACTIVE COMPRESSION DEVICES, METHODS OF ASSEMBLY AND METHODS OF USE

CROSS-REFERENCE TO RELATED APPLICATION

This application is a continuation of and claims priority to U.S. patent application Ser. No. 16/599,077 filed Oct. 10, 2019 entitled Active Compression Devices, Methods Of Assembly And Methods Of Use, which is a continuation of and claims priority to U.S. patent application Ser. No. 15/532,484 filed Jun. 1, 2017 entitled Active Compression Devices, Methods Of Assembly And Methods Of Use (now U.S. Pat. No. 10,478,238 issued Nov. 19, 2019), which is the U.S. National Phase of and claims priority to International Patent Application No. PCT/US2015/063472 filed Dec. 2, 2015 entitled Active Compression Devices, Methods Of Assembly And Methods Of Use, which claims benefit of and priority to U.S. Provisional Patent Application No. 62/086, 311 filed Dec. 2, 2014 entitled Active Compression Devices, Methods Of Assembly And Methods Of Us, all of which are incorporated herein by reference in their entireties.

TECHNICAL FIELD

The present invention relates generally to general surgery and orthopedic implants, and more specifically, but not exclusively, concerns devices implanted for bone fusion.

BACKGROUND OF THE INVENTION

Bone fractures and other bone damage are regularly treated by fusion. Bones are currently fused with the assistance of implants, such as, plates and screws which are designed to hold the bones or bone pieces in place while healing occurs and the bones or bone pieces are fused together. Improved devices and methods for fusing bones together are needed.

SUMMARY OF THE INVENTION

Advancement of the state of bone fusion and bone fixation devices and implants and the surgical management relating to the clinical presentation of damaged or fractured bones within the body is believed desirable. Several embodiments of the bone fixation devices or bone fusion devices used to treat patients suffering from either diseased or damaged bones includes a first member, a second member, at least three spring members, and a ring member.

The present invention provides in one aspect, a bone fixation device including a first member, a second member shaped to engage the first member, and at least one deformable member positioned between the first member and the second member.

The present invention provides in another aspect, a bone fixation device including a female member with a proximal end and a distal end, a male member with a proximal end and a distal end, and at least one elastic element positioned between the female member and the male member.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

DETAILED DESCRIPTION FOR CARRYING OUT THE INVENTION

Figure 1:
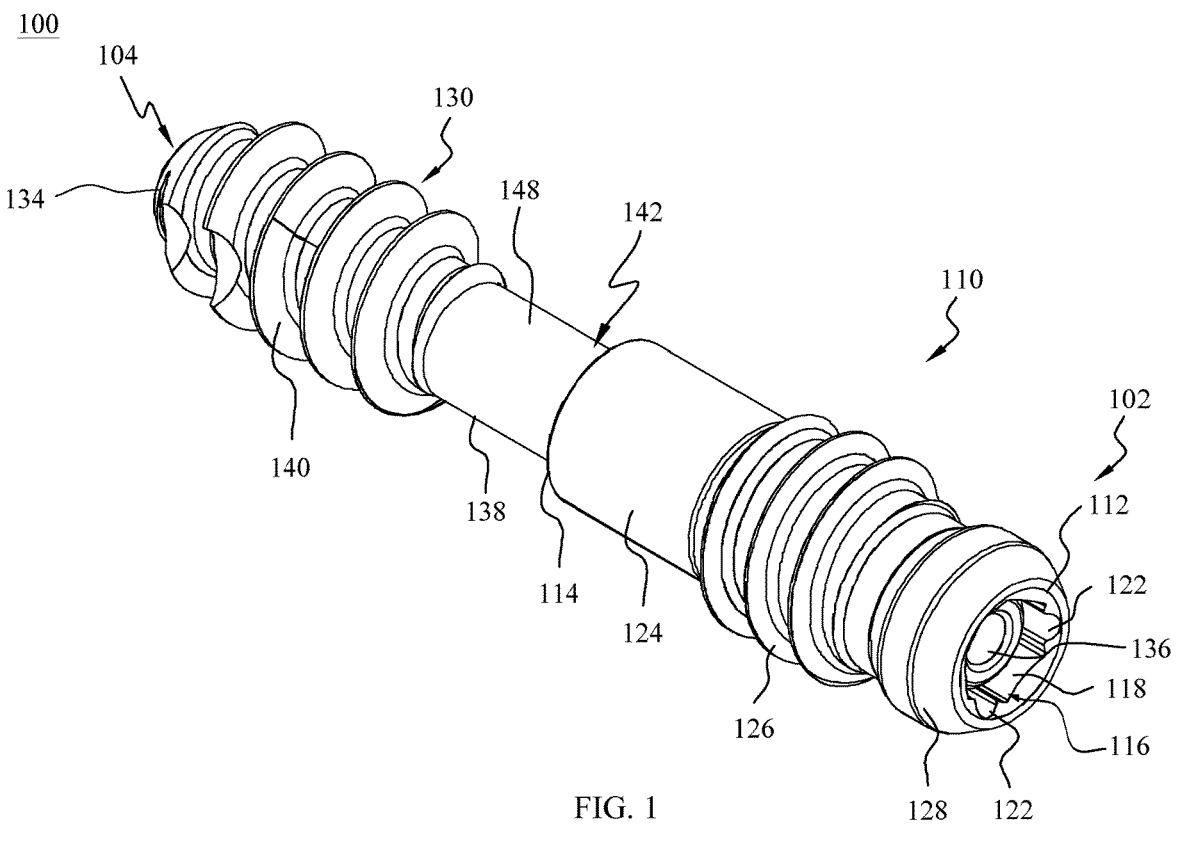
FIG. 1 is a perspective view of a bone fixation device from a first end, in accordance with an aspect of the present invention.
Figure 2:
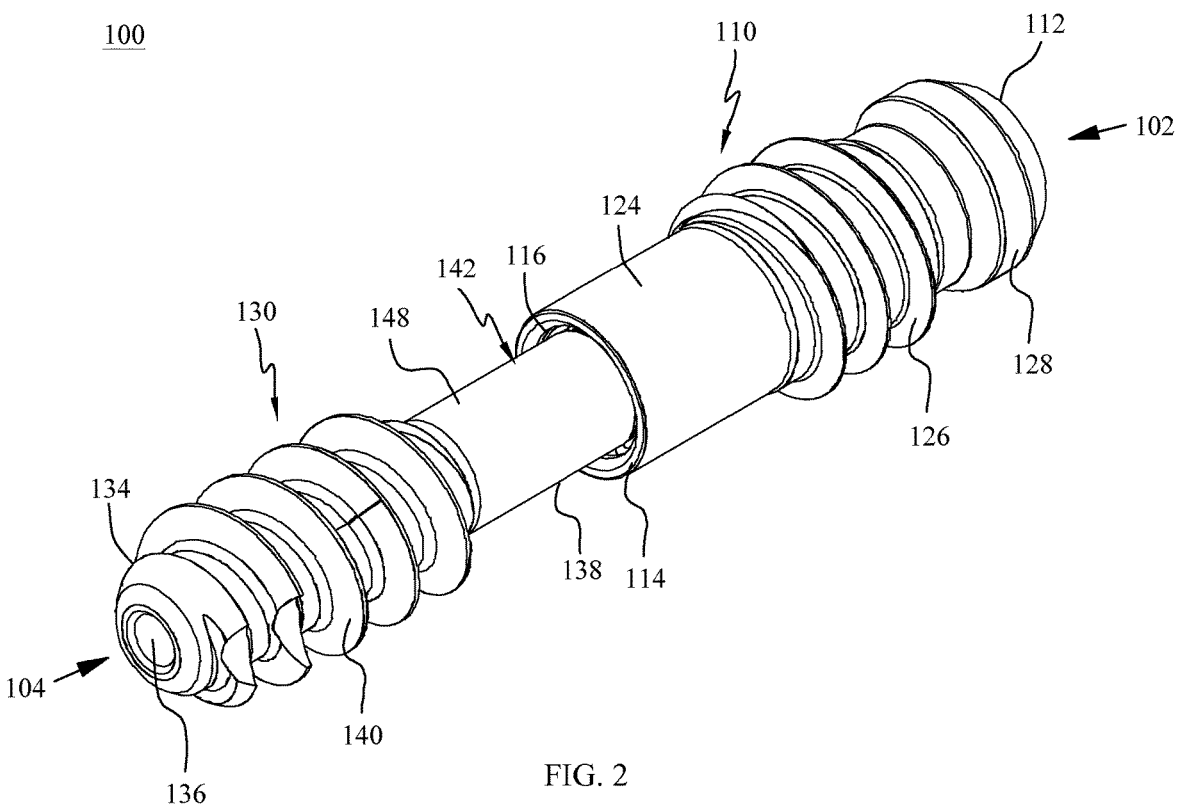
FIG. 2 is a perspective view of the bone fixation device of FIG. 1 from a second end, in accordance with an aspect of the present invention.
Figure 3:
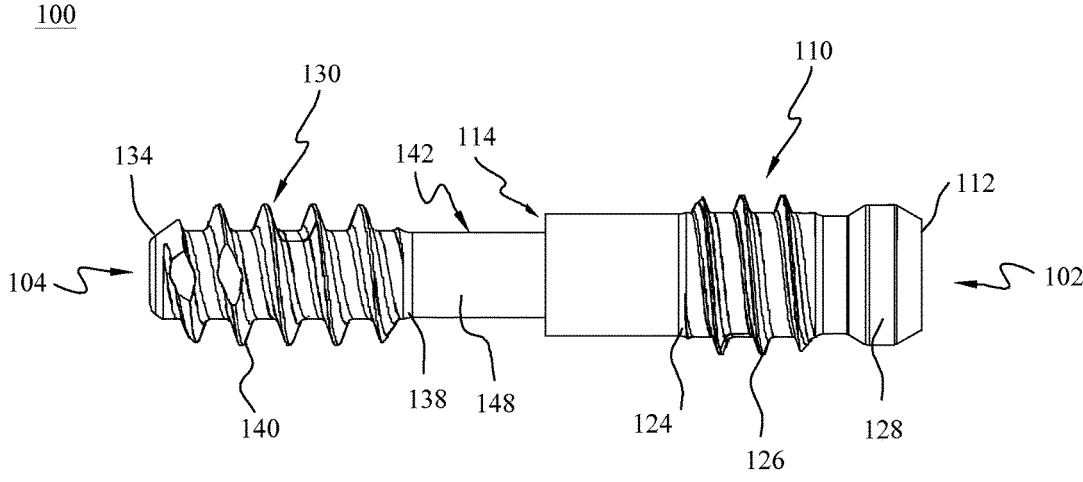
FIG. 3 is a side view of the bone fixation device of FIG. 1, in accordance with an aspect of the present invention.

Generally stated, disclosed herein is a bone fixation device that may include a first member, a second member, at least one spring member, and a ring member. As used herein, the terms "bone fixation device," "bone fusion device," "medical device," "device," and "implant" may be used interchangeable as they essentially describe the same device. Further, the corresponding insertion tool may also be referred to as "tool" or "instrument" and these terms may be used interchangeably. Further, described herein is a method of assembling the bone fixation device. Finally, described herein is a method of using the bone fixation device to compress two pieces of bone.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant farthest from the insertion end, while "distal" indicates the portion of the implant nearest the insertion end. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

As depicted in FIGS. 1-7 and 19, a bone fixation device or bone fusion device 100 includes a first member 110 and a second member 130. The bone fixation device 100 may also include at least one spring member 160 and a ring member 170. The second member 130 may be sized and shaped to fit into the first member 100 with, for example, the at least one spring member 160 and the ring member 170 positioned between the first member 110 and second member 130. The at least one spring member 160 may also be positioned, for example, inside an opening 136 of the second member 130. The first member 110 may be positioned, for example, at a proximal end 102 of the bone fixation device 100, while the second member 130 may be positioned, for example, at a distal end 104 of the bone fixation device 100. The bone fixation device 100 may be, for example, a screw, intramedullary rod, spinal rod, bone plate, and the like for joining together, compressing or pressing together at least two bones or pieces of bone or alternatively for expanding or distracting at least two bones or pieces of bone. Intramedullary rods may be used, for example, during the compression or expansion across long bone fractures, as described in greater detail below with reference to FIGS. 22-30. The spinal rods may be used, for example, during the compression or distraction of a segment of the spinal column for stabilization of a spine, as described in greater detail below with reference to FIGS. 31-39. In addition, bone plates may be used, for example, during the compression or expansion across bone fractures or spinal fusions, such as, cervical plating, as described in greater detail below with reference to FIGS. 40-48.

The first member 110, also shown in FIGS. 12-15, may be, for example, a female member. The first member 110 may include a first end 112 and a second end 114 opposite the first end 112. The terms "first end" and "proximal end" may be used interchangeably herein and the terms "second end" and "distal end" may be used interchangeably herein as they essentially refer to the same ends. The first member 110 may have an opening 116 extending from the first end 112 to the second end 114 along the longitudinal axis of the first member 110. The opening 116 may form an interior surface 118. The opening 116 of the first member 110 may also include a groove 120 positioned near the second end 114. The terms "groove," "slot" or "member groove" may be used interchangeably herein as they essentially refer to the same indentation. The groove 120 may be cut into the wall of the first member 110 and extend from the opening 116 into the first member 110 toward the exterior surface 124 of the first member 110. The interior surface 118 may be, for example, a relatively hexagonal or polygonal shape from the first end 112 to the groove 120. The opening 116 may also include at least one channel or slot 122 inset into the interior surface 118 and extending from the first end 112 toward the second end 114 and stopping when the channels 122 extend into the groove 120. The at least one channel 122 may receive the at least one spring member 160. The bone fixation device 100 may include, for example, at least three channels 122 and at least three spring members 160, as shown in FIGS. 4, 7, 12-14. The at least three channels 122 may be positioned radially around the opening 116 to provide circumferential forces to facilitate equal compressive loads. For example, where the interior surface 118 is relatively hexagonally shaped, the channels 122 may be positioned on every other portion of the interior surface 118, for example, on the first, third, and fifth surfaces and the second, fourth, and sixth surfaces may be generally planar. The shape of the interior surface may also be, for example, relatively octagonal or another polygonal shape with an even number of sides.

With continued reference to FIGS. 1-7, 12-15, and 19, the exterior surface 124 of the first member 110 may be, for example, generally cylindrical. The exterior surface 124 may include a threaded portion or threaded end 126 and a protrusion or extension 128. The protrusion 128 may extend away from the exterior surface 124 near the first end 112 to form an engagement portion for coupling to an insertion tool or resorbable member for insertion into a patient. The protrusion 128 may be configured, for example, as a tapered surface that extends down to the exterior surface 124 to form rounded edges on the protrusion 128. The threaded portion 126 may be positioned, for example, toward the middle of the bone fixation device 100 between the protrusion 128 and the second end 114 of the first member 110. The threaded portion 126 may extend only along a portion of the exterior surface 124 from the protrusion 128 to the second end 114 or alternatively, the threaded portion 126 may extend from the protrusion 128 to the second end 114 of the first member 110.

Figures 9, 10:
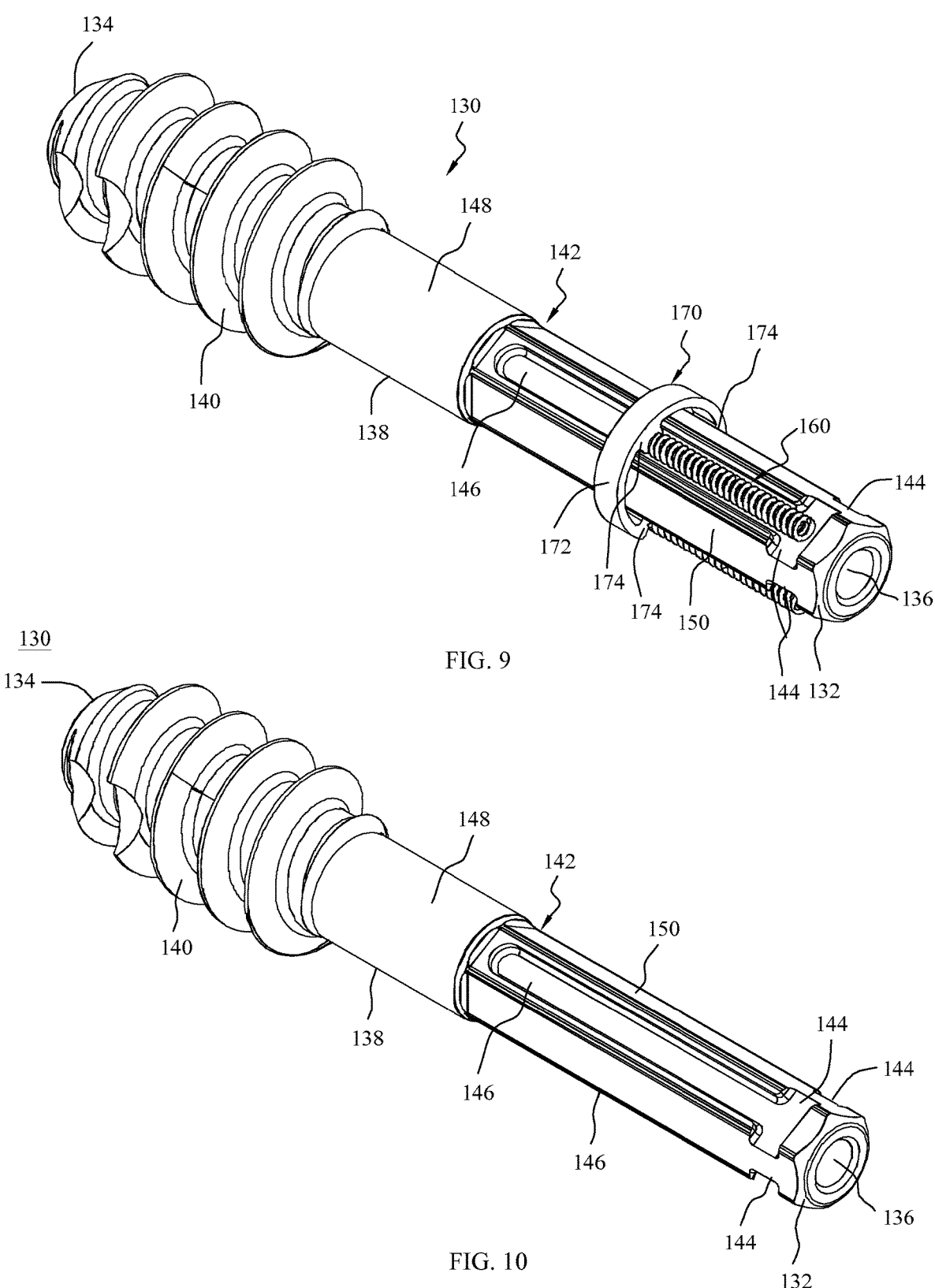
FIG. 9 is a perspective view of a portion of the bone fixation device of FIG. 1 in a second position, in accordance with an aspect of the present invention.
FIG. 10 is a perspective view of a second member of the bone fixation device of FIG. 1, in accordance with an aspect of the present invention.
Figure 11:
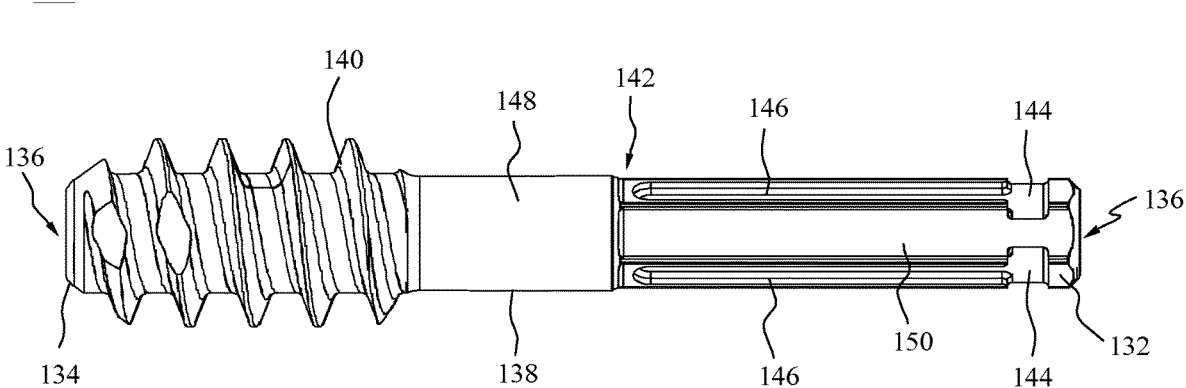
FIG. 11 is a side view of the second member of the bone fixation device of FIG. 1, in accordance with an aspect of the present invention.
Figure 12:
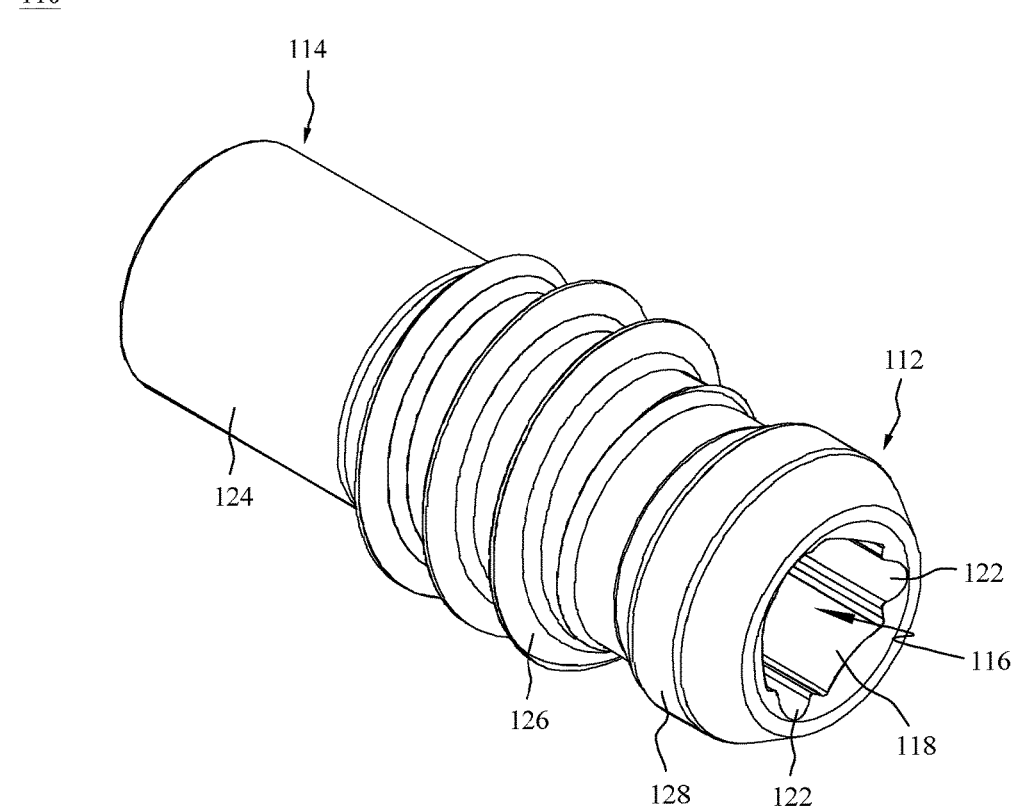
FIG. 12 is an enlarged perspective view of the first member of the bone fixation device of FIG. 1 from a first end, in accordance with an aspect of the present invention.
Figures 13, 14:
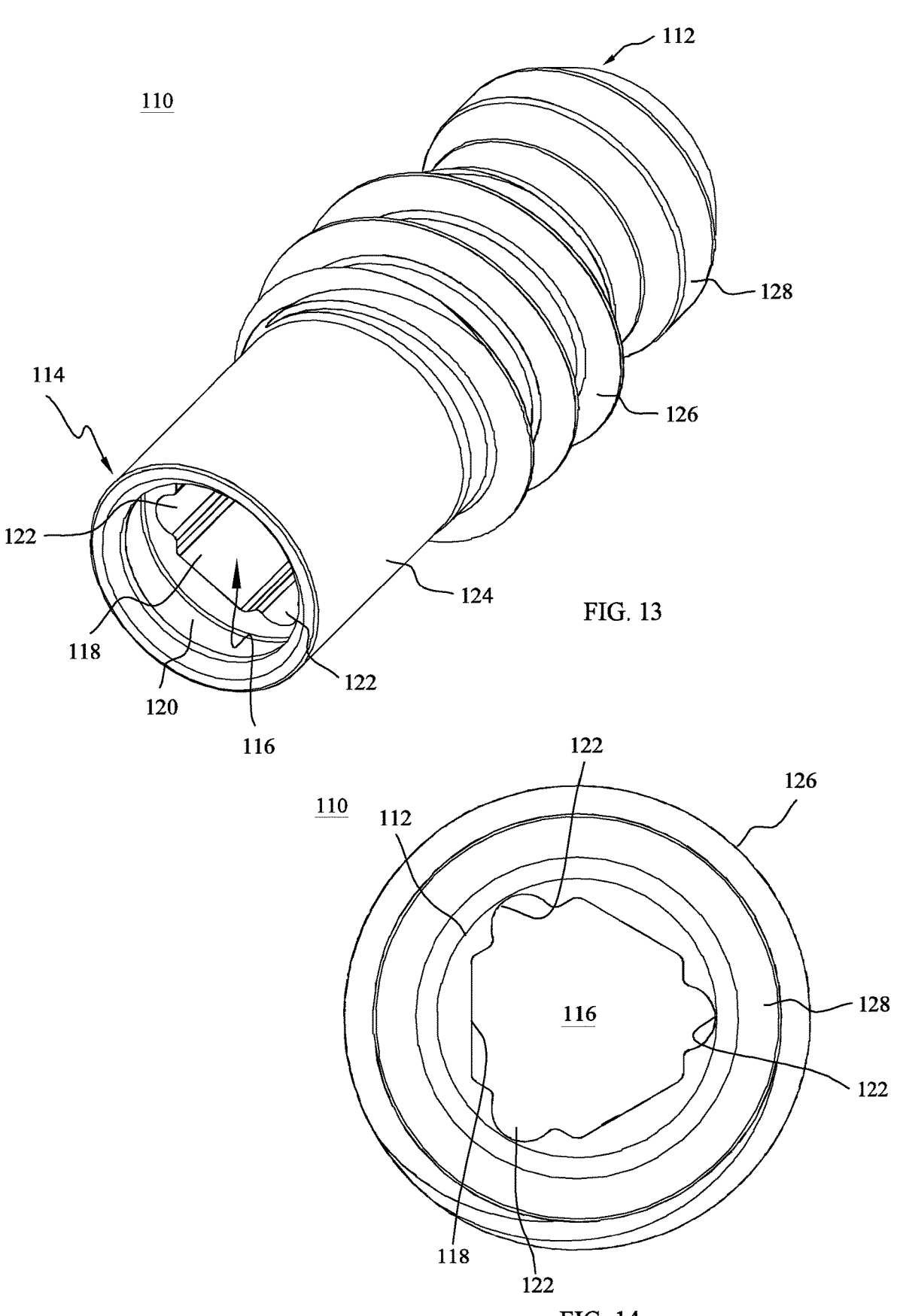
FIG. 13 is an enlarged perspective view of the first member of the bone fixation device of FIG. 1 from a second end, in accordance with an aspect of the present invention.
FIG. 14 is front end view of the first member of the bone fixation device of FIG. 1, in accordance with an aspect of the present invention.
Figure 15:
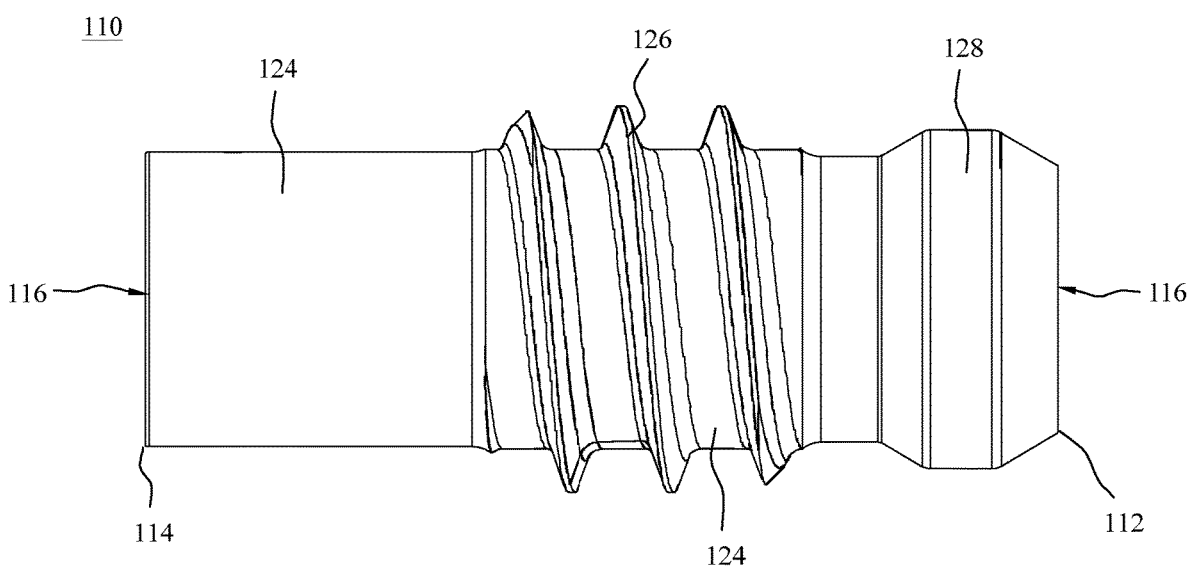
FIG. 15 is a side view of the first member of the bone fixation device of FIG. 1, in accordance with an aspect of the present invention

As shown in FIGS. 10 and 11 and with continued reference to FIGS. 1-7 and 19, the second member 130 may have a first end 132 and a second end 134 opposite the first end 132. The terms "first end" and "proximal end" may be used interchangeably herein and the terms "second end" and "distal end" may also be used interchangeably herein as the generally refer to the same end. The second member 130 may be, for example, a male member. The second member 130 may include a cannulation or channel 136 extending from the first end 132 to the second end 134 through the generally central portion of the second member 130 along the longitudinal axis of the second member 130. The cannulation 136 may be sized to receive a guide wire, guide pin, or the like to facilitate placement in vivo. It is also contemplated that the channel 136 may receive, for example, the at least one spring member 160. The second member 130 may also have an exterior surface 138. The exterior surface 138 of the second member 130 may include a threaded region or threaded end 140 positioned near the second end 134 and a shaft region 142 extending from the threaded region 140 to the first end 132. The threaded region 140 of the second member 130 may have, for example, a smaller diameter than the threaded portion 126 of the first member 110. Alternatively, the threaded region 140 of the second member 130 may have the same diameter as the threaded portion 126 of the first member. In addition, the threaded ends 126, 140 may have, for example, the same threads or different threads. The threads may be selected based on the type and condition of the bone they are being inserted into to ensure the threaded ends 126, 140 grip onto the bones or bone pieces while translation of the bones is occurring.

As shown in FIGS. 8-11, the shaft region 142 may include, for example, a first portion 148 with a generally cylindrical shape and a second portion 150 with a relatively hexagonal or polygonal shape. The second portion 150 may extend from the first end 132 of the second member 130 toward the threaded region 140 and the first portion 148 may be positioned between the threaded region 140 and the second portion 150. The second portion 150 may also include at least one depression or groove 144 near the first end 132 of the second member 130. The at least one depression 144 may include, for example, three depressions positioned radially around the exterior surface of the shaft region 142. Where the second portion 150 of the shaft region 142 has, for example, a polygonal shape with an even number of sides, such as, a hexagon, octagon, or the like, the depressions 144 may be positioned on every other side of the polygonal shape. As shown in FIGS. 8-11, the second portion 150 is generally hexagonal shaped and the depressions 144 are positioned on every other side of the exterior surface 138 to enable insertion of the ring member 170. The second portion 150 may also include at least one channel or slot 146 extending from the at least one depression 144 toward the first portion 148. The at least one channel 146 may be inset into the exterior surface 138. The at least one channel 146 may receive the at least one spring member 160.

The bone fixation device 100 may include, for example, any number of channels 146 and any number of spring members 160, such as one to twelve channels 146 and one to twelve spring members 160. In one embodiment, as shown in FIGS. 4 and 7-9, the bone fixation device 100 may include, for example, at least three channels 146 and at least three spring members 160. The at least three channels 146 may also be positioned radially around the second portion 150 of the exterior surface 138. The exterior surface 138 of the second portion 150 of the shaft region 142 may have a shape corresponding to the shape of the opening 116 in the first member 110. For example, where the exterior surface 138 of the second portion 150 of the shaft region 142 has a relatively hexagonally shape, the channels 146 may be positioned on every other portion of the exterior surface 138, for example, on the first, third, and fifth surfaces and the second, fourth, and sixth surfaces may be generally planar. The shape of the exterior surface may also be, for example, relatively octagonal or another polygonal shape with any number of sides. The exterior surface may have any shape with an even or odd number of sides and a spring channel may be located in one or more of the sides of the exterior surface. At least one spring 160 will be positioned in the at least one spring channel 146.

The at least one spring member 160 may be, for example, three spring members 160 as shown in FIGS. 4, 7-9, and 19. The terms "at least one spring member," "at least one deformable member," and "at least one elastic element" may be used interchangeably herein as the essentially refer to the same members. The bone fixation device 100 may have, for example, at least three spring members 160 that are positioned between at least three channels 122 of the first member 110 and at least three channels 146 of the second member 130 when the second member 130 is inserted into the first member 110. The at least three spring members 160 may be, for example, three single springs or three sets of at least two springs. It is also contemplated that any number of springs or elastic elements, such as solid elastic polymers, nitinol members, or the like, may be used to make up the at least one spring member 160 based on the desired compressive properties of the spring members. The spring members 160 may be, for example, spiral spring members, straight spring members, or any deformable members to allow for the compression and/or distraction of the deformable member and then the transition of the deformable member back to a relaxed state. In one embodiment, the deformable member 160 may be a straight spring with a tab at a first end and a tab at a second end for engaging the first and second members 110, 130 of the bone fixation device 100 and a deformable member extending between the first and second tabs. The straight spring may be made of, for example, a deformable material, such as, nitinol. It is also contemplated that one spring member 160 may be used and the one spring member 160 may be positioned within the opening 136 of the second member 130.

Figure 16:
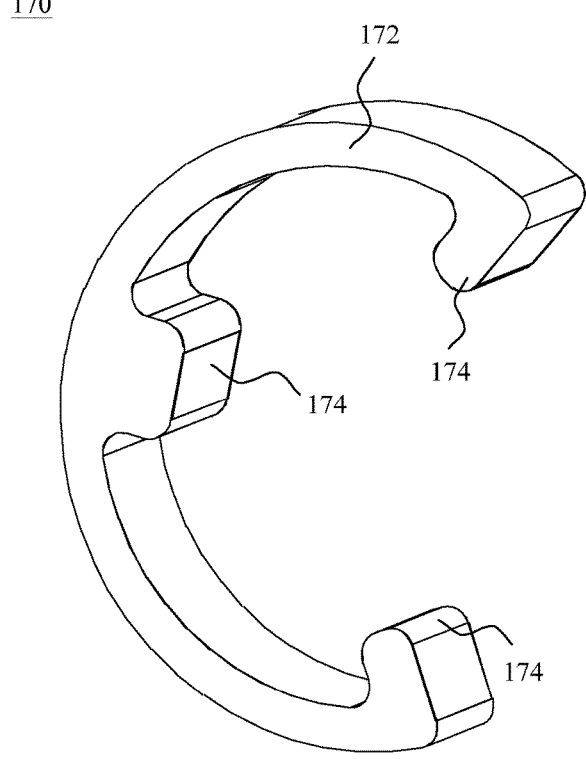
FIG. 16 is a first perspective view of a ring member of the bone fixation device of FIG. 1, in accordance with an aspect of the present invention.
Figure 17:
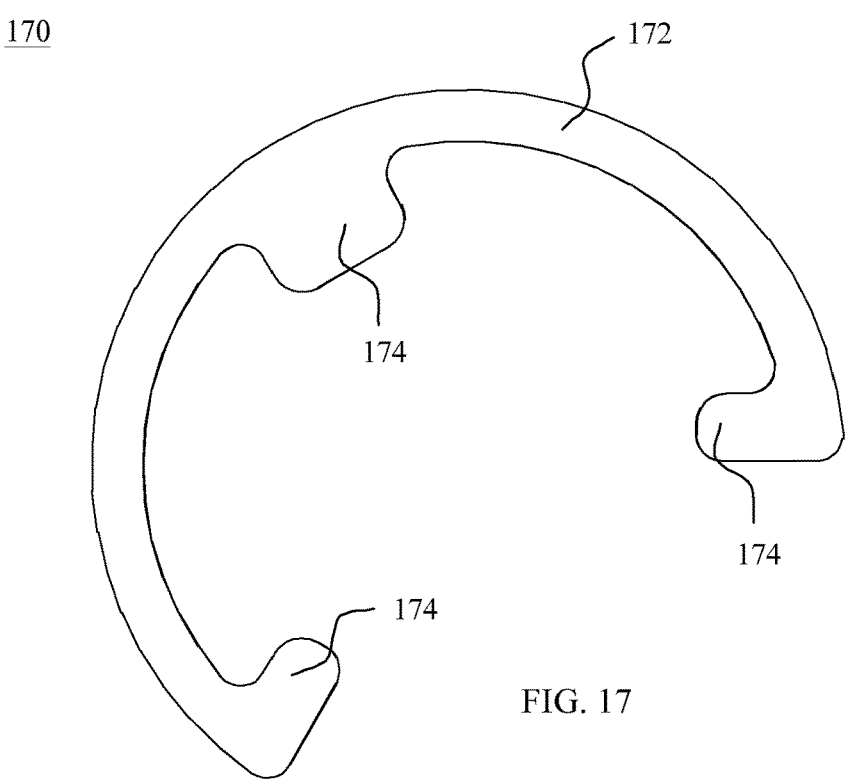
FIG. 17 is a side view of the ring member of the bone fixation device of FIG. 1, in accordance with an aspect of the present invention.
Figure 18:
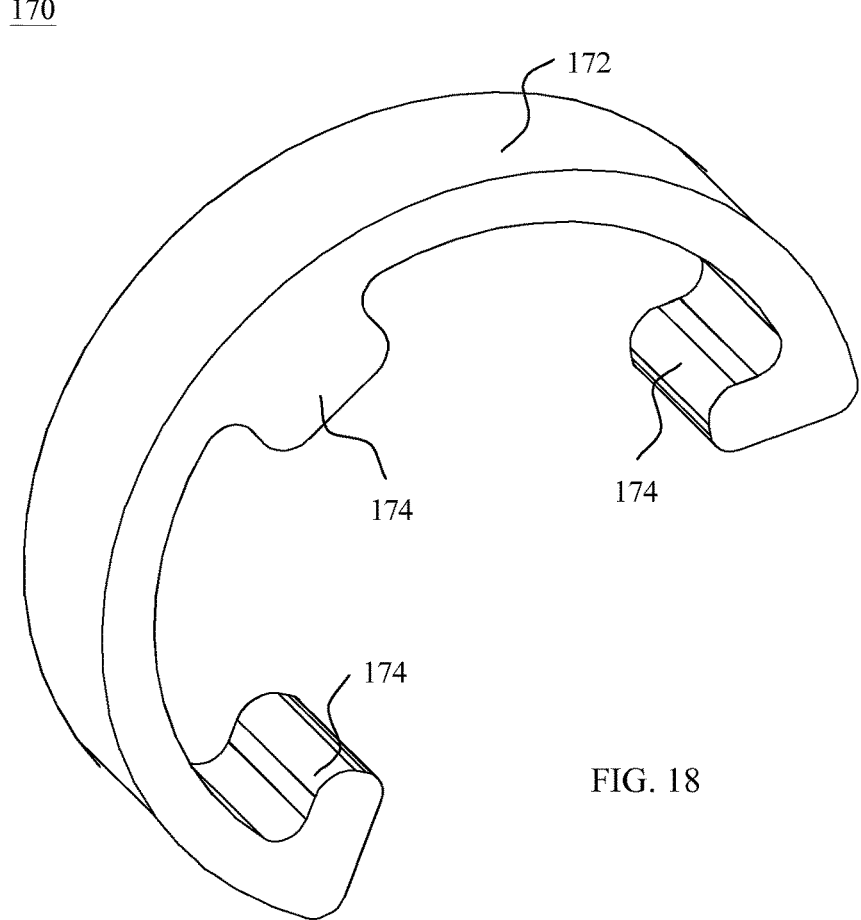
FIG. 18 is a second perspective view of the ring member of the bone fixation device of FIG. 1, in accordance with an aspect of the present invention.

Referring now to FIGS. 16-18, the ring member 170 is shown. The terms "ring member," "member," "ring," "locking member," and "fastener" may be used interchangeably herein as they refer to the same structure. The member 170 may include a body 172. The body 172 may have, for example, a generally cylindrical or C shape and may include an open portion to enable the member 170 to be inserted onto the shaft region 142 of the second member 130. The member 170 may also include at least one protrusion or tab 174 extending out from an interior surface of the body 172. The at least one protrusion 174 may be sized and shaped to correspond to the size and shape of the at least one channel 146 of the second member 130. In the depicted embodiment of FIGS. 16-18, the member 170 includes, for example, three protrusions 174. It is also contemplated that the member 170 may be replaced with, for example, a crimp, set screws, or the like which couples the first member 110 to the second member 130 and provides a base for engagement with the at least one spring member 160.

Further, although not shown, one spring member 160 may be used and positioned in channel 136, the ring member 170 will be configured to engage the spring member 160 inside the channel 136. For example, the ring member 170 may be positioned on the exterior surface 138 of the second member 130 and extend transversely through at least a portion of the channel 136 to provide a base for the spring member 160 to exert force on during compression and expansion. The ring member 170 may extend through an opening, for example, at least one of channels 146 may be open to the channel 136. The ring member 170 may extend transversely through the entire channel 136 and out the side opposite where it entered the exterior surface 138 of the shaft region 142 or only partially through the channel 136. The ring member 170 will extend transversely through the channel 136 far enough to provide a base for the entire or a sufficient portion of the spring to engage during compression and expansion to move the first and second members 110, 130 relative to each other.

The bone fixation device 100 may also include a locking mechanism (not shown) to prevent the first member 110 and second member 130 from lengthening after compression of the bone fixation device 100 is completed. The locking mechanism (not shown) may be, for example, a ratchet mechanism or an alternative mechanism which allows the bone fixation device 100 to lengthen when engaged with the insertion tool or resorbable member and then to shorten after removal of the insertion tool or break down of the resorbable member, but prevents the bone fixation device 100 from lengthening again after removal of the insertion tool (not shown) or break down of the resorbable member (not shown). After the bone fixation device 100 shortens, the locking mechanism may, for example, engage the first member 110 and second member 130 to prevent the bone fixation device 100 from lengthening again when external forces are applied on the bones or bone pieces after insertion of the device 100 into the patient.

By way of specific example, the bone fixation device 100 may be a screw. The screw 100 may be a 5.5 mm screw for example, with the opening 116 of the first member 110 having, for example, a width at the first end 112 of approximately 2.5 mm to 3.5 mm and a diameter at the second end 114 of approximately 4 mm to 5 mm and the shaft region 142 of the second member 130 having, for example, an outer diameter of approximately 2.5 mm to 3.5 mm.

In an alternative embodiment of the bone fixation device 100, the ring member 170 may be removed and at least a portion of the end of the second end 114 of the first member 110 may be crimped or folded over to engage the at least one channel 146 and at least one spring member 160. The second end 114 may be, for example, crimped or folded over at the positions corresponding to or aligning with the position of the channels 146 and spring members 160 or alternatively, around the entire circumference of the first member 110.

Figure 20:
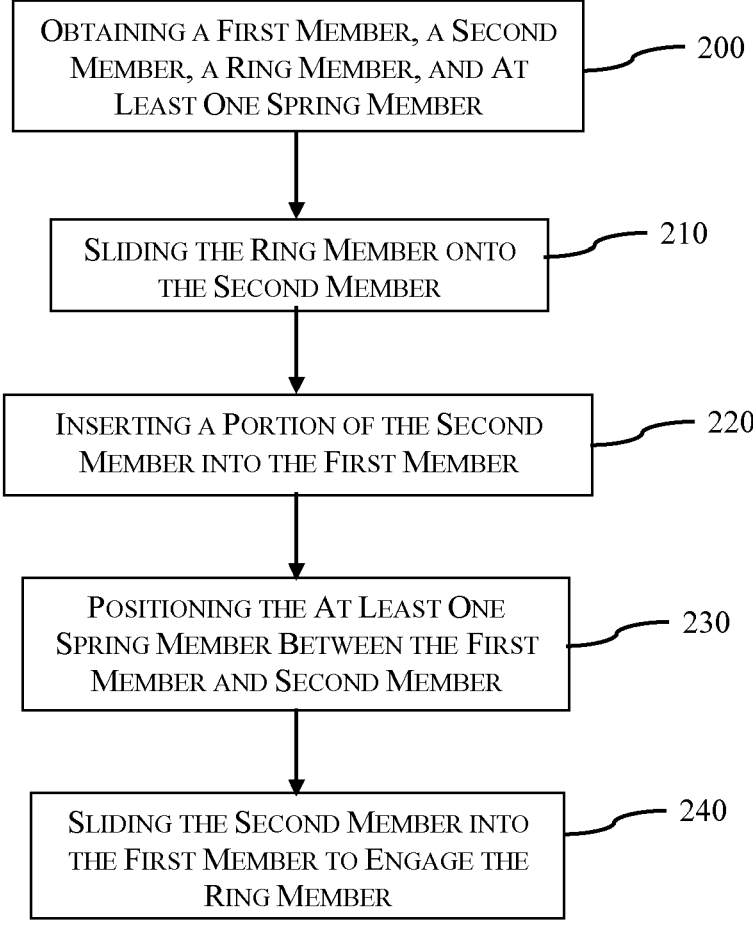
FIG. 20 depicts one embodiment of a method for assembling the bone fixation device of FIG. 1, in accordance with an aspect of the present invention.

A method of assembling a bone fixation device 100 is shown in FIG. 20. The method may include, for example, obtaining a first member, a second member, a ring member, and at least one spring member 200. The method may also include, for example, sliding the ring member onto the second member 210 and inserting a portion of the second member into the first member 220. Further, the method may include, for example, positioning the at least one spring member between the first member and the second member 230 and sliding the second member into the first member to engage the ring member 240.

Figure 4:
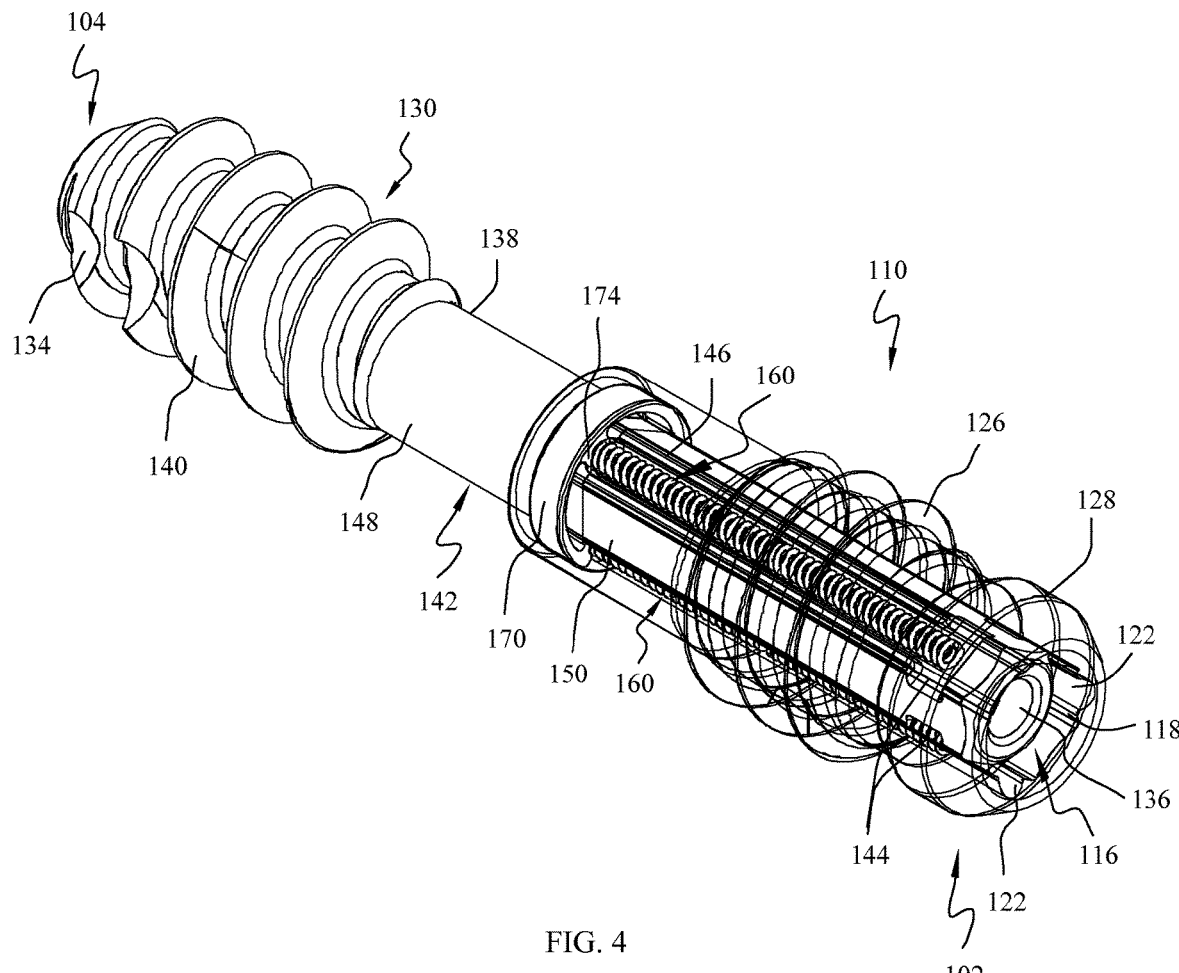
FIG. 4 is a perspective view of the bone fixation device of FIG. 1 with a transparent first member, in accordance with an aspect of the present invention.
Figure 5:
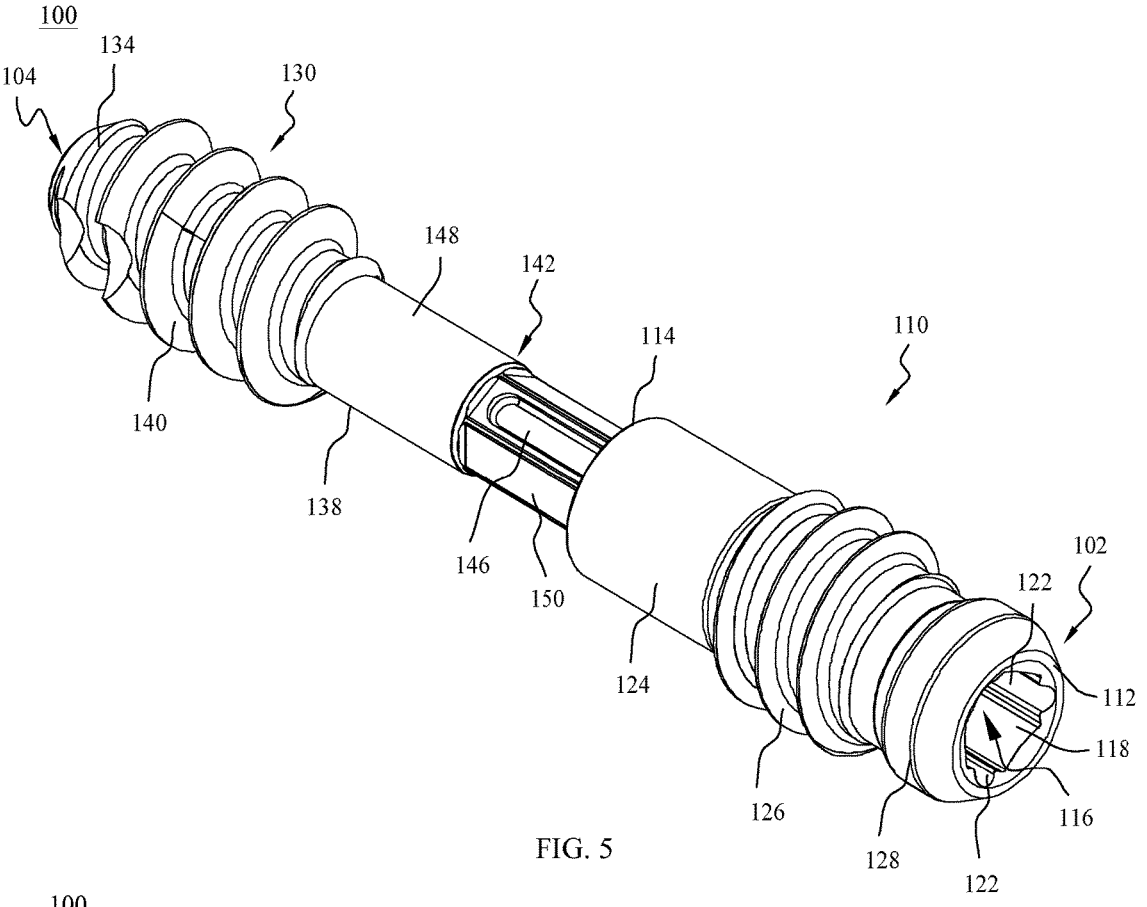
FIG. 5 is a perspective view of the bone fixation device of FIG. 1 from a first end in an expanded position, in accordance with an aspect of the present invention.
Figure 6:
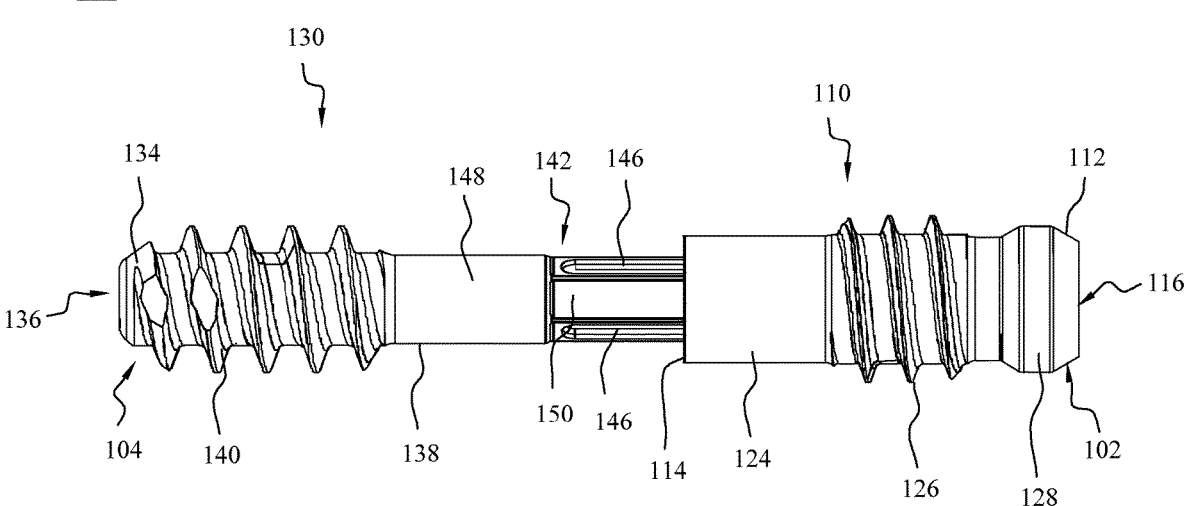
FIG. 6 is a side view of the bone fixation device of FIG. 1 in an expanded position, in accordance with an aspect of the present invention.
Figures 7, 8:
FIG. 7 is a perspective view of the bone fixation device of FIG. 1 in an expanded position with a transparent first member, in accordance with an aspect of the present invention.
FIG. 8 is a perspective view of a portion of the bone fixation device of FIG. 1 in a first position, in accordance with an aspect of the present invention.
Figure 19:
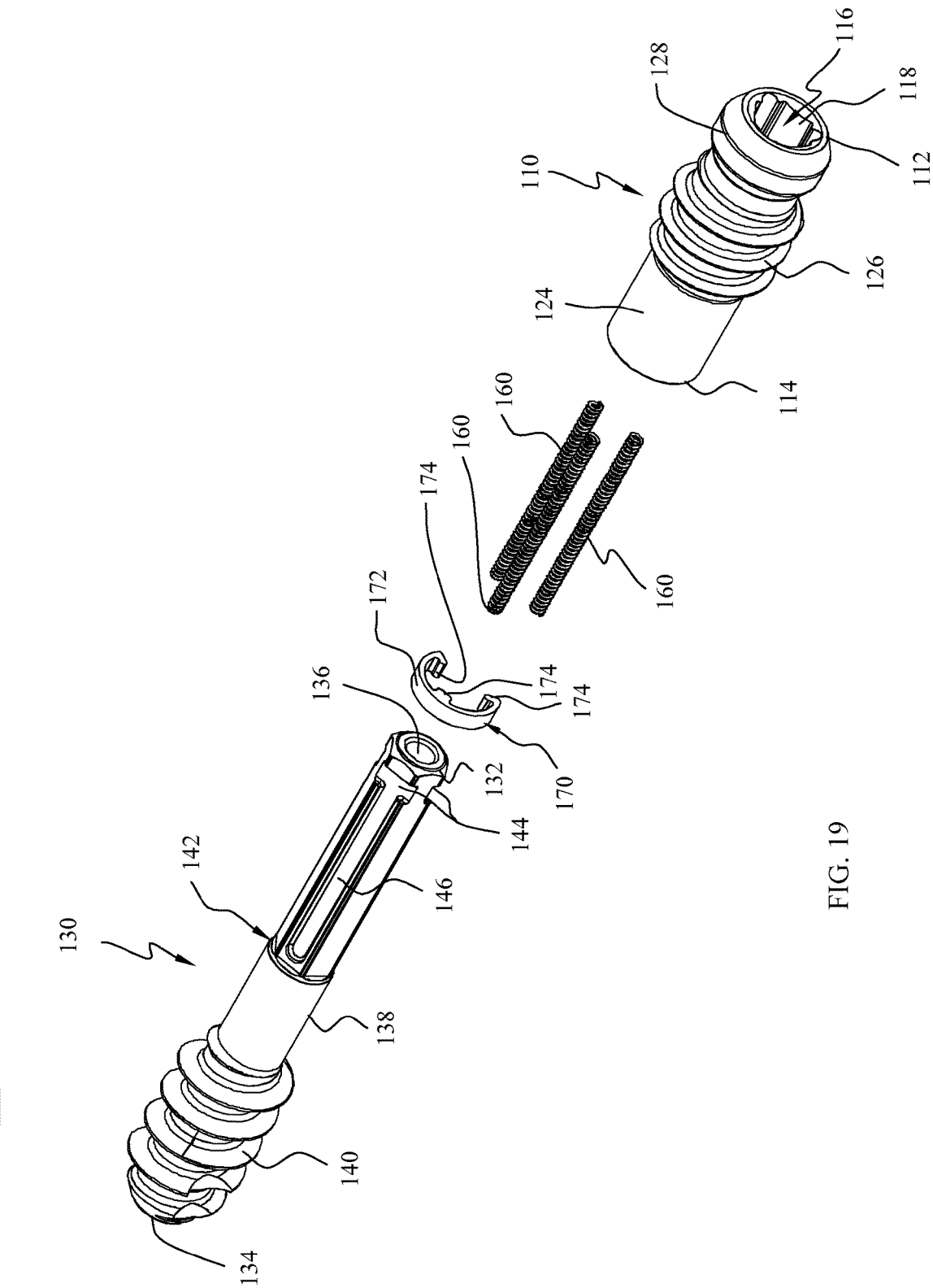
FIG. 19 is an exploded view of the bone fixation device of FIG. 1, in accordance with an aspect of the present invention.

The method of assembling a bone fixation device 100 is described in greater detail below with reference to FIGS. 4, 8-11, and 19. The method includes obtaining the first member 110, a second member 130, a ring member 170, and at least one spring member 160. The at least one spring member 160 may be, for example, three spring members 160 as shown in FIG. 19. Next the ring member 170 may be inserted onto the shaft region 142 of the second member 130, as shown in FIGS. 8 and 9. The ring member 170 may be inserted by aligning, for example, two end protrusions of the at least one protrusion 174 with the depressions 144 on shaft region 142. Then, the ring member 170 may be slid to align with the at least one protrusion 174 with the at least one channel 146 of the second member 130. Once the at least one protrusion 174 of the member 170 is aligned with the at least one channel 146, the member 170 may be translated from the first end 132 distally toward the second end 134 of the second member 130 until the at least one protrusion 172 reaches the bottom of the at least one channel 146. Next, the tip of the first end 132 of the second member 130 may be inserted into the opening 116 of the first member 110. The first and second members 110, 130 may overlap by, for example, overlapping the first member 110 over the first end 132 of the second member 130 down to approximately the depressions 144. Then, the at least one spring member 160 may be positioned in the at least one channel 146 of the second member 130. It is also contemplated that the at least one spring member 160 may be positioned within the at least one channel 146 of the second member 130. The first member 110 may then be slid over the second member 130, as shown in FIGS. 8 and 9. Once the at least one spring member 160 is positioned within the at least one channel 146, the second member 130 may be fully inserted into the first member 110 until the ring member 170 engages the groove 120 in the opening 116 of the first member 110, as shown in FIGS. 4 and 7.

Figure 21:
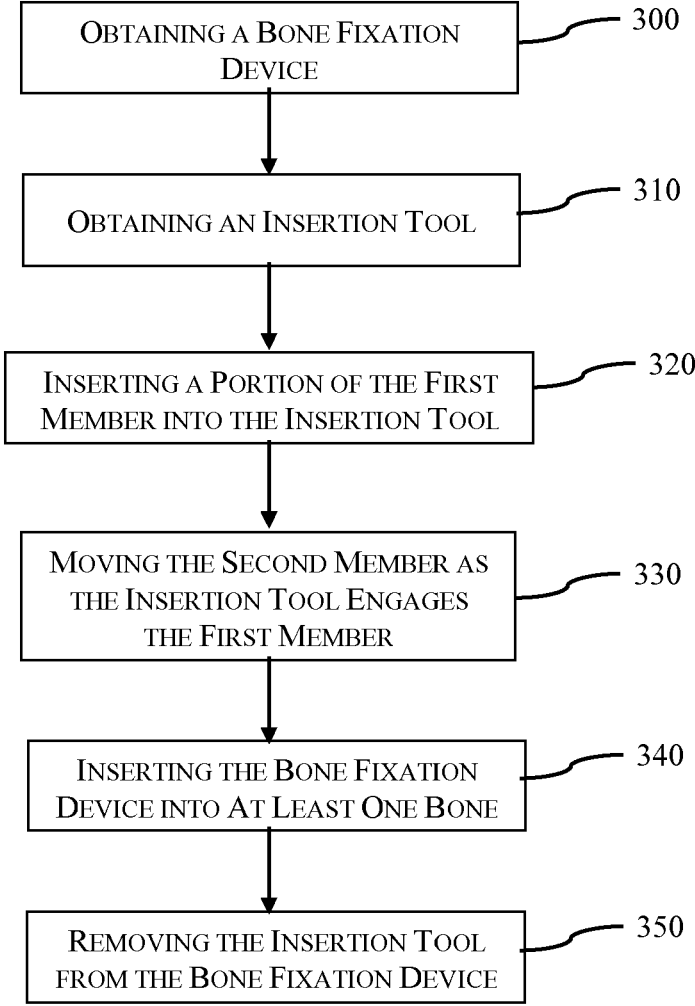
FIG. 21 depicts one embodiment of a method of inserting a bone fixation device, in accordance with an aspect of the present invention.

Referring now to FIG. 21, a method for using the bone fixation device 100 is illustrated. The method may include, for example, obtaining a bone fixation device 300 and an insertion tool 310. The method may also include, for example, inserting a portion of the first member into the insertion tool 320 and moving the second member as the insertion tool engages the first member 330. Finally, the method may further include inserting the bone fixation device into at least one bone 340 and removing the insertion tool from the bone fixation device 350.

The method for using the bone fixation device 100 is described in greater detail below with reference to FIGS. 1-9. The bone fixation device 100 may be inserted into a patient by first optionally inserting a guide wire (not shown) into the position where bone correction is desired. The proper position may be confirmed using imaging, for example, x-ray to ensure the guide wire is properly positioned. The length of the bone fixation device 100 may be confirmed or determined. The bone fixation device 100, such as shown in FIGS. 1-4, may then be obtained. In addition, an insertion tool (not shown) may be obtained and moved to engage the bone fixation device 100.

The bone fixation device 100 is engaged by positioning the insertion tool (not shown) over the protrusion 128 on the first end 112 of the first member 110. An exterior portion of the insertion tool surrounds the protrusion 128 of the first member 110 for insertion into a patient. As the insertion tool engages the first member 110 at the proximal end 102 of the bone fixation device 100, the insertion tool also includes an interior contacting member that extends out from the center of the exterior portion of the insertion tool and engages the first end 132 of the second member 130. The interior contacting member of the insertion tool engages the first end 132 to translate the second end 134 of the second member 130 away from the first end 112 of the first member 110. As the second member 130 is moved away, the ring member 170 which is coupled to the first member 110 slides along the at least one channel 146 of the second member 130. The ring member 170 slides from a position near the first portion 148 of the shaft 142 towards the first end 132 of the second member 130. As the ring member 170 slides towards the first end 132, the protrusions 174 of the member 170 contact the end of the at least one spring member 160. The at least one spring member 160 is then compressed between the at least one protrusion 174 of the ring member 170 and the first end of the at least one channel 122 of the first member 110 and the top of the depressions 144 of the second member 130 as the ring member 170 moves towards the first end 132 of the second member 130. As the ring member 170 moves along the at least one channel 146 and compresses the at least one spring member 160, the threaded ends 126 and 140 move in opposite directions thereby lengthening the bone fixation device 100, as shown in FIGS. 5-7 and 9, to an uncompressed position. Since the ring member 170 is coupled to the first member 110 and the insertion tool is coupled to the first member 110, the second member 130 is able to translate away from the first member 110 as the insertion tool engages the second member 130. Once the at least one spring member 160 is fully compressed the at least one spring member 160 acts as an extension stop by preventing the device 100 from extending any further.

Next, the distal end 104 of the bone fixation device 100 is inserted into the patient over the guide wire. The position of the bone fixation device 100 may then be checked to confirm proper positioning and length.

The insertion tool (not shown) may then be removed from the first member 110. As the insertion tool is removed, active compression is initiated on the bones or bone pieces that the bone fixation device 100 is engaged to and the bone fixation device 100 begins to move back to the shortened compressed position, as shown in FIGS. 1-4. The active compression results from the at least one spring member 160 extending back to its uncompressed position and exerting a force on the ring member 170. As the force is exerted on the ring member 170 by the at least one spring member 160, the ring member 170 translates toward the second end 134 of the second member 130 along the at least one channel 146. Since the ring member 170 is coupled to the groove 120 in the first member 110, the ring member 170 will translate towards the second end 134 of the second member 130 resulting in the first member 110 being pulled toward the distal end 104 of the bone fixation device 100 and causing the bones or bone portions engaged by the first member 110 and second member 130 to be compressed together.

The bone fixation device 100 shortens as the at least one spring member 160 expands back to a resting position. The at least one spring member 160 may allow the bone fixation device 100 to shorten, for example, more than approximately ten percent of the length of the bone fixation device 100. The bone fixation device 100 may, for example, allow for high forces, such as approximately 0.5 lbs to 5 lbs, to be applied over the distance of approximately 3 mm. In addition, the bone fixation device may allow for compression forces to be the strongest at full extension and then decrease as the bone fixation device 100 shortens. Thereby, providing an initially high load compression to enhance healing of the bones or bone pieces and then as healing of the bones or bone pieces occurs, the compression load decreases.

An alternative use for the bone fixation device 100, i.e. lengthening of bones, is described below. It is also contemplated that an alternative tool may be used to shorten the bone fixation device 100 before insertion into a patient to allow for lengthening of the bones after insertion. For example, the insertion tool (not shown) would engage the protrusion 128 on the first end 112 of the first member 110 and also engage the first end 132 of the second member 130. The tool will pull the first end 132 of the second member 130 proximally to shorten the device 100. As the tool engages the device 100 and pulls the first end 132 of the second member 130 proximally, the proximal edge of the first portion 148 of the second member 130 engages the ring member 170 and slides the ring member 170 along the at least one channel 146 toward the first end 112 of the first member 110. As the ring member 170 slides along the at least one channel 146, the ring member 170 engages the at least one spring member 160 and compresses the at least one spring member 160 between the at least one protrusion 174 of the ring member 170 and the first end of the at least one channel 122 of the first member 110 and the top of the depressions 144 of the second member 130. Once the device 100 is shortened to the desired length, it may be inserted into a patient. The device 100 may also optionally be inserted over a guide wire.

Next, the insertion tool may be removed from the bone fixation device 100. Once the tool is removed, the at least one spring member 160 may exert a force on the ring member 170 which will in turn exert a force on the edge of the first portion 148 of the second member 130 to move the second member 130 away from the first member 110 of the bone fixation device 100. As the at least one spring member 160 returns to its' resting, uncompressed state, the bone fixation device 100 lengthens. As the bone fixation device 100 lengthens and moves the first member 110 and second member 130 away from each other, the bones or bone segments that are coupled to the first member 110 and second member 130 are separated. The bone fixation device 100 may be used to provide a distraction force across a joint, fracture site, or osteotomy site.

Alternatively, if a resorbable member (not shown) is used, after placement of the bone fixation device 100 the patient's incision may be closed. If a resorbable member is used, the insertion tool would not need to include a lengthening or shortening mechanism. The resorbable member will hold the bone fixation device 100 in the desired extended or shortened position until the resorbable member starts to break down. As the resorbable member breaks down or erodes over time from exposure to the in vivo environment inside of the patient, the at least one deformable member 160 may be released and exert force on the members 110, 130 to lengthen or shorten the device 100, as described in greater detail above. The resorbable member may be, for example, a cross pin, pawl, or the like which locks the device 100 in the desired extended or shortened position until the resorbable member erodes.

Where the bone fixation device 100 is used to facilitate bone distraction, the bone fixation device 100 may also include a locking mechanism (not shown). The locking mechanism allows for the second member 130 to be pulled proximally toward the first member 110. The second member 130 will then move away from the first member 110 once the insertion tool is removed or resorbable member breaks down from the bone fixation device 100. In addition, once the insertion tool is removed or resorbable member breaks down and the second member 130 begins translating away, the locking mechanism will prevent the second member 130 from again translating towards the first member 110. The locking mechanism may be, for example, a ratcheting mechanism that engages the first member 110 and second member 130 to prevent the shortening of the bone fixation device 100 when the device 100 is implanted and the insertion tool removed or resorbable member breaks down.

FIGS. 22-24 and 31 depict another embodiment of a bone fixation device or bone fusion device 400. The bone fixation device 400 may be, for example, an intramedullary rod for insertion into a medullary cavity of a bone. The device 400 may include a first member 410, a second member 430, at least one spring member 160, and a ring member 170. The second member 430 may be dimensioned to fit into the first member 410 and the at least one spring member 160 and the ring member 170 may be, for example, positioned between the first member 410 and second member 430.

Figure 22:
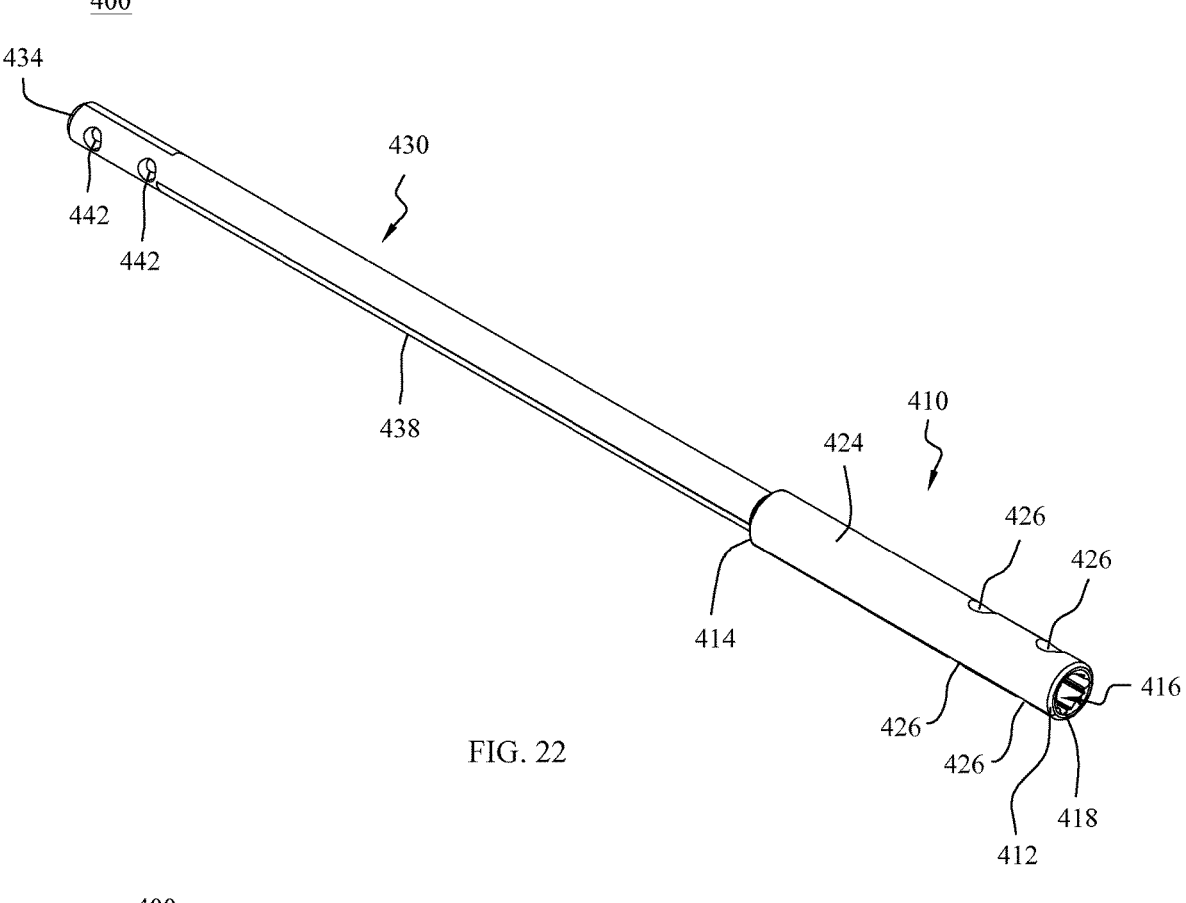
FIG. 22 is a perspective view of another embodiment of a bone fixation device, in accordance with an aspect of the present invention.
Figure 23:
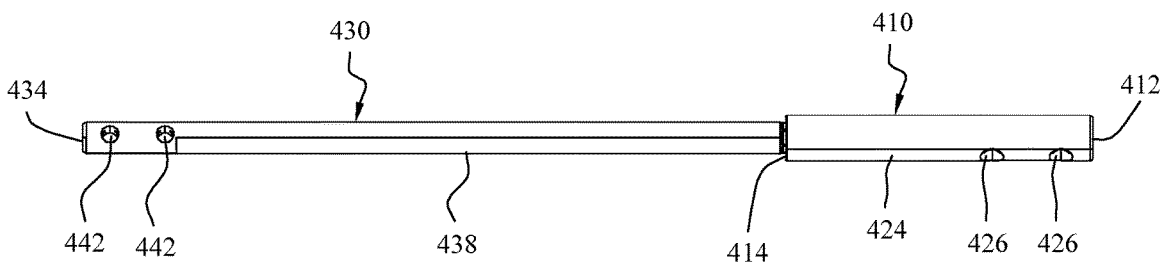
FIG. 23 is a side view of the bone fixation device of FIG. 22, in accordance with an aspect of the present invention.
Figure 24:
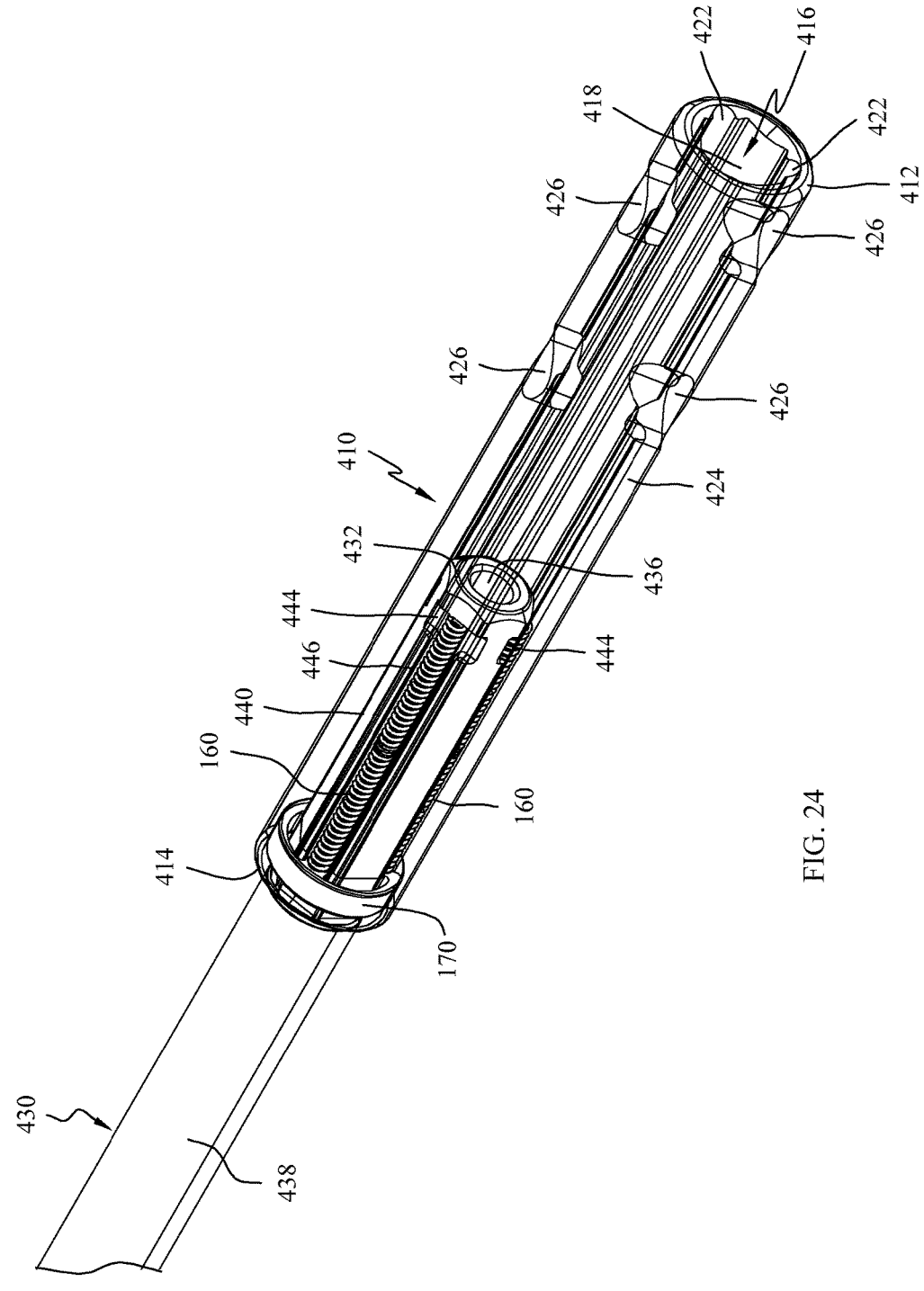
FIG. 24 is a perspective view of a portion of the bone fixation device of FIG. 22 with a transparent first member, in accordance with an aspect of the present invention.

The first member 410, as shown in FIGS. 22-24 and 27-31, may include a first end 412 and a second end 414 opposite the first end 412. The first member 410 may also have an opening 416 extending from the first end 412 to the second end 414 along the longitudinal axis of the first member 410. The opening 416 may form an interior surface 418 which includes a groove 420 positioned near the second end 414 of the first member 410. The groove 420 may extend into the first member 410 from an interior surface 418 toward the exterior surface 424 of the first member 410. The interior surface 418 of the first member 410 may have, for example, a relatively hexagonal, octagonal, or other polygonal shape from the first end 412 to the groove 420. In addition, the opening 416 may include at least one channel or slot 422 inset into the interior surface 418 and extending from the first end 412 toward the second end 414 and terminating when the channels 422 extend into the groove 420. The first member 410 may be, for example, a female member. The device 400 may include, for example, at least three channels 422 which may receive at least three spring members 160, as shown in FIG. 24. The at least three channels 422 may be positioned radially around the opening 416 as described in greater detail above with reference to channels 122 and opening 116, which will not be described again here for brevity sake.

With continued reference to FIGS. 22-24 and 27-31, the exterior surface 424 of the first member 410 may be, for example, generally cylindrical. The exterior surface 424 may include at least one through hole 426 for fixing the rod 400 to a first portion of a patient's bone. In the depicted embodiment, the at least one through hole 426 may be, for example, two through holes 426. Alternative numbers of holes 426 are also contemplated to secure the rod 400 to a patient's bone and the number of holes 426 may correlate to the length of the bone being fused.

The second member 430, as shown in FIGS. 22-26, may have a first end 432 and a second end 434 opposite the first end 432. The second member 430 may include a cannulation or channel 436 extending from the first end 432 to the second end 434 along the longitudinal axis of the second member 430 and through the generally central portion of the second member 430. The cannulation 436 may be sized to receive a guide wire, guide pin, or the like to facilitate placement in vivo. The second member 430 may also include at least one through hole 442 near the second end 434 for fixing the rod 400 to a second portion of a patient's bone. In the depicted embodiment, the at least one through hole 442 may be, for example, two through holes 442.

Figures 25, 26:
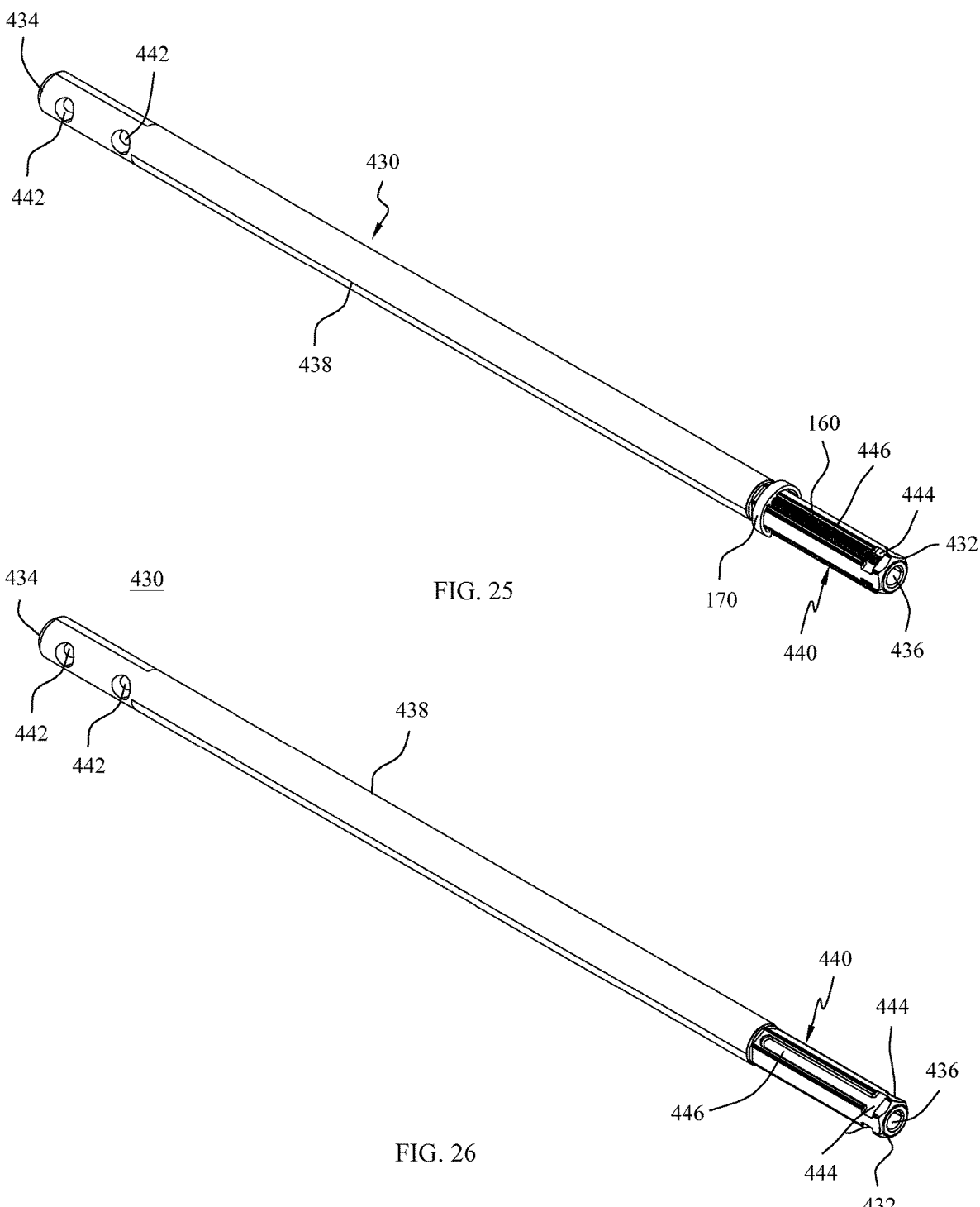
FIG. 25 is a perspective view of the bone fixation device of FIG. 22 with the first member removed, in accordance with an aspect of the present invention.
FIG. 26 is a perspective view of a second member of the bone fixation device of FIG. 22, in accordance with an aspect of the present invention.
Figure 27:
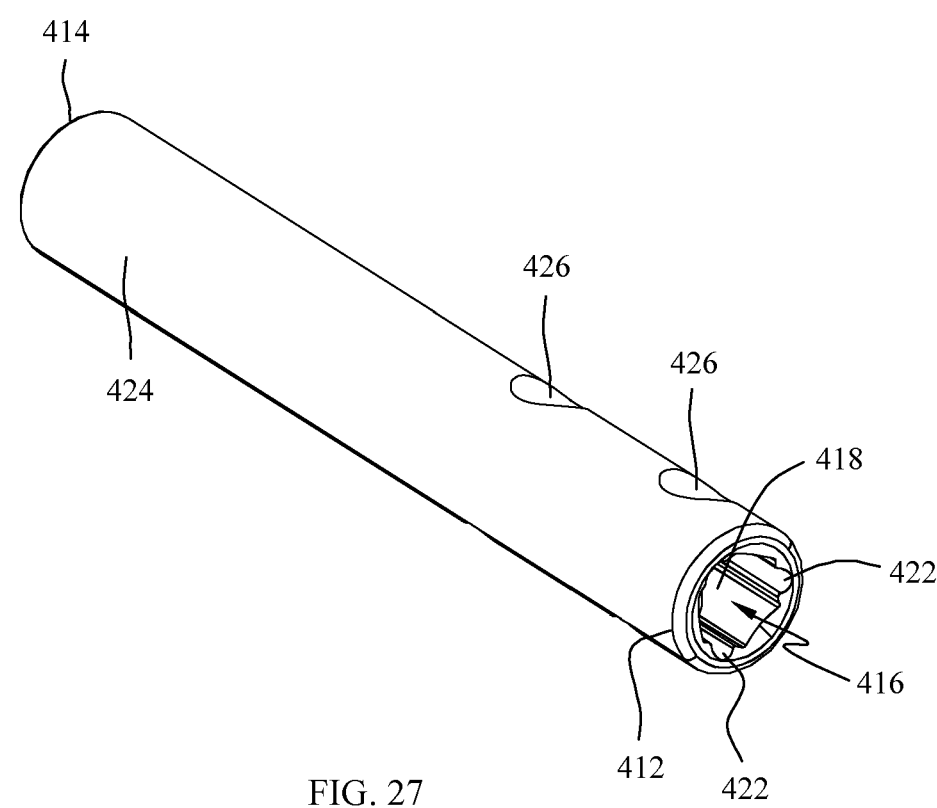
FIG. 27 is a perspective view of the first member of the bone fixation device of FIG. 22 from a first end, in accordance with an aspect of the present invention.
Figure 28:
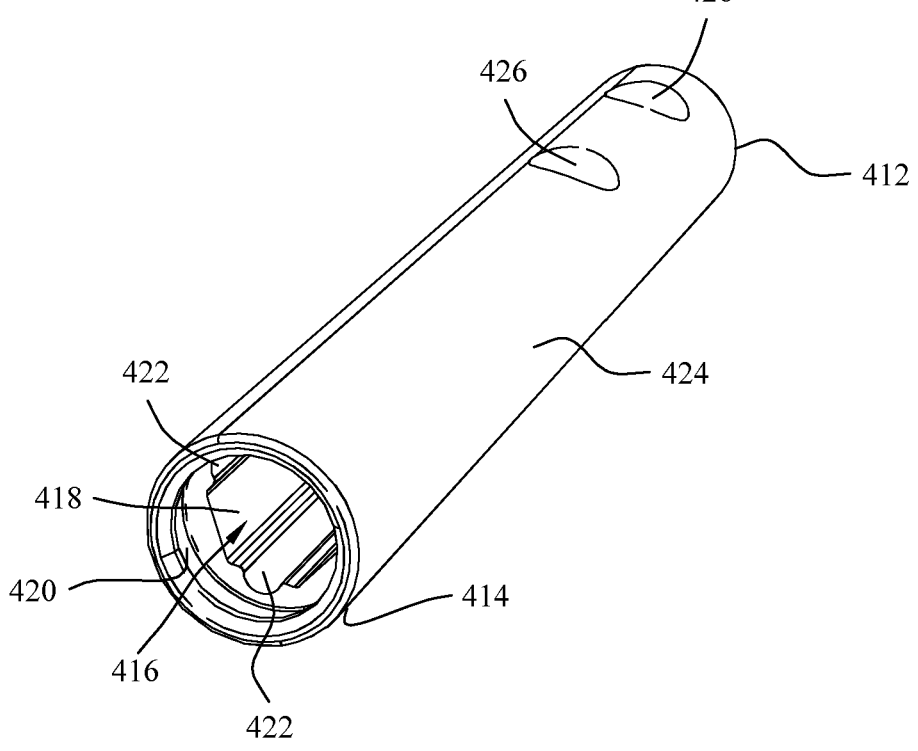
FIG. 28 is a perspective view of the first member of the bone fixation device of FIG. 22 from a second end, in accordance with an aspect of the present invention.
Figure 29:
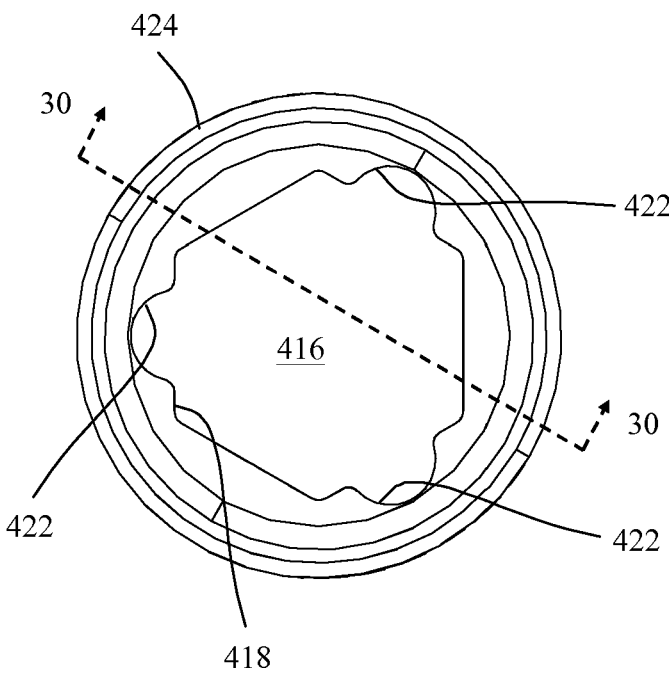
FIG. 29 is an end view of the first member of the bone fixation device of FIG. 22, in accordance with an aspect of the present invention.
Figure 30:
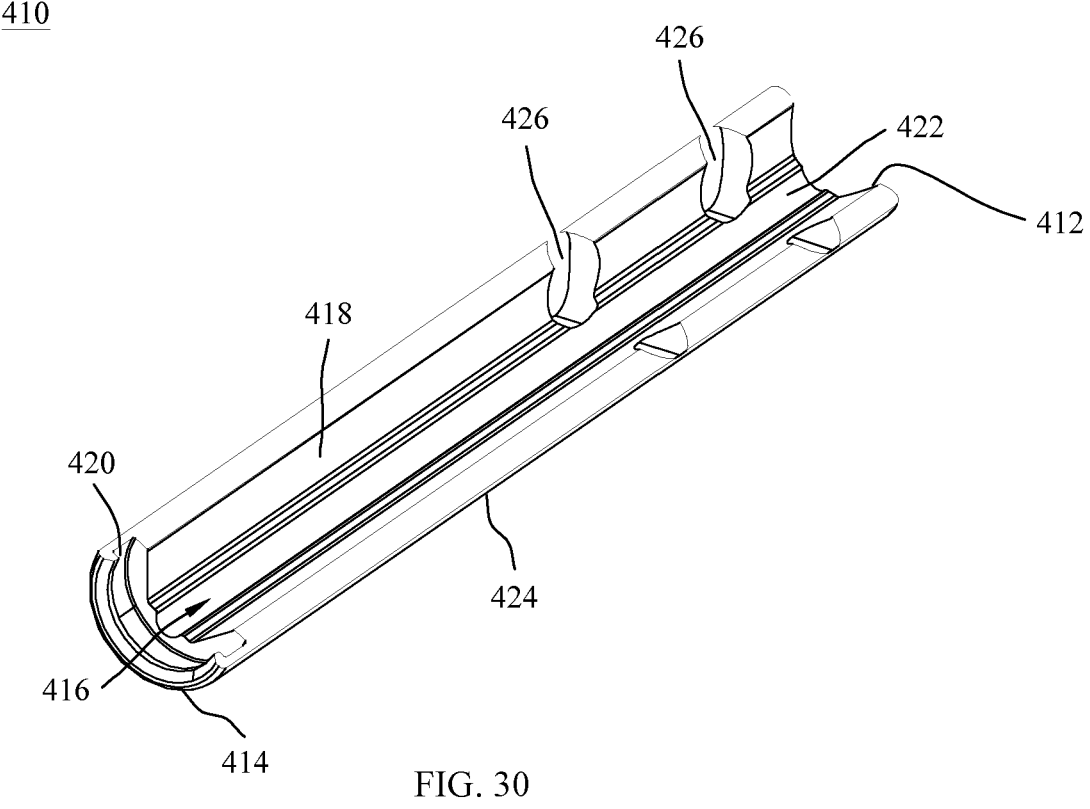
FIG. 30 is a cross sectional view of the first member taken along line 30-30 in FIG. 29, in accordance with an aspect of the present invention.

As shown in FIGS. 24-26, the second member 430 may also have an exterior surface 438 with a coupling portion 440 positioned near the first end 432 for connecting the second member 430 to the first member 410. The exterior surface 438 positioned distal to the coupling portion 440 may have a generally cylindrical shape, while the coupling portion 440 may have a relatively polygonal shape. The coupling portion 440 may also include at least one depression or groove 444 near the first end 432 of the second member 430. The at least one depression 444 may be, for example, three depressions 444 positioned radially around the exterior surface 438 of the coupling portion 440. For example, if the coupling portion 440 has a polygonal shape with an even number of sides, the depressions 444 may be positioned on every other side of the polygonal shape. The at least one depression 444 is positioned around the coupling portion 440 so that the ring member 170 may be inserted onto the second member 430. The coupling portion 440 may also include at least one channel or slot 446 extending from the at least one depression 444 toward the second end 434. The at least one channel 446 may be inset into the exterior surface 438 and may be sized to receive the at least one spring member 160. The bone fixation device 400 may include, for example, any number of channels 446 and any number of spring members 160, which may be one to twelve channels 446 and one to twelve spring members 160. In one embodiment, the channels 446 and spring members 160 may be, for example, three channels 446 and at least three spring members 160, as shown in FIGS. 24 and 25. The channels 446 may be positioned radially around the coupling portion 440. It is also contemplated that in an alternative embodiment, the channel 436 may receive, for example, the at least one spring member 160. The coupling portion 440 may be sized to fit within the opening 416 of the first member 410. In addition, the shape of the coupling portion 440 may correspond to the shape of the opening 416 in the first member 410. The second member 430 may be, for example, a male member.

The at least one spring member 160 may be positioned between the at least one channel 422 of the first member 410 and the at least one channel 446 of the second member 430 when the second member 430 is inserted into the first member 410. The at least one spring member 160 is as described above with reference to FIGS. 4, 7-9, and 19, which will not be described again here for brevity sake.

Figure 31:
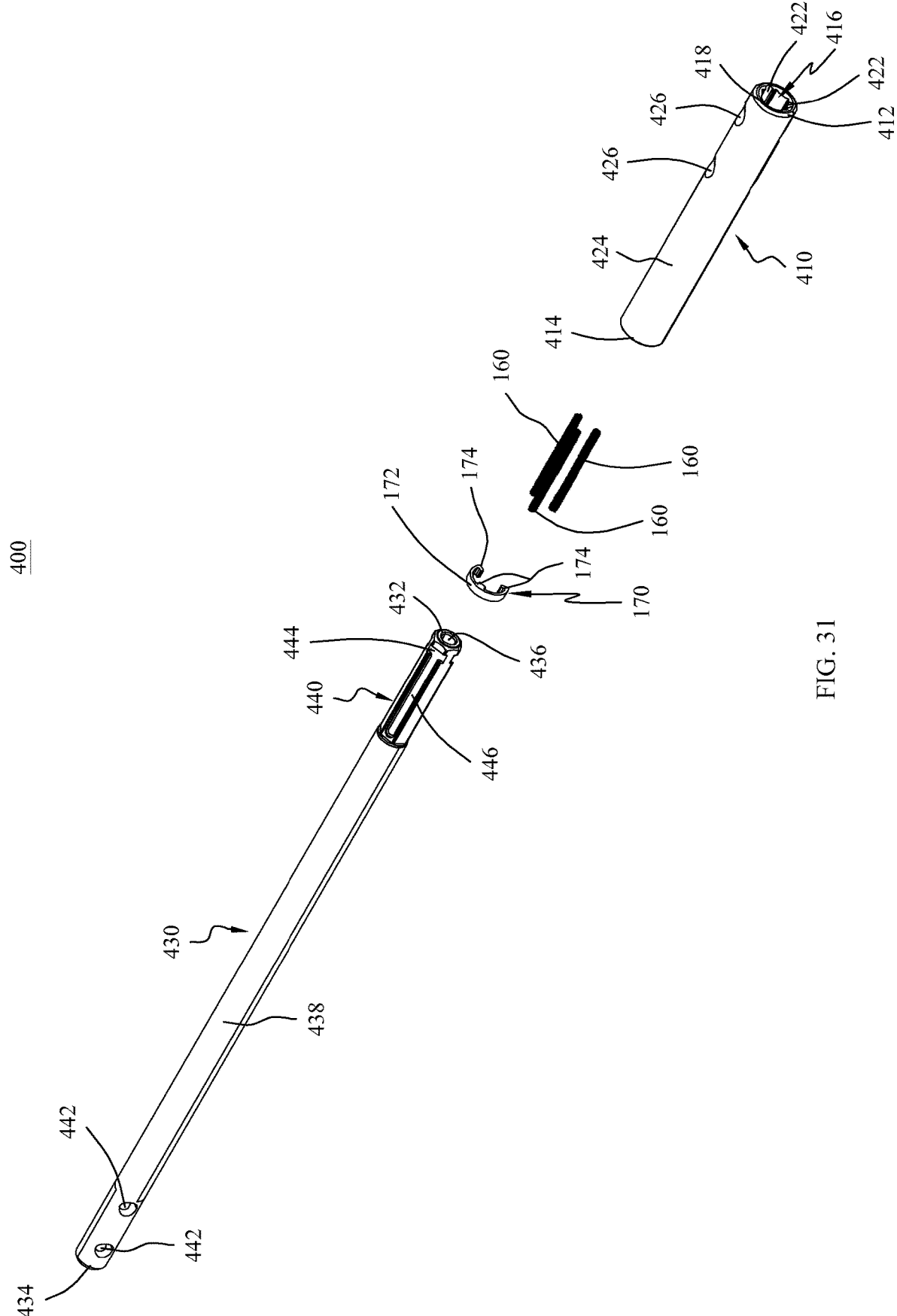
FIG. 31 is an exploded view of the bone fixation device of FIG. 22, in accordance with an aspect of the present invention.

As shown in FIGS. 24, 25, and 31, the ring member 170 may be of the type described above with reference to FIGS. 16-18, which will not be described again here for brevity sake. The ring member 170 may be inserted by sliding the at least one protrusion 174 into the at least one depression 444 of the second member 430 until the at least one protrusion 174 aligns with the at least one channel 446. Once at least one protrusion 174 is aligned with the at least one channel 446, the ring member 170 may be translated toward the distal end of the at least one channel 446. After the ring member 170 is positioned at the distal end of the at least one channel 446, the at least one spring 160 may be inserted into the channel 446 and the coupling portion 440 may be inserted into the opening 416 in the first member 410. When the coupling portion 440 is inserted into the opening 416, the at least one spring 160 slides into the at least one channel 422 of the first member 410. Alternatively, it is contemplated that one spring member 160 may be used and positioned in channel 436. If the spring member 160 is positioned in the channel 436, the ring member 170 will be configured to engage the spring member 160 inside the channel 436. The alternative embodiment is described in greater detail above with respect to bone fixation device 100 and will not be described again here for brevity. The coupling portion 440 may be inserted into the first member 410 until the ring member 170 engages the groove 420 in the first member 410 to secure the first member 410 and the second member 430 together.

The bone fixation device 400 may also include a locking mechanism (not shown) to prevent the first member 410 and the second member 430 from lengthening after compression is complete or from shortening after distraction is completed. The locking mechanism may be of the type described above in greater detail with respect to device 100 and which will not be described again here for brevity sake.

By way of specific example, the bone fixation device 400 is an intramedullary rod. The intramedullary rod may be, for example, approximately 240 mm to 420 mm with a first member 410 with a diameter of, for example, approximately 12 mm to 17 mm and a second member 430 with a diameter of, for example, approximately 9 mm to 14 mm.

The method of assembling a bone fixation device as shown in FIG. 20 and described in greater detail above may also be used to assemble the bone fixation device 400.

The bone fixation device 400 may be inserted into a patient using the method of FIG. 21. The method is described in greater detail with respect to device 400 and may include, for example, obtaining an assembled bone fixation device 400 and insertion tool (not shown). The method may also include, for example, inserting a portion of the first member 410 into the insertion tool (not shown) and moving the second member 430 as the insertion tool engages the first member 410 to, for example, lengthen the device 400 if compression of the bone is desired. As the device 400 is lengthened the at least one spring member 160 will be compressed by the ring member 170. The insertion tool may engage the device 400 in a manner similar to how the insertion tool engages the device 100 as described above in greater detail and which will not be described again here for brevity sake. Next, the method may include inserting the bone fixation device 400 into, for example, the medullary cavity of a long bone.

The device 400 may be inserted into the medullary cavity by first accessing the patient's bone by, for example, making an incision to reach the patient's bone. Then, a guide wire (not shown) may optionally be inserted into the position where bone correction is desired. The position of the guide wire may be checked using imaging, for example, an x-ray to ensure the guide wire is properly positioned. The guide wire may then be used to determine or confirm the length of the intramedullary rod 400 that is needed for insertion into the bone. A drill, reamer, or the like may then be inserted over the guide wire to create a larger opening in the bone to access the medullary cavity. Once the larger opening is formed, the drill or reamer may be removed and the bone fixation device 400 with the coupled insertion tool may be inserted into the medullary cavity through the larger opening. The device 400 may be inserted over the guide wire, or optionally, the guide wire may be removed prior to insertion of the device 400. If necessary, the device 400 may be hammered into the medullary cavity across the fracture. Once the rod 400 reaches the desired position, at least one fastener (not shown), such as, a bone screw, locking bone screw, or the like, may be inserted into the through holes 426 to secure the first member 410 to a first portion of the bone. Next, at least one fastener (not shown), such as, a bone screw, locking bone screw, or the like, may be inserted into the through holes 442 to secure the second member 430 to a second portion of the bone.

Following the insertion of the fasteners to secure the first and second members 410, 430 to the bone, the insertion tool may be removed from the first member 410 of the rod 400. After the insertion tool is removed, the device 400 may exert active compression on the bones secured to the device 400. As active compression occurs, the bone fixation device 400 begins to move back to a shortened compressed position, as shown in FIGS. 22 and 23. The active compression of the rod 400 results from the at least one spring member 160 extending back to its uncompressed position which in turn exerts a force on the ring member 170 to move it toward the distal end of the at least one channel 446. As the ring member 170 translates down the channel 446, the first member 410 is pulled toward the second end 434 of the second member 430 and the bones engaged by the first and second members 410, 430 are compressed together. Finally, the incisions in the patient may be closed. The intramedullary rod 400 may, for example, create an active circumferential compression to the fracture site transferring the axial load to the bone and reducing the function of the rod 400 as a load bearing device. Thus, use of the rod 400 may enhance healing of the bone.

It is also contemplated that the bone fixation device 400 may alternatively be used for distraction of a fractured bone after the insertion, by shortening the device 400 prior to insertion into a patient, as described above in greater detail with regards to bone fixation device 100 and which will not be described again here for brevity sake.

Further, it is contemplated that a resorbable member (not shown) may be used instead of the insertion tool to shorten or lengthen the device 400 for insertion into the patient. Therefore, when a resorbable member is used, the insertion tool could be any driver or holder that could insert the device 400 into the patient. When a resorbable member is used, once the bone fixation device 400 is placed in the patient, the patient's incision may be closed. The resorbable member will hold the bone fixation device 400 in the desired extended or shortened position until the resorbable member starts to break down or erode. As the resorbable member breaks down over time from exposure to the in vivo environment inside of the patient, the at least one deformable member 160 may be released and exert force on the members 410, 430 to lengthen or shorten the device 400, as described in greater detail above. The resorbable member may be, for example, a cross pin, pawl, or the like which locks the device 400 in the desired extended or shortened position until the resorbable member erodes.

Figure 32:
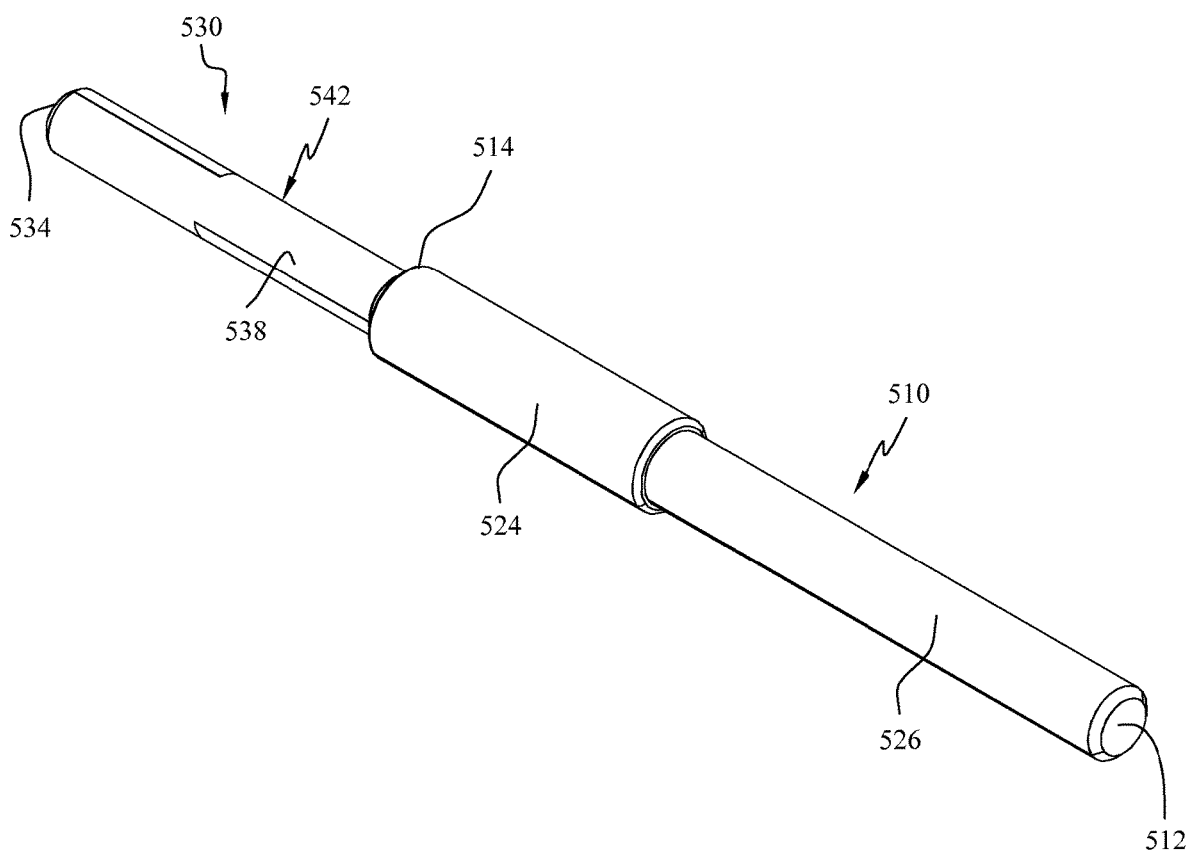
FIG. 32 is a perspective view of another embodiment of a fixation device, in accordance with an aspect of the present invention.
Figure 33:
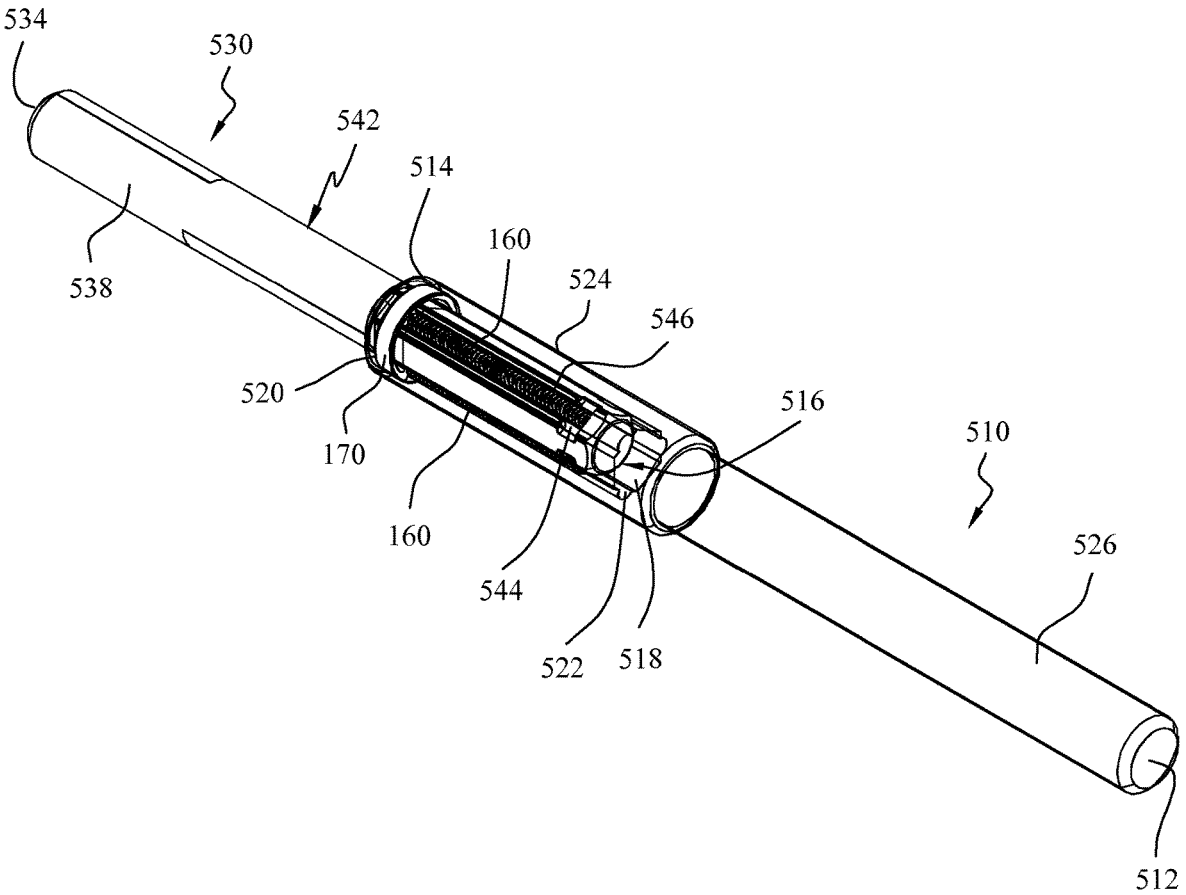
FIG. 33 is a perspective view of the fixation device of FIG. 32 with a transparent first member, in accordance with an aspect of the present invention.
Figure 34:
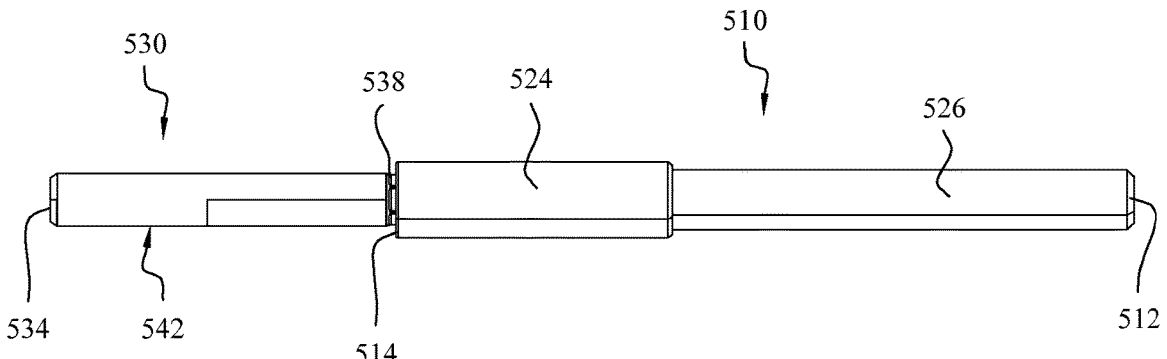
FIG. 34 is a side view of the fixation device of FIG. 32, in accordance with an aspect of the present invention.
Figure 41:
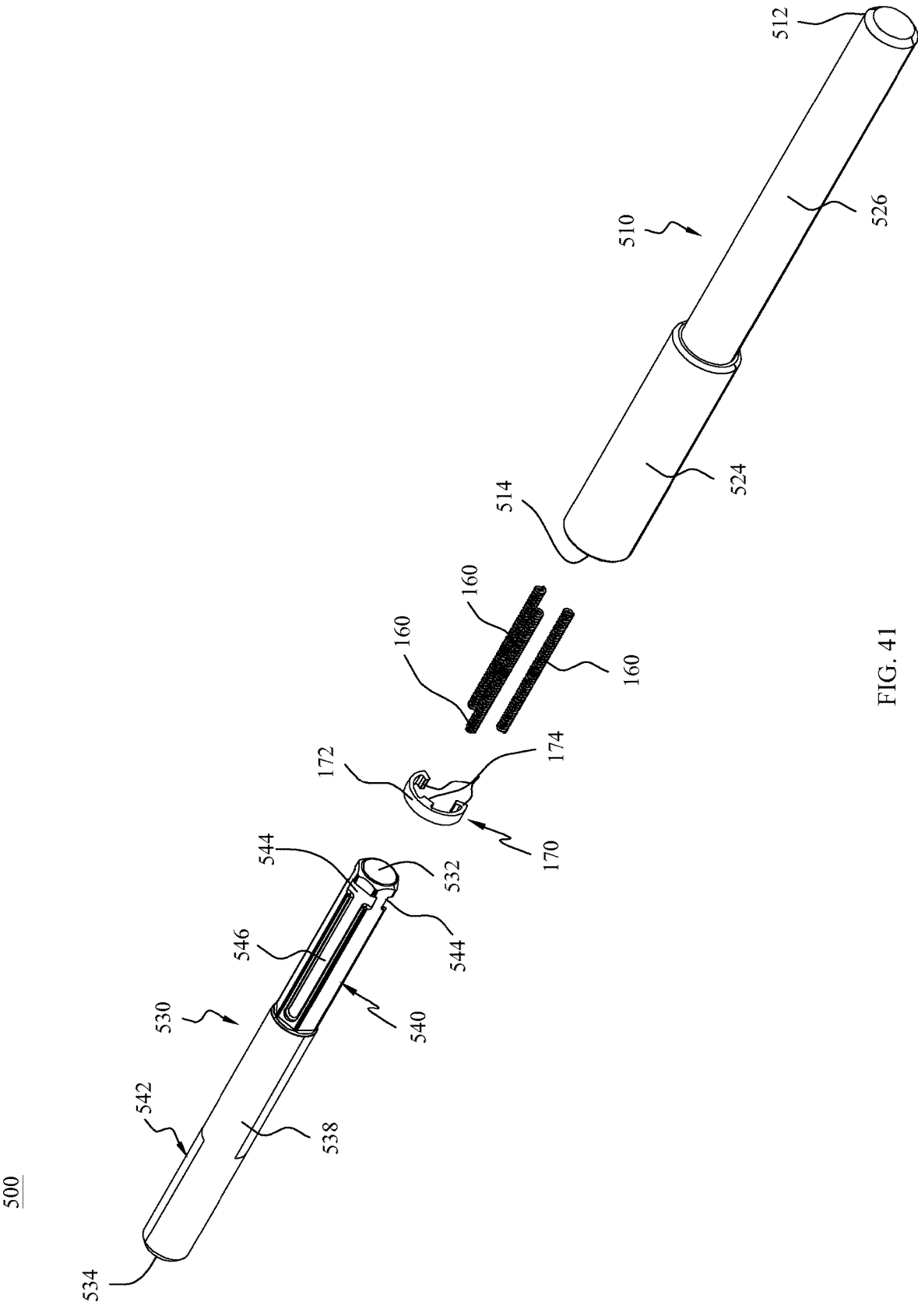
FIG. 41 is an exploded view of the fixation device of FIG. 32, in accordance with an aspect of the present invention.
Figure 42:
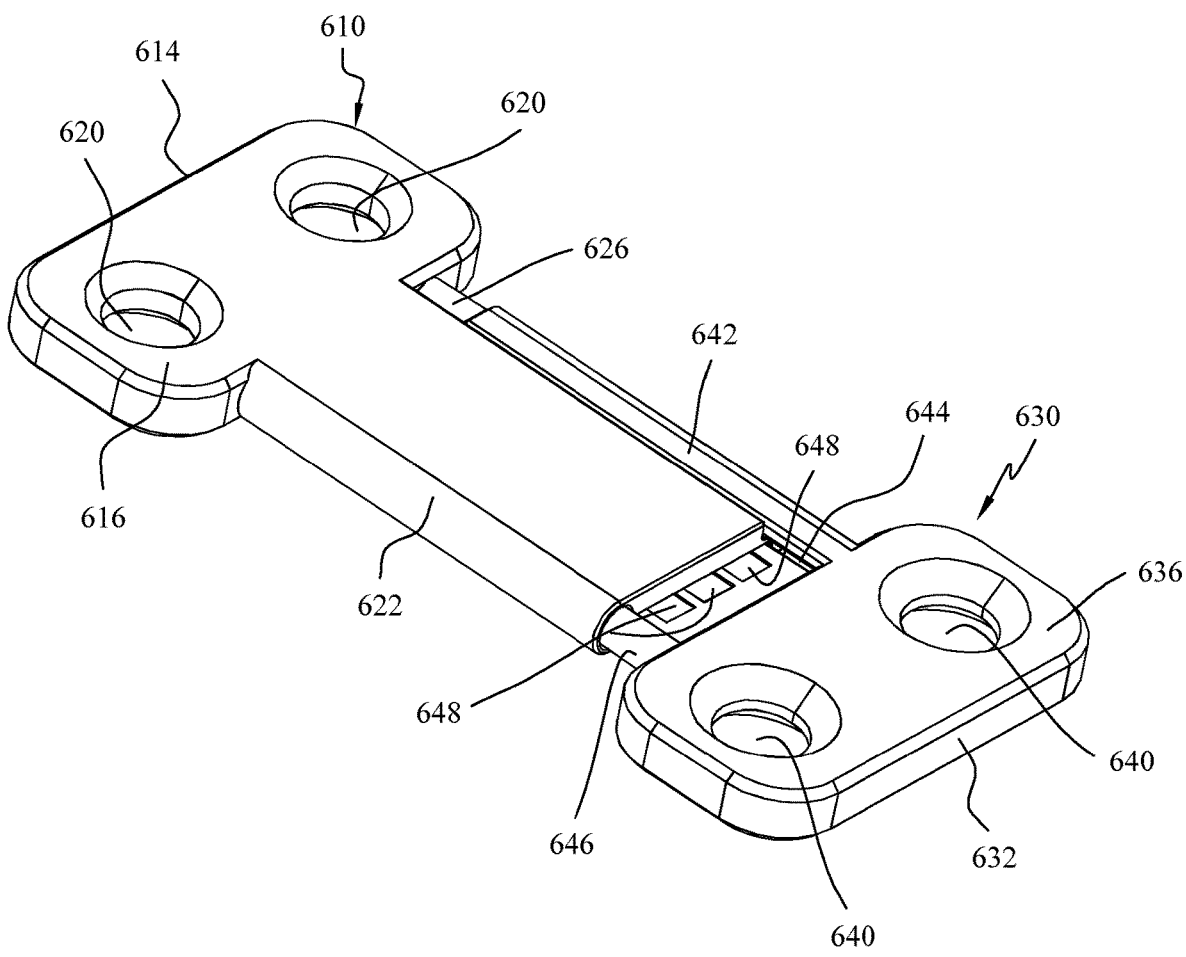
FIG. 42 is a perspective view of a plating device, in accordance with an aspect of the present invention.
Figure 43:
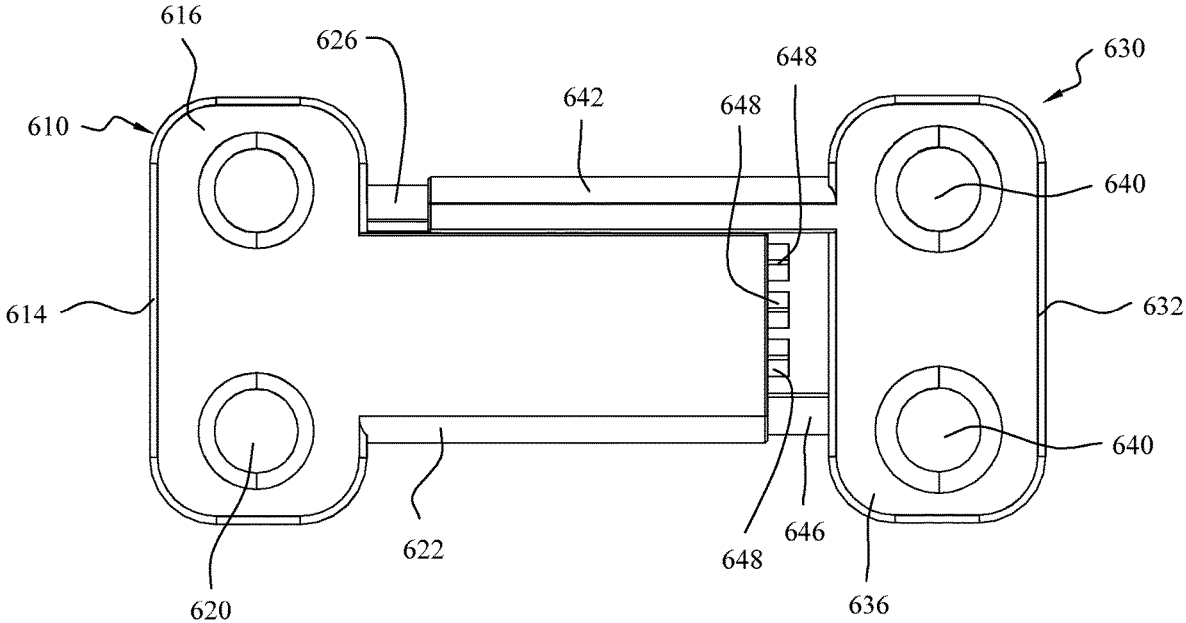
FIG. 43 is a top view of the plating device of FIG. 42, in accordance with an aspect of the present invention.
Figures 44, 45:
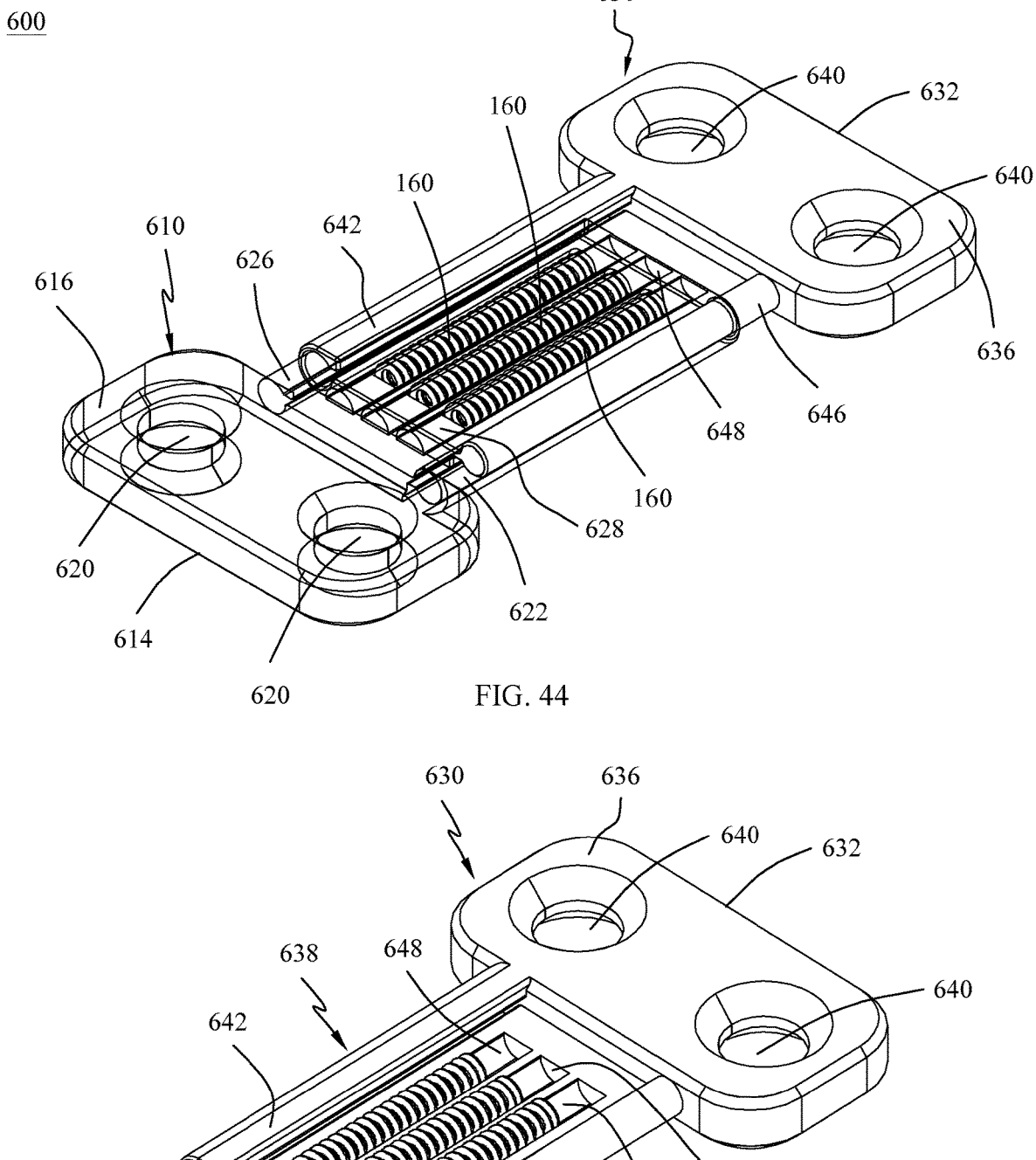
FIG. 44 is a perspective view of the plating device of FIG. 42 with a transparent first member, in accordance with an aspect of the present invention.
FIG. 45 is a perspective view of the plating device of FIG. 42 with the first member removed, in accordance with an aspect of the present invention.
Figure 46:
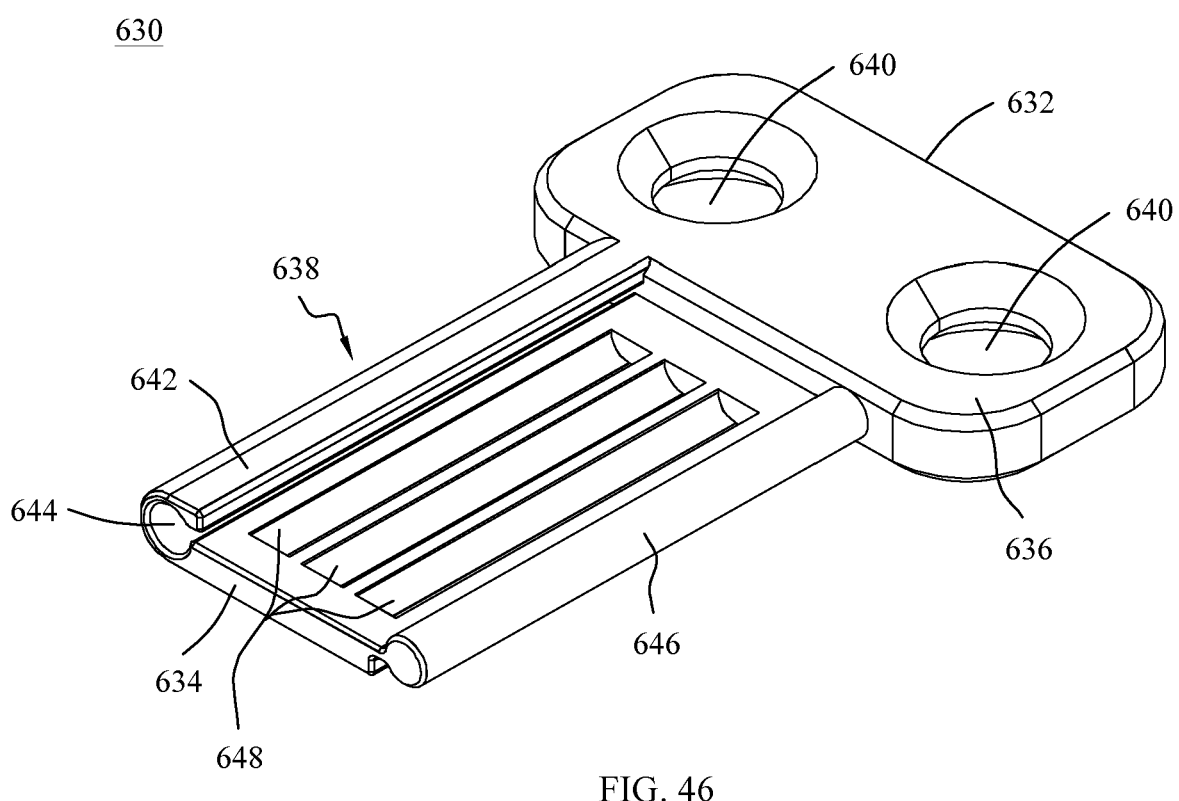
FIG. 46 is a perspective top view of the second member of the plating device of FIG. 42 with the springs removed, in accordance with an aspect of the present invention.
Figure 47:
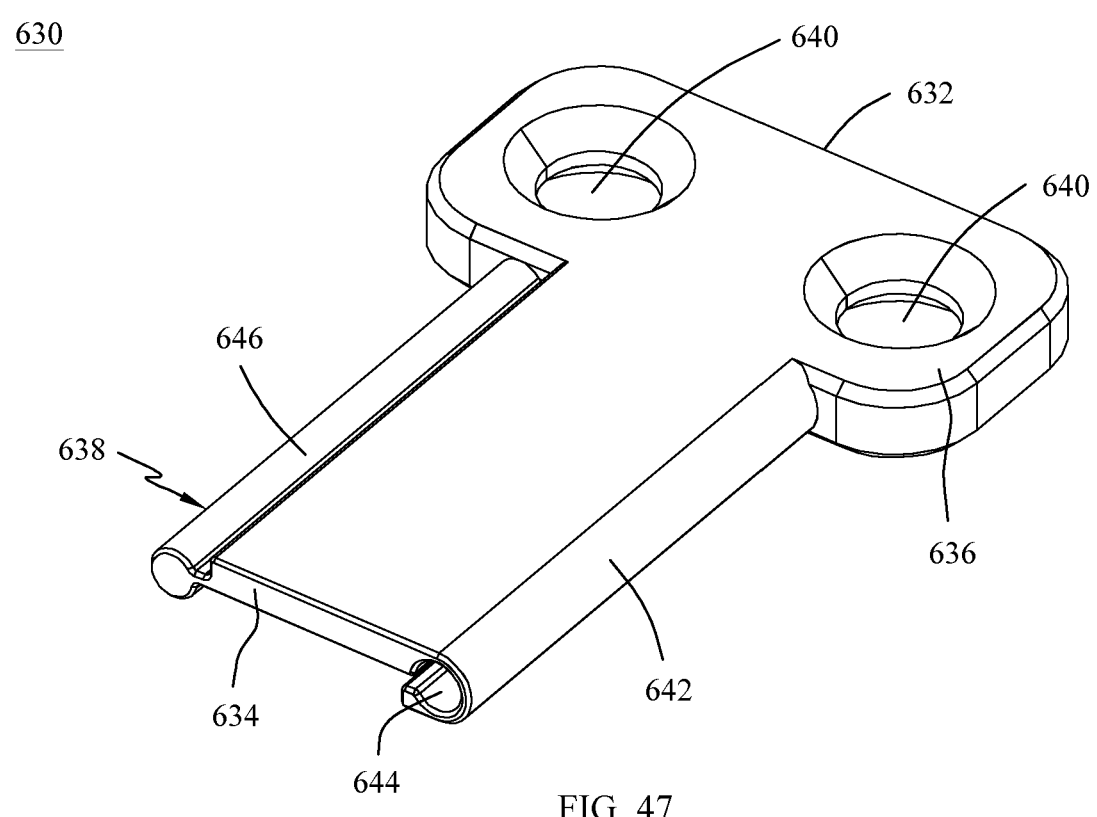
FIG. 47 is a perspective bottom view of the second member of the plating device of FIG. 42, in accordance with an aspect of the present invention.

Another alternative embodiment fixation or fusion device 500 is shown in FIGS. 32-33 and 41. The fixation device 500 may be, for example, a spinal rod for use with, for example, a pedicle screw system or other spinal correction system which uses rods. The device 500 may include a first member 510, a second member 530, at least one spring member 160, and a ring member 170. The second member 530 may be sized to fit into at least a portion of the first member 510 and the at least one spring member 160 and ring member 170 may be, for example, positioned between the first member 510 and second member 530. The at least one spring member 160 and ring member 170 may be of the types described in greater detail above with reference to device 100 and which will not be described again here in detail for brevity sake.

As shown in FIGS. 32-34 and 37-41, the first member 510 may include a first end 512 and a second end 514 opposite the first end 512. The first member 510 may also include a first coupling portion 524 and second portion 526. The first coupling portion 524 and second portion 526 may be, for example, generally cylindrical and the first coupling portion 524 may have, for example, a diameter that is larger than or the same size as the second portion 526. The second portion 526 may be, for example, a solid rod, while the first coupling portion 524 includes an opening 516. The opening 516 may extend into the coupling portion 524 of the first member 510 from the second end 514. The opening 516 may extend along a portion of the longitudinal axis of the first member 510 from the second end 514 toward the first end 512. For example, the opening 516 may extend only within the coupling portion 524 of the first member 510. The opening 516 may form an interior surface 518 within the first member 510. The interior surface 518 may include a groove 520 positioned near the second end 514 of the first member 510. The groove 520 may extend into the first member 510 from the interior surface 518 toward the exterior surface of the coupling portion 524 of the first member 510. The interior surface 518 of the first member 510 may have, for example, a relatively hexagonal or other polygonal shape starting after the groove 520 and extending toward the first end 512. The opening 516 may further include at least one channel or slot 522 inset into the interior surface 518 and extending from the groove 520 toward the first end 512 of the first member 510.

Figure 38:
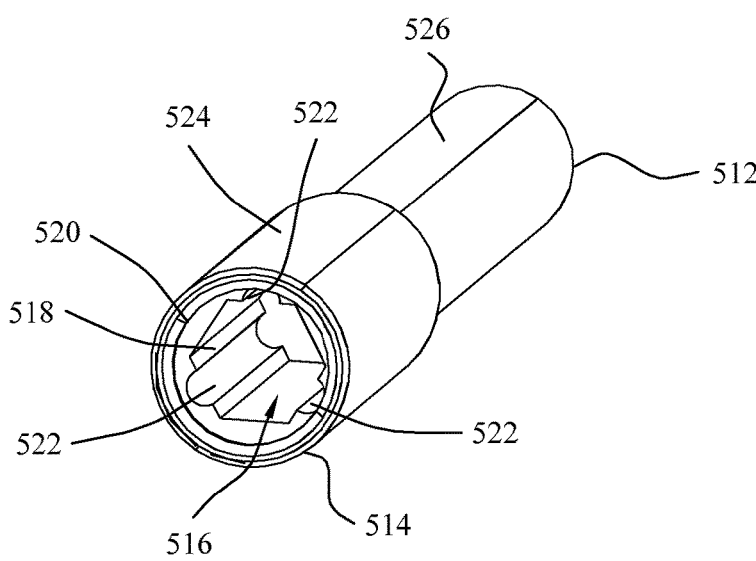
FIG. 38 is a perspective view of the first member of the fixation device of FIG. 32, in accordance with an aspect of the present invention.
Figure 39:
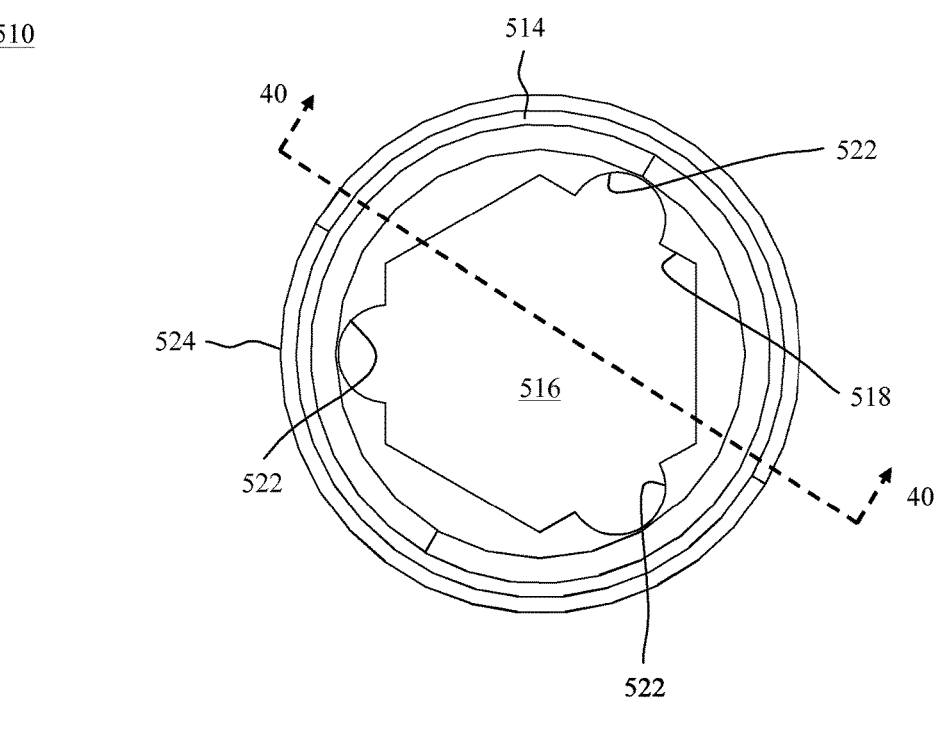
FIG. 39 is an end view of the first member of the fixation device of FIG. 32, in accordance with an aspect of the present invention.
Figure 40:
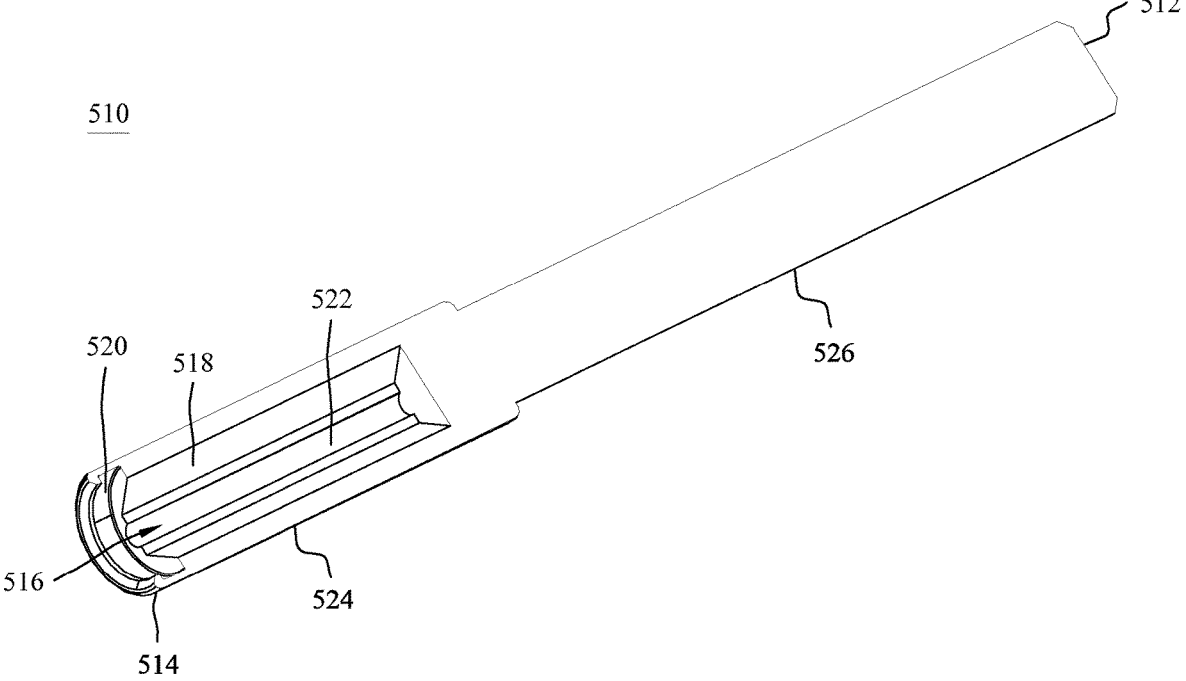
FIG. 40 is a cross sectional view of the first member taken along line 40-40 in FIG. 39, in accordance with an aspect of the present invention.

The first member 510 may be, for example, a female member. The device 500 may include, for example, any number of channels 522 and any number of spring members 160, such as one to twelve channels 522 and one to twelve spring members 160. In one embodiment, the at least one channel 522 and the at least one spring member 160 may be, for example, at least three channels 522 which may receive at least three spring members 160, as shown in FIGS. 33, 38 and 39. The at least three channels 522 may be positioned radially around the opening 516 as described in greater detail above with reference to channels 122 and opening 116, which will not be described again here for brevity sake.

Figure 35:
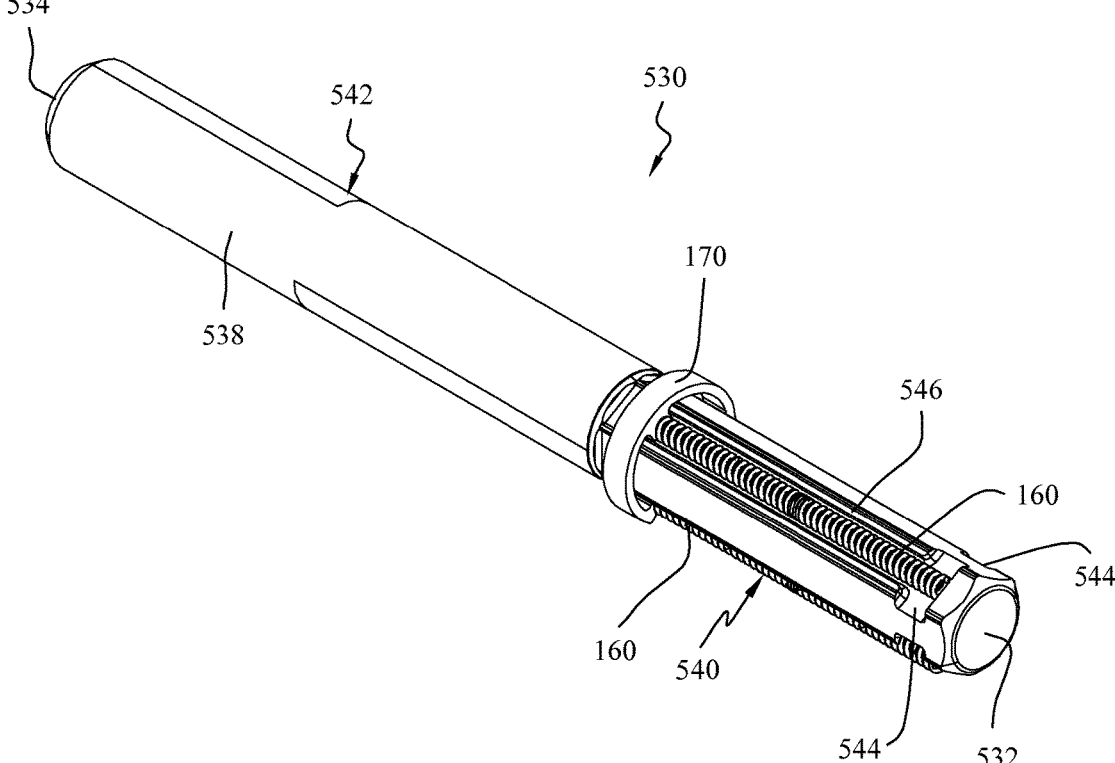
FIG. 35 is a perspective view of the fixation device of FIG. 32 with the first member removed, in accordance with an aspect of the present invention.
Figure 36:
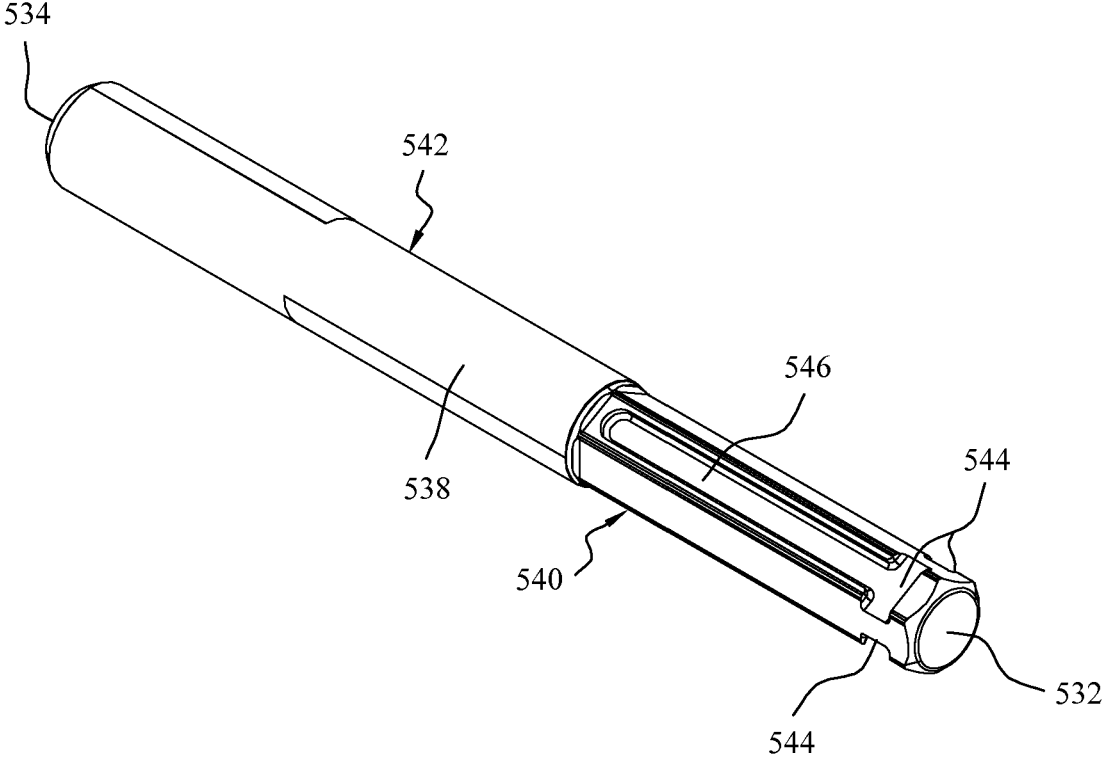
FIG. 36 is a perspective view of a second member of the fixation device of FIG. 32, in accordance with an aspect of the present invention.
Figure 37:
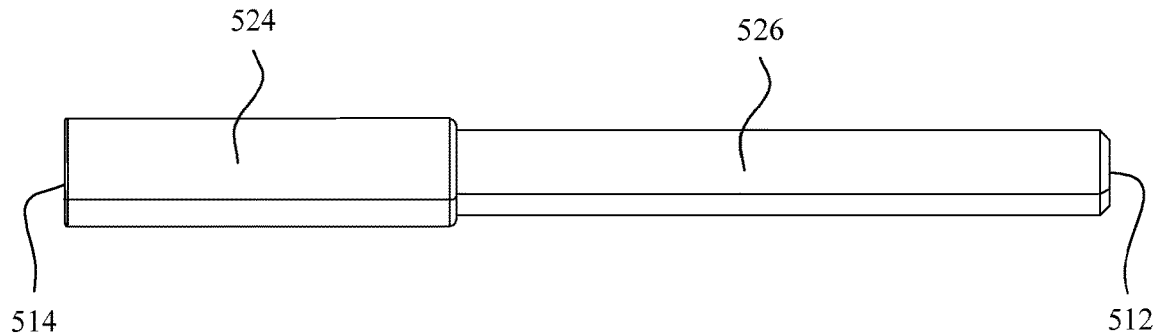
FIG. 37 is a side view of the first member of the fixation device of FIG. 32, in accordance with an aspect of the present invention.

The second member 530, as shown in FIGS. 32-36, may have a first end 532 and a second end 534 opposite the first end 532. The second member 530 may also have a coupling portion 540 positioned near the first end 532 for connecting the second member 530 to the first member 510 and a second portion 542 extending from the coupling portion 540 to the second end 534. The second portion 542 may have, for example, an exterior surface 538 with a generally cylindrical shape. The second portion 542 may have a diameter, for example, that is approximately the same as the diameter of the second portion 526. The width of the coupling portion 540 may be, for example, slightly smaller than the diameter of the second portion 542. The coupling portion 540, however, may have a relatively polygonal shape and may also include at least one depression or groove 544 near the first end 532 of the second member 530. The at least one depression 544 may be three depressions 544 positioned radially around the coupling portion 540. For example, if the coupling portion 540 has a polygonal shape with an even number of sides, the depressions 544 may be positioned on every other side of the polygonal shape. The at least one depression 544 is positioned around the coupling portion 540 such that the ring member 170 may be inserted onto the second member 530. The coupling portion 540 may also include at least one channel or slot 546 extending from the at least one depression 544 toward the second end 534 of the second member 530. The at least one channel 546 may be inset into the surface of the coupling portion 540 and may be sized to receive the at least one spring member 160. The fixation device 500 may also include, for example, any number of channels 546 and any number of spring members 160, such as one to twelve channels 546 and one to twelve spring members 160. In one embodiment, the at least one channel 546 and the at least one spring member 160 may be, for example, three channels 546 and at least three spring members 160, as shown in FIGS. 33 and 35. The channels 546 may be positioned radially around the coupling portion 540. It is also contemplated that in an alternative embodiment, the channel 536 may receive the at least one spring member 160. The coupling portion 540 may be sized to fit within the opening 516 of the first member 510. In addition, the shape of the coupling portion 540 may correspond to the shape of the opening 516 in the first member 510. The second member 530 may be, for example, a male member.

The at least one spring member 160 may be positioned between the at least one channel 522 of the first member 510 and the at least one channel 546 of the second member 530 when the second member 530 is inserted into the first member 510. The at least one spring member 160 is as described above with reference to FIGS. 4, 7-9, and 19, which will not be described again here for brevity sake.

As shown in FIGS. 33, 35, and 41, the ring member 170 may be of the type described above with reference to FIGS. 16-18, which will not be described again here for brevity sake. The ring member 170 may be inserted by sliding the at least one protrusion 174 into the at least one depression 544 of the second member 530 until the at least one protrusion 174 aligns with the at least one channel 546. Once at least one protrusion 174 is aligned with the at least one channel 546, the ring member 170 may be translated toward the distal end of the at least one channel 546. After the ring member 170 is positioned at the distal end of the at least one channel 546, the at least one spring 160 may be inserted into the channel 546 and the coupling portion 540 may be inserted into the opening 516 in the first member 510. When the coupling portion 540 is inserted into the opening 516, the at least one spring 160 slides into the at least one channel 522 of the first member 510. Alternatively, it is contemplated that one spring member 160 may be used and positioned in channel 536. If the spring member 160 is positioned in the channel 536, the ring member 170 will be configured to engage the spring member 160 inside the channel 536. The alternative embodiment of the spring member 160 and ring member 170 configuration is described in greater detail above with respect to bone fixation device 100 and will not be described again here for brevity. The coupling portion 540 may be inserted into the first member 510 until the ring member 170 engages the groove 520 in the first member 510 to secure the first member 510 and the second member 530 together.

The fixation device 500 may also include a locking mechanism (not shown) to prevent the first member 510 and the second member 530 from lengthening after compression is complete or from shortening after distraction is completed. The locking mechanism may be of the type described above in greater detail with respect to device 100 and which will not be described again here for brevity sake.

By way of specific example, the fixation device 500 is a spinal rod. The spinal rod may be a 5.5 mm rod which may be compressed between, for example, approximately 2 mm and 8 mm, or distracted or lengthened, for example, approximately 2 mm and 8 mm.

The method of assembling a bone fixation device as shown in FIG. 20 and described in greater detail above may also be used to assemble the fixation device 500.

The fixation device 500 may be used with a spinal stabilization system, for example, a pedicle screw system. The fixation device 500 may be, for example, spinal rods which may replace the rods currently used in spinal stabilization systems. In use a spinal stabilization procedure may be performed as currently done using pedicle screws. Once the pedicle screws are in place in the vertebra along the patient's spine, then the spinal rods 500 may be inserted into the pedicle screws in place of the currently used rods. The spinal rods 500 could be inserted with an insertion tool (not shown) which would hold the spinal rods 500 in the desired position, for example, either lengthened or shortened, while the first member 510 is secured to a first pedicle screw and a second member 530 is secured to a second pedicle screw.

Alternatively, the first member 510 of the spinal rods 500 could be secured to a first pedicle screw and then the second member 530 translated either proximally or distally to shorten or lengthen the rod 500. The spinal rods 500 would be lengthened or uncompressed if compression of the vertebra was desired. Alternatively, the spinal rods 500 would be shortened or compressed if distraction or lengthening of the vertebra was desired. Once the desired position of the second member 530 is achieved, the second member 530 is secured to the second pedicle screw.

The spinal rods 500 may be secured to the pedicle screws using a fastener, for example, a set screw. Once the spinal rods 500 are secured to the pedicle screws, the insertion tool may be removed or the surgeon may release the spinal rod 500 to allow for compression or distraction of the vertebra attached to the pedicle screws. When the spinal rods 500 are released an axial load is applied across the segment of the spine to be fused and a traction force is experienced between the two vertebral bodies.

As the axial load is applied, the device 500 begins to move back to a shortened compressed position or to a lengthened uncompressed position. The axial load of the rod 500 results from the at least one spring member 160 extending back to its uncompressed position which in turn exerts a force on the ring member 170 to move the second member 530 relative to the first member 510. As the spring member 160 expands to its uncompressed position, the first member 510 is either pushed or pulled with respect to the second end 534 of the second member 530 and the attached vertebra either distract or compress. Finally, the incisions in the patient may be closed.

It is contemplated that a resorbable member (not shown) may be used instead of the insertion tool to lengthen or shorten the device 500. When a resorbable member is used, after the device 500 is placed in the patient with a standard driver and/or holder, the patient's incision may be closed. The resorbable member will hold the device 500 in the desired extended or shortened position until the resorbable member starts to break down or erode. As the resorbable member breaks down over time from exposure to the in vivo environment inside of the patient, the at least one deformable member 160 may be released and exert force on the members 510, 530 to lengthen or shorten the device 500, as described in greater detail above. The resorbable member may be, for example, a cross pin, pawl, or the like which secures the device 500 in the desired extended or shortened position until the resorbable member erodes.

Figures 48, 49:
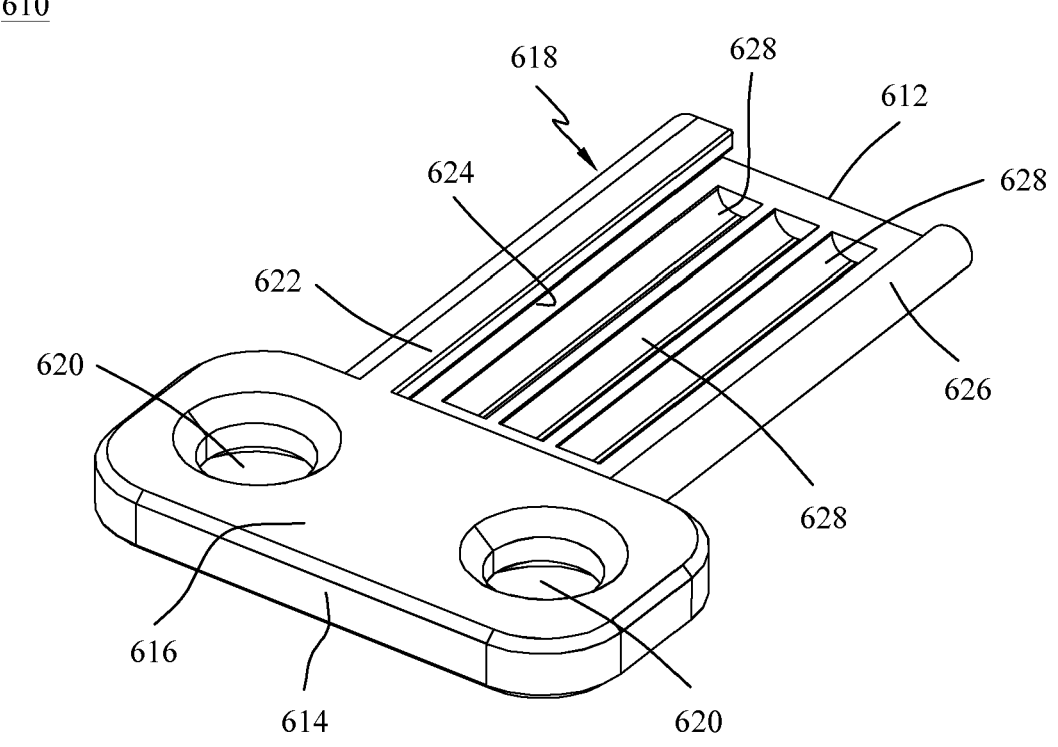
FIG. 48 is a perspective top view of the first member of the plating device of FIG. 42, in accordance with an aspect of the present invention.
FIG. 49 is a perspective side view of the first member of the plating device of FIG. 42, in accordance with an aspect of the present invention.
Figure 50:
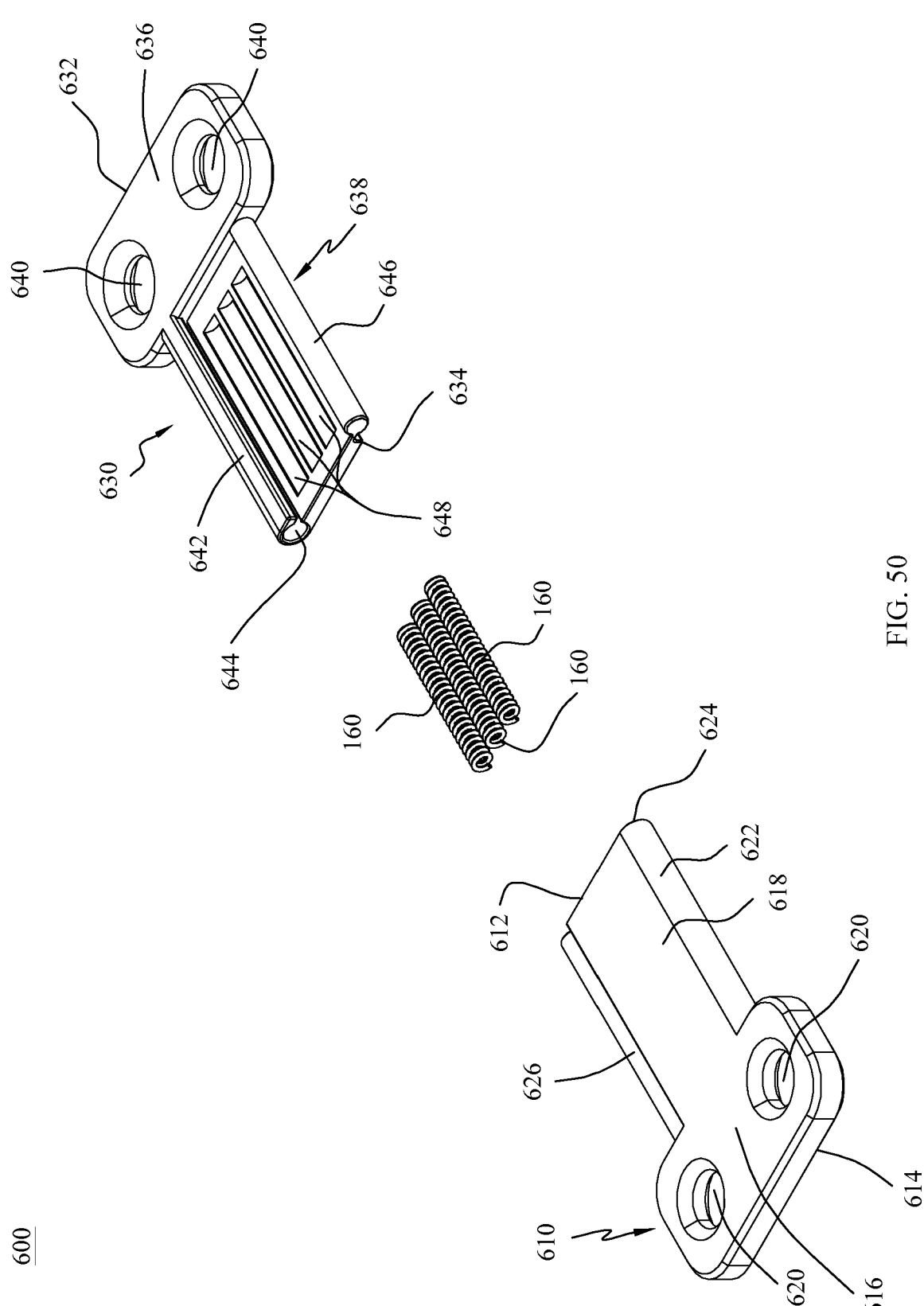
FIG. 50 is an exploded view of the plating device of FIG. 42, in accordance with an aspect of the present invention.
Figure 51:
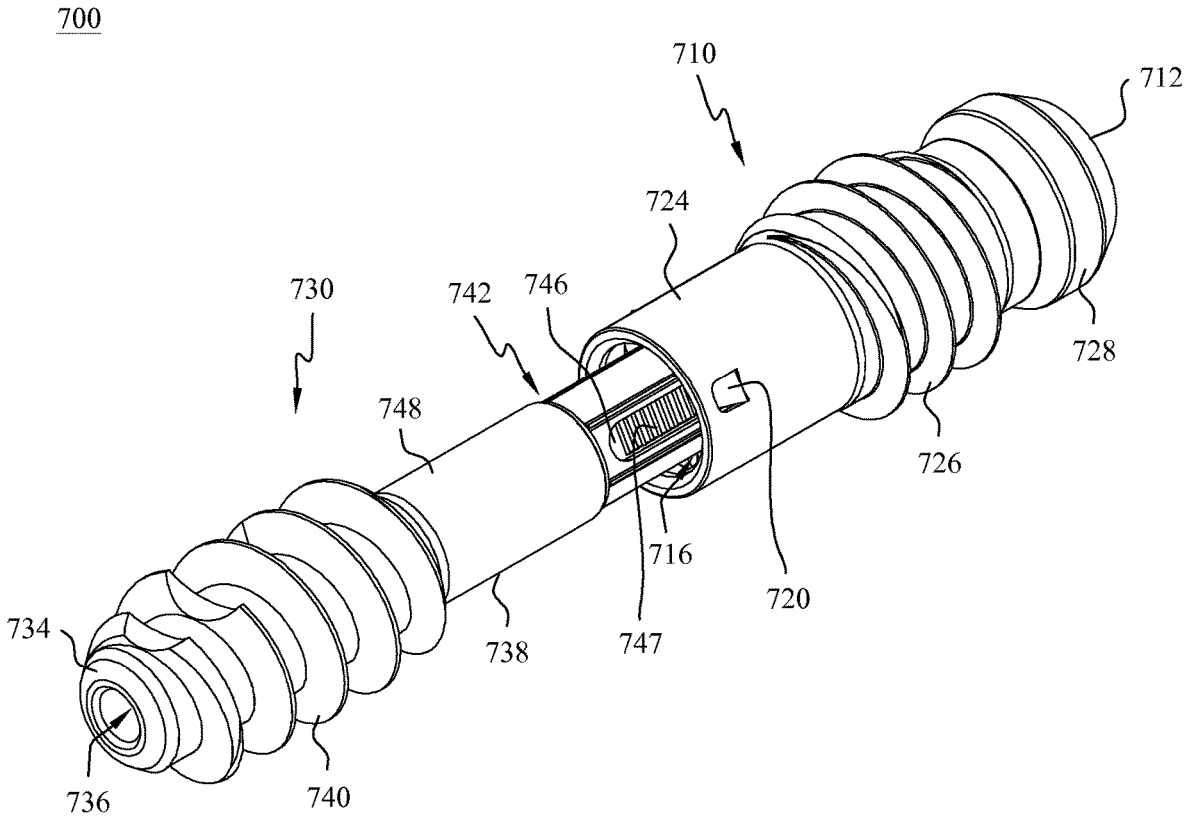
FIG. 51 is a perspective view of a bone fixation device, in accordance with an aspect of the present invention.

Referring now to FIGS. 42-50, a plating device 600 with a first member 610, a second member 630, and at least one spring 160 is shown. The at least one spring 160 is as described above with reference to device 100, which will not be described again here for brevity sake. The first member 610, as shown in FIGS. 42-44 and 48-50, may include a first end 612 and a second end 614 opposite the first end 612. The first member 610 may also include an attachment portion 616 at the second end 614 and a coupling portion 618 at the first end 612. The first member 610 may be, for example, generally T-shaped, although other shapes that provide a first portion for attachment to a bone or vertebra and a second portion for coupling to the second member 630 are also contemplated. The attachment portion 616 may be a plate section with at least one opening 620 for receiving a fastener, for example, a bone screw to secure the first member 610 to a bone or vertebra. In the depicted embodiment, the first member 610 includes two openings 620, although alternative numbers of openings 620 are also contemplated based on the size of the first member 610 and the bone or vertebra which the first member 610 will be secured to. As shown in FIG. 48, the coupling portion 618 may include a female coupling member 622 extending along a first side of the coupling portion 618 and a male coupling member 626 extending along a second side of the coupling portion 618 opposite the first side. The female coupling member 622 may include a channel 624 extending from the first end 612 to the attachment portion 616. The coupling portion 618 may also include at least one groove 628 extending from a position near the first end 612 to a position near the attachment portion 616. The at least one groove 628 may be sized to receive at least one spring member 160. The coupling portion 618 may include, for example, three grooves 628 for receiving three springs 160.

The second member 630, as shown in FIGS. 42-47 and 50, may include a first end 632 and a second end 634 opposite the first end 632. The first member 630 may also include an attachment portion 636 at the first end 632 and a coupling portion 638 at the second end 634. The second member 630 may be, for example, generally T-shaped, although other shapes that provide a first portion for attachment to a bone or vertebra and a second portion for coupling to the first member 610 are also contemplated. The attachment portion 636 may be a plate section with at least one opening 640 for receiving a fastener, for example, a bone screw to secure the second member 630 to a bone or vertebra. In the depicted embodiment, the second member 630 includes two openings 640, although alternative numbers of openings 640 are also contemplated based on the size of the second member 630 and the bone or vertebra to which the second member 630 will be secured. The coupling portion 638 may include a female coupling member 642 extending along a first side of the coupling portion 638 and a male coupling member 646 extending along a second side of the coupling portion 638 opposite the first side. The female coupling member 642 may include a channel 644 extending from the second end 634 to the attachment portion 636. The coupling portion 638 may also include at least one groove 648 extending from a position near the second end 634 to a position near the attachment portion 636. The at least one groove 648 may be sized to receive at least one spring member 160. The coupling portion 638 may include, for example, any number of grooves 648 and any number of springs 160, such as, one to twelve grooves 648 for receiving one to twelve springs 160. As shown in the depicted embodiments, the coupling portion 638 includes, for example, three grooves 648 for receiving three springs 160.

The plating device 600 may also include a locking mechanism or securement mechanism which engages the first member 610 and second member 630 to prevent the members 610, 630 for disengaging.

The plating device 600 may be assembled by aligning the female coupling member 622 of the coupling portion 618 with the male coupling member 646 of the coupling portion 638 and the male coupling member 626 of the coupling portion 618 with the female coupling member 642 of the coupling portion 638. Once aligned the male coupling members 626, 646 may be partially inserted into the female coupling members 642, 622, respectively. After the first member 610 is partially inserted into the second member 630, the at least one spring 160 may be inserted between the at least one grooves 628, 648. The at least one spring 160 may need to be compressed to enable insertion between the at least one grooves 628, 648. Next, the at least one spring 160 will uncompress and the device 600 will be positioned in a resting position until the device is implanted into a patient.

The plating device 600 may be secures to bones or vertebra in a desired position to promote fusion of the bones or vertebra. The plating device 600 may be inserted into a patient by first making an incision and preparing the bone or vertebra site where fusion is needed. Next, the plating device 600 may be, for example, lengthened to compress the at least one spring 160. The plating device 600 may be lengthened using an insertion tool or by the surgeon pulling the first and second members 610, 630 apart. Once the plating device 600 is lengthened it may be inserted over the bones or vertebra where fusion is desired. The first member 610 may be secured to a first bone or vertebra by inserting at least one fastener, for example, a bone screw, through the at least one opening 620. Then the second member 630 may be secured to a second bone or vertebra by inserting at least one fastener, for example, a bone screw, through the at least one opening 640. After the first and second members 610, 630 are secured to the first and second bones or vertebra, the plating device 600 may be released and the at least one spring 160 will return to its uncompressed position. As the at least one spring 160 returns to its uncompressed position, the spring 160 exerts a force on the first and second members 610, 630 in the grooves 628, 648 near the attachment portions 616, 636 and the plating device 600 shortens. The force applied to the first and second members 610, 630 by the spring 160 will apply axial loading across the bone or spinal segment being fused.

Alternatively, the plating device 600 may be inserted into the patient in a shortened position. When the shortened device 600 is released after being secured to the patient's bones or vertebra, the at least one spring 160 will return to its uncompressed position by exerting a force on the first and second members 610, 630 to push them apart and lengthen the device 600.

The insertion tool may be replaced by a resorbable member (not shown) to secure the device 600 in a desired extended or shortened position during insertion. When a resorbable member is used, after the plating device 600 is placed in the patient with, for example, a standard driver and/or holder, the patient's incision may be closed. The resorbable member will hold the plating device 600 in the desired extended or shortened position until the resorbable member starts to break down or erode. As the resorbable member breaks down over time from exposure to the in vivo environment inside of the patient, the at least one deformable member 160 may be released and exert force on the members 610, 630 to lengthen or shorten the device 600, as described in greater detail above. The resorbable member may be, for example, a cross pin, pawl, or the like which secures the device 600 in the desired extended or shortened position until the resorbable member erodes.

Referring now to FIGS. 51-58, another bone fixation device 700 is shown. The bone fixation device 700 includes a first member 710, a second member 730, and at least one spring or deformable member 160. The terms "spring member," "deformable member" and "elastic element" may be used interchangeably herein as they essentially refer to the same members. The bone fixation device 700 may also include at least one locking member 770. The second member 730 may be sized and shaped to fit into the first member 710 with, for example, at least one spring member 160 and the at least one locking member 770 positioned between the first member 710 and the second member 730. The bone fixation device 700 may be, for example, a screw, intramedullary rod, spinal rod, bone plate, and the like for joining together, compressing or pressing together at least two bones or pieces of bone or alternatively for expanding or distracting at least two bones or pieces of bone, as described in greater detail above and which will not be described again here for brevity sake.

Figure 56:
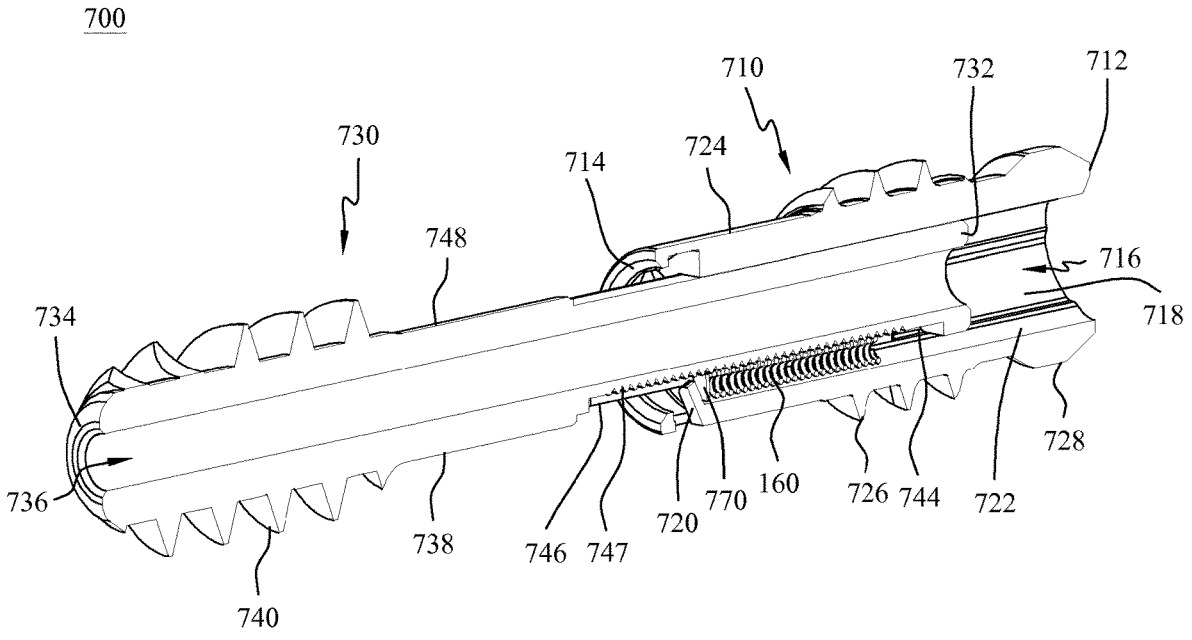
FIG. 56 is a cross-sectional view of the bone fixation device of FIG. 51 in a locked position taken along line 54-54 in FIG. 53, in accordance with an aspect of the present invention.
Figure 57:
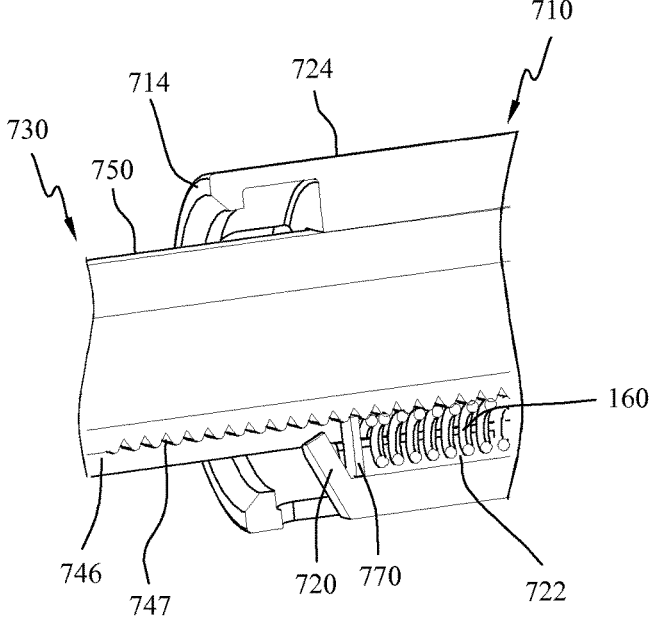
FIG. 57 is a magnified view of a portion of the bone fixation device of FIG. 56, in accordance with an aspect of the present invention.
Figure 58:
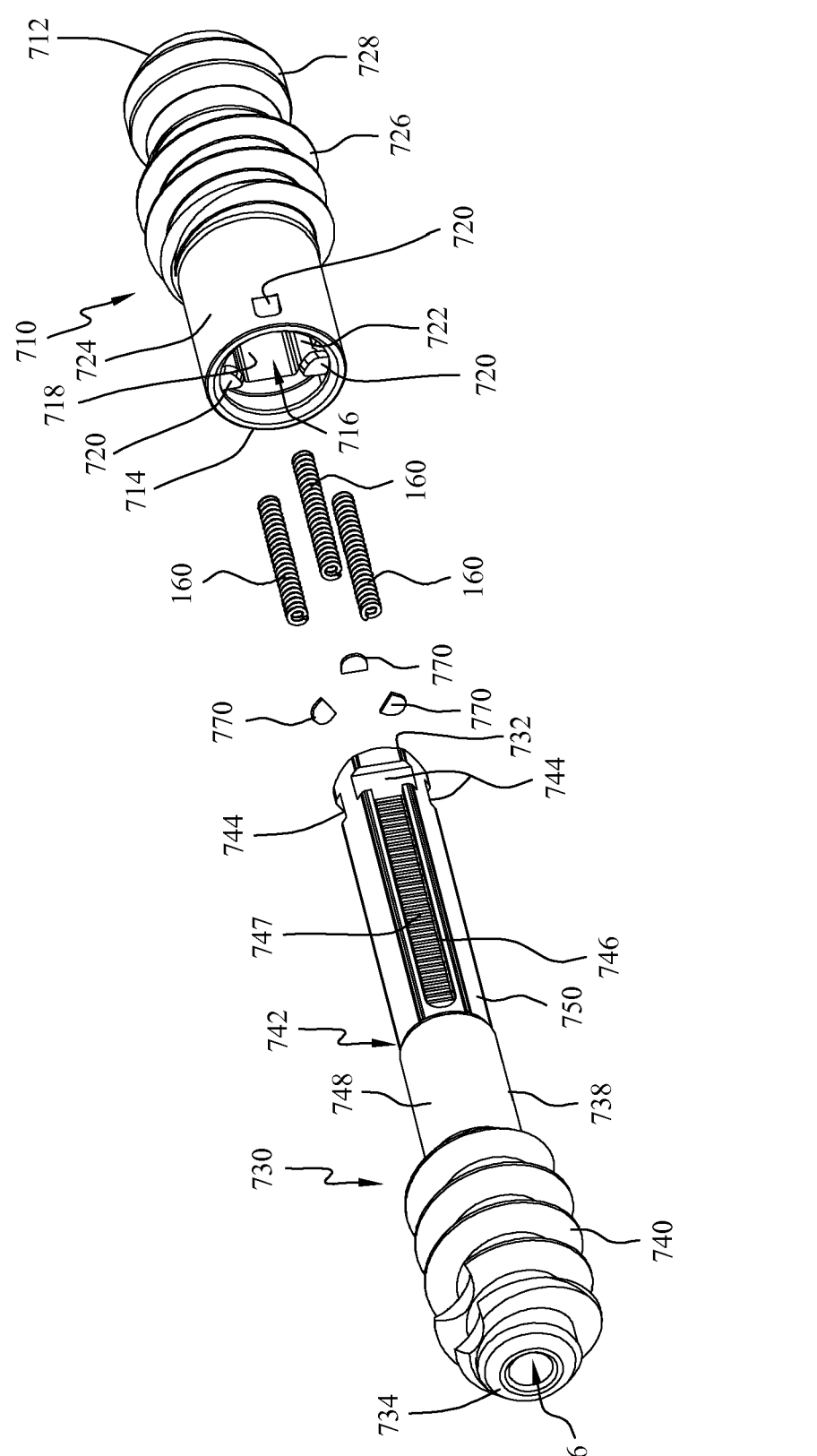
FIG. 58 is an exploded view of the bone fixation device of FIG. 51, in accordance with an aspect of the present invention.

The first member 710, as shown in FIGS. 51-58, may be, for example a female member. The first member 710 may include a first end 712 and a second end 714 opposite the first end 712. The terms "first end" and "proximal end" may be used interchangeably herein and the terms "second end" and "distal end" may be used interchangeably herein as they essentially refer to the same ends. The first member 710 may have an opening 716 extending from the first end 712 to the second end 714 along the longitudinal axis of the first member 710. The opening 716 may form an interior surface 718. The opening 716 of the first member 710 may also include at least one tab 720 extending inward from the exterior surface 724 of the first member 710 into the opening 716 near the second end 714. The opening of the interior surface 718 may have a cross-sectional geometry of, for example, a relatively hexagonal or polygonal shape extending from the first end 712 to the at least one tab 720. The opening 716 may also include at least one channel or slot 722 inset into the interior surface 718 and extending from the first end 712 toward the second end 714 and stopping when the channels 722 meet the at least one tab 720. The at least one tab 720 may be positioned at the bottom of the at least one channel 722. The at least one channel 722 is configured to or may receive the at least one spring member 160. The bone fixation device 700 may include, for example, one to twelve channels 722 and one to twelve spring members 160, as shown in FIG. 58, the device 700 may include three channels 722 and three corresponding spring members 160. The channels 722 may be positioned radially around the opening 716 to provide circumferential forces to facilitate equal compressive loads. For example, where the opening of the interior surface 718 is relatively hexagonally shaped, the channels 722 may be positioned on every other portion of the interior surface 718, for example, on the first, third, and fifth surfaces and the second, fourth, and sixth surfaces may be generally planar. The shape of the interior surface 718 may also be, for example, relatively octagonal or another polygonal shape with an even number of planar surfaces or sides.

With continued reference to FIGS. 51-58, the exterior surface 724 of the first member 710 may be, for example, generally cylindrical. The exterior surface 724 may include a threaded portion or threaded end 726 and a protrusion or extension 728. The protrusion 728 may extend away from the exterior surface 724 near the first end 712 to form an engagement portion for coupling to an insertion tool or resorbable member for insertion into a patient. The protrusion 728 may be of the type described above with reference to protrusion 128 which will not be described in detail again here for brevity sake. The threaded portion 726 may be positioned, for example, toward the middle of the first member 710 between the protrusion 728 and the second end 714 of the first member 710. The threaded portion 726 may extend only along a portion of the exterior surface 724 from the protrusion 728 to the second end 714, or alternatively, the threaded portion 726 may extend from the protrusion 728 to the second end 714 of the first member 710.

The second member 730 may have a first end 732 and a second end 734 opposite the first end 732, as shown in FIG. 58. The second member 730 may be, for example, a male member. The second member 730 may include a cannulation or channel 736 extending from the first end 732 to the second end 734 through the generally central portion of the second member 730 along the longitudinal axis of the second member 730. The cannulation 736 may be sized to receive a guide wire, guide pin, or the like to facilitate placement in vivo. It is also contemplated that the channel 736 may receive, for example, the at least one spring member 160. The second member 730 may also have an exterior surface 738. The exterior surface 738 may include a threaded region or threaded end 740 positioned near the second end 734 and a shaft region 742 extending from the threaded region 740 to the first end 732. The threaded region 740 of the second member 130 may have, for example, a smaller diameter than the threaded portion 726 of the first member 710. Alternatively, the threaded region 740 of the second member 730 may have the same diameter as the threaded portion 726 of the first member 710. In addition, the threaded ends 726, 740 may have, for example, the same threads or different threads. The threads may be selected based on the type and condition of the bone they are being inserted into to ensure the threaded ends 726, 740 grip onto the bones or bone pieces while translation of the bones is occurring.

Figure 52:
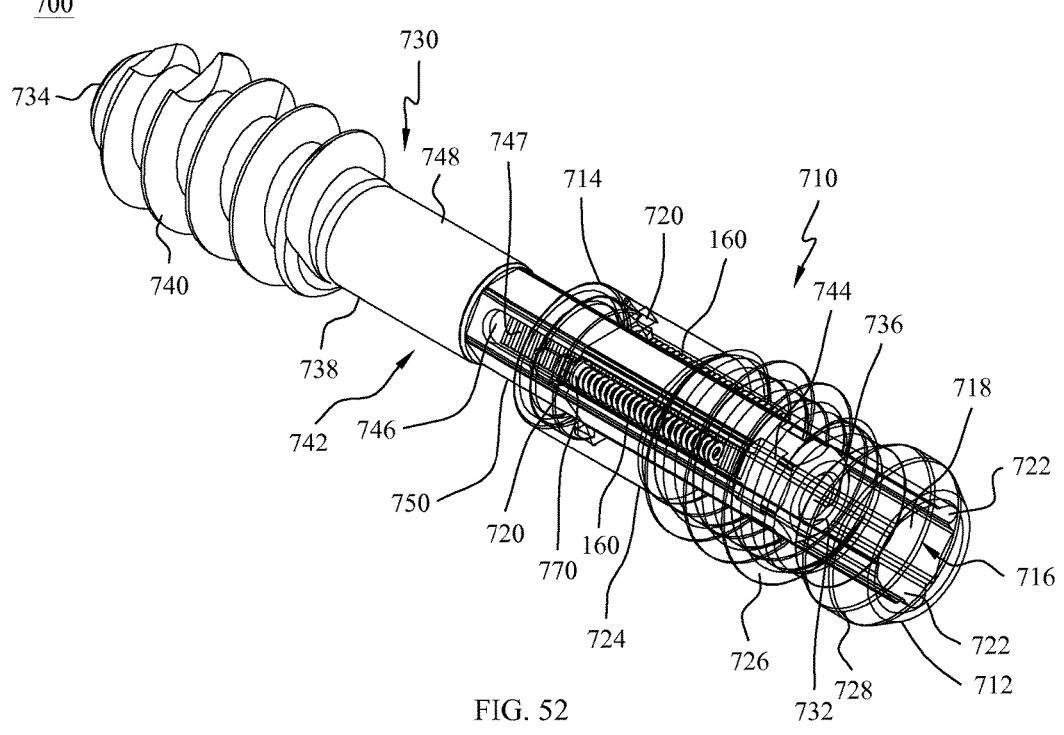
FIG. 52 is a perspective view of the bone fixation device of FIG. 51 with a transparent first member, in accordance with an aspect of the present invention.
Figure 53:
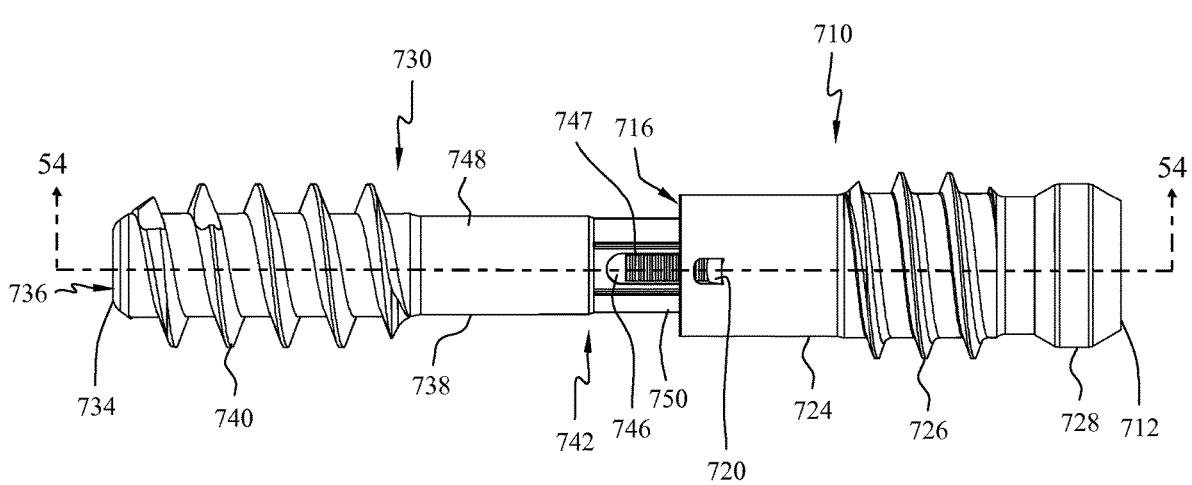
FIG. 53 is a side view of the bone fixation device of FIG. 51, in accordance with an aspect of the present invention.

With continued reference to FIG. 58, the shaft portion 742 of the second member 730 may include, for example, a first portion 748 with a generally cylindrical shape and a second portion 750, having a cross-sectional hexagonal or polygonal shape. The second portion 750 may extend from the first end 732 of the second member 730 toward the threaded region 740 and the first portion 748 may be positioned between the threaded region 740 and the second portion 750. The second portion 750 may also include at least one depression or groove 744 near the first end 732 of the second member 730 for insertion of the at least one tab 720. The at least one depression 744 may include, for example, one to twelve depressions 744, in the depicted embodiment three depressions 744 are shown, positioned radially around the exterior surface 738 of the shaft region 742. Where the second portion 750 of the shaft region 742 has, for example, a polygonal shape with an even number of sides, such as, a hexagon, octagon, or the like, the depressions 744 may be positioned on every other side of the polygonal shape. The depressions 744 may be positioned and be configured to enable insertion of the at least one tab 720 of the first member 710. The second portion 750 may also include at least one channel or slot 746 extending from the at least one depression 744 toward the first portion 748. The at least one channel 746 may be inset into the exterior surface 738. The at least one channel 746 may include a plurality of teeth or grooves 747 positioned relatively perpendicular to the longitudinal axis of the channel 746. The grooves 747 may be sized to receive the at least one locking member 770, as described in greater detail below. The at least one channel 746 may at least partially receive the at least one spring member 160, as shown in FIG. 52.

The second member 730 may include, for example, any number of channels 746 and any number of spring members 160, such as, one to twelve channels 746 and one to twelve spring members 160. In the illustrated embodiment, the bone fixation device includes three channels 746 and three spring members 160. The at least one channel 746 may be positioned radially around the second portion 750 of the exterior surface 738. The exterior surface 738 of the second portion 750 of the shaft region 742 may have a shape corresponding to the shape of the opening 716 in the first member 710. For example, where the exterior surface 738 of the second portion 750 of the shaft region 742 has a relatively hexagonal cross-sectional shape, the channels 746 may be positioned on every other portion of the exterior surface 738, for example, on the first, third and fifth surfaces and the second, fourth and sixth surfaces may be generally planar. The cross-sectional shape of the exterior surface 738 may also be, for example, relatively octagonal or another polygonal shape with any number of sides. The exterior surface 738 may have any shape with an even or odd number of sides and a spring channel 746 may be located in one or more of the sides of the exterior surface 738. At least one spring member 160 will be positioned in the at least one spring channel 746.

The bone fixation device 700 may have, for example, the at least one spring member 160 that is positioned between the at least one channel 722 of the first member 710 and the at least one channel 746 of the second member 730 when the second member 730 is inserted into the first member 710. In the depicted embodiment, at least three spring members 160 are positioned between the three channels 722 and the three channels 746. The at least three spring members 160 may be, for example, three single springs or three sets of at least two springs. The spring members 160 may be, for example, spiral springs or straight springs as described in greater detail above with respect to bone fixation device 100.

Figure 54:
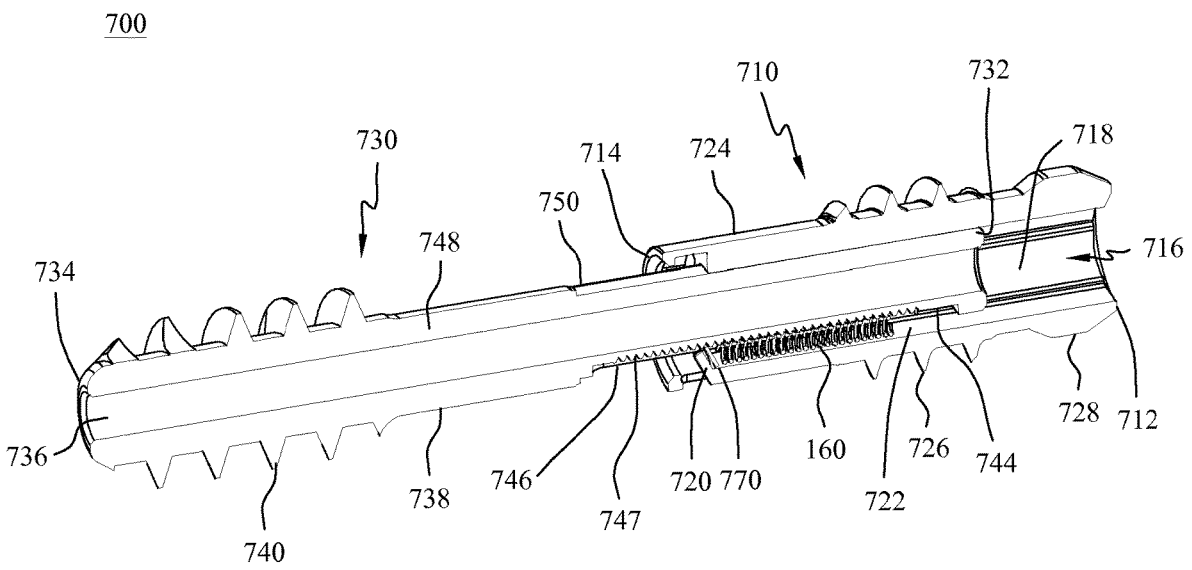
FIG. 54 is a cross-sectional view of the bone fixation device of FIG. 51 in an unlocked position taken along line 54-54 in FIG. 53, in accordance with an aspect of the present invention.
Figure 55:
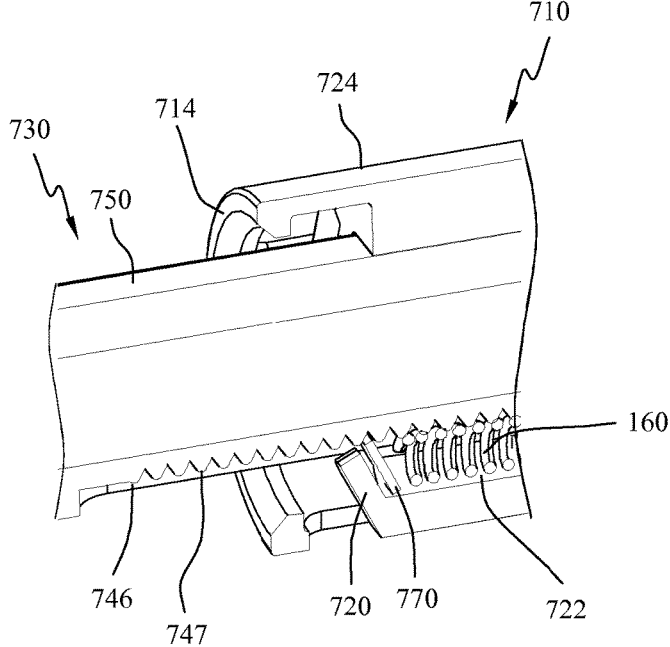
FIG. 55 is a magnified view of a portion of the bone fixation device of FIG. 54, in accordance with an aspect of the present invention.

The at least one locking member 770, as shown in FIGS. 54-58, may be sized and shaped to be positioned between the channel 722 of the first member 710 and the channel 746 of the second member 730. The at least one locking member 770 may also be positioned proximal to the at least one tab 720 of the first member 710 and distal to the at least one spring member 160. The at least one locking member 770 may be, for example, a ratcheting locking member 770 which allows the first and second members 710, 730 to be moved in a first direction with respect to each other, as shown in FIGS. 54-55, but locks the first and second members 710, 730 together and prevents them from moving in a second opposite direction, as shown in FIGS. 56-57. The at least one locking member 770 engages the grooves 747 in the at least one channel 746 of the second member 730 at a first end and contacts the at least one channel 722 of the first member 710 at a second end to secure the first and second members 710, 730 in a desired position. The at least one locking member 770 may be, for example, rotatably connected to the at least one channel 722 of the first member 710. The at least one locking member 770 may be, for example, rounded on a first end and planar on a second opposite end. It is also contemplated that the locking member 770 may be, for example, a conical shaped spring washer or another alternative shape which allows for the locking members 770 to move in a first direction and lock in a second direction. The locking members 770 may, for example, prevent the first member 710 and second member 730 from lengthening after compression of the bone fixation device 700 is complete.

The at least one tab 720 and at least one locking member 770 of the bone fixation device 700 may be, for example, used in place of the ring member 170 in the fixation device 400 and the fixation device 500 as described above with respect to bone fixation device 700.

By way of specific example, the bone fixation device 700 may be a screw. The screw 700 may be, for example, a 5.5 mm screw with the opening 716 of the first member 710 having a width at the first end 712 of approximately 2.5 mm to 3.5 mm and a diameter at the second end 714 of approximately 4 mm to 5 mm and the shaft region 742 of the second member 730 having, for example, an outer diameter of approximately 2.5 mm to 3.5 mm.

A method of assembling the bone fixation device 700 may include, for example, obtaining a first member, a second member, at least one spring member, and at least one locking member. The method may also include, for example, inserting a portion of the second member into the first member. The method may further include, for example, positioning the at least one spring member between the first member and the second member and positioning the at least one locking member between the first member and the second member distal to the at least one spring member. Finally, the method may include sliding the second member into the first member to a first position.

The methods of using the bone fixation device 700 is similar to as described above with reference to the methods of using the bone fixation device 100 and which will not be described again here for brevity sake.

The present invention provides in one aspect, a bone fixation device including a first member, a second member shaped to engage the first member, at least one spring member, and a ring member shaped to engage the first member and the second member.

In some embodiments the bone fixation device includes the first member with an opening extending from a first end to a second end defining an interior surface and the interior surface includes a groove near the second end of the first member and at least one channel extending form the first end to the groove. The first member also including a threaded portion extending out from an exterior surface of the first member and a protrusion near the first end extending away from the exterior surface.

In some embodiments the bone fixation device includes the second member with a cannulation extending from a first end to a second end and an exterior surface. The exterior surface including a shaft region near the first end and a threaded region near the second end. The shaft region with at least one depression near the first end and at least one channel extending from the first end toward the second end along a section of the shaft region.

In some embodiments the bone fixation device includes the at least one deformable member positioned between the first member and the second member.

In some embodiments the bone fixation device includes the ring member including a body portion removably coupled to the groove on an exterior surface and at least one protrusion extending away from an interior surface of the body portion of the ring member, the at least one protrusion shaped to engage the at least one channel of the shaft region of the second member.

The present invention also provides in one aspect, a bone fusion device including a female member with a proximal end and a distal end, a male member with a proximal end and a distal end, at least three elastic elements each engaging the at least three slots of the female member and the at least three slots of the male member, and a fastener. The female member including a channel extending from the proximal end to the distal end and having an interior surface, an end having at least one cylindrical thread, and an extension near the proximal end. The interior surface having a groove near the distal end of the female member and at least three slots extending from the proximal end to the groove and inset into the interior surface. The male member including a hole extending from the proximal end to the distal end and an exterior surface. The exterior surface including a shaft region near the proximal end and shaped to engage the opening of the female member and an end comprising a series of threads. The shaft region including at least one groove near the proximal end and at least three slots extending from the proximal end toward the distal end along a section of the shaft region. The fastener including a body with an exterior surface that engages the groove of the female member and at least three tabs extending away from an interior surface of the body of the fastener, the at least three tabs are shaped to engage the at least three slots of the shaft region of the male member.

In some embodiments the bone fusion device includes the end of the female member with a first diameter and the end of the male member with a second diameter, the first diameter is larger than the second diameter.

The present invention also provides in another aspect, a bone plating device including a first member with a male coupling member and a female coupling member, a second member with a male coupling member and a female coupling member, wherein the male coupling member of the first member engages the female coupling member of the second member and the female coupling member of the first member engages the male coupling member of the second member, and at least one deformable member positioned between the first member and the second member.

The present invention provides in another aspect, a method for assembling a bone fixation device, the method may include obtaining a first member, a second member, a ring member, and at least one spring member. The method may also include coupling the ring member to the second member. The method may further include positioning the at least one spring member inside at least the first member and between the ring member and a first end of the first member. Finally, the method may include sliding the second member into the first member until the ring member is inserted into an opening at a second end of the first member.

In some embodiments the method for assembling the bone fixation device may also include inserting a portion of a first end of the second member into the second end of the first member prior to positioning the at least one deformable member.

The present invention provides in yet another aspect, a method of inserting a bone fixation device, the method may include obtaining the bone fixation device. The bone fixation device including a first member, a second member engaging the first member, at least one elastic element positioned inside at least the first member, and a ring member engaging the first member and the second member. The method may also include obtaining an insertion tool and inserting a portion of the first member into an opening in the insertion tool. The method may further include moving the second member as the insertion tool engages the first member. Finally, the method may include inserting the bone fixation device into at least one bone of a patient and removing the insertion tool from the bone fixation device.

In some embodiments, the method of inserting the bone fixation device may also include inserting a guide wire into the at least one bone of the patient, using the guide wire to insert the bone fixation device into the at least one bone of the patient, and imaging the at least one bone of the patient to check the position of the inserted bone fixation device The present invention provides in a further aspect, a bone fusion device including a female member with a proximal end and a distal end, a male member with a proximal end and a distal end, and at least one elastic element positioned between the female member and the male member.

In some embodiments, the bone fusion device may also include the female member with an opening extending along at least a portion of the proximal end to the distal end and having an interior surface. The interior surface may include at least one slot extending from a position near the distal end toward the proximal end and inset into the interior surface.

In some embodiments, the bone fusion device may also include the male member with an exterior surface including a shaft region near the proximal end and shaped to engage the opening of the female member. The shaft region including at least one groove near the proximal end and at least one slot extending from the proximal end toward the distal end along a section of the shaft region.

In some embodiments, the bone fusion device may also include the at least one elastic element positioned within at least a portion of the at least one slot of the female member and within at least a portion of the at least one slot of the male member.

In some embodiments, the bone fusion device may also include the distal end of the female member with a first diameter and the proximal end of the male member with a second diameter, wherein the first diameter is larger than the second diameter.

In some embodiments, the bone fusion device may also include the at least one elastic element comprises three elastic elements, the at least one slot of the female member comprises three slots, and the at least one slot of the male member comprises three slots.

In some embodiments, the bone fusion device may also include the female member further including at least one tab coupled to the interior surface of the female member and extending into the opening.

In some embodiments, the bone fusion device may also include the at least one tab positioned at the end of the at least one slot of the female member and aligned with the at least one slot of the male member.

In some embodiments, the bone fusion device may also include at least one slot of the male member including a plurality of grooves positioned perpendicular to a longitudinal axis of the male member.

In some embodiments, the bone fusion device may also include a locking member coupled to the female member at a first end and shaped to engage the plurality of grooves in the at least one slot of the male member at a second end.

In some embodiments, the bone fusion device may also include a fastener with a body with an exterior surface that engages a groove in the interior surface of the female member and at least one tab extending away from an interior surface of the body of the fastener. The at least one tab shaped to engage the at least one slot of the shaft region of the male member.

The present invention provides in yet another aspect, a bone plating device including a first member, a second member shaped to engage the first member, and at least one deformable member positioned between the first member and the second member.

In some embodiments, the bone plating device may also include the first member with a coupling portion at a first end of the first member and an attachment portion at a second end of the first member.

In some embodiments, the bone plating device may also include the coupling portion of the first member may include a male coupling member extending along a first side of the coupling portion, a female coupling member extending along a second side of the coupling portion, wherein the first side is positioned opposite the second side, and at least one groove extending from a position near a first end of the first member to a position near the attachment portion of the first member.

In some embodiments, the bone plating device may also include the second member with an attachment portion at a first end of the second member and a coupling portion at a second end of the second member.

In some embodiments, the bone plating device may also include the coupling portion of the second member with a female coupling member extending along a first side of the coupling portion, a male coupling member extending along a second side of the coupling portion, wherein the first side is positioned opposite the second side, and at least one groove extending from a position near a second end of the second member to a position near the attachment portion of the second member.

In some embodiments, the bone plating device may also include the male coupling member of the first member engaging the female coupling member of the second member and the female coupling member of the first member engaging the male coupling member of the second member.

In some embodiments, the bone plating device may also include the at least one deformable member is positioned within at least a portion of the at least one groove of the first member and within at least a portion of the at least one groove of the second member.

The present invention provides in yet another aspect, a method of assembling a bone fixation device including obtaining a first member, a second member, and at least one deformable member. The method may also include positioning the at least one deformable member inside at least the first member and sliding the second member into the first member to couple the first member to the second member.

In some embodiments, the method of assembling a bone fixation device may also include inserting a portion of a first end of the second member into the second end of the first member prior to positioning the at least one deformable member.

The present invention provides in another aspect, a method of inserting a bone fixation device including obtaining the bone fixation device. The bone fixation device including a first member, a second member engaging the first member, and at least one elastic element positioned inside at least the first member. The method may also include obtaining an insertion tool and inserting a portion of the first member into an opening in the insertion tool. The method may further include moving the second member as the insertion tool engages the first member and inserting the bone fixation device into at least one bone of a patient. Finally, the method may include removing the insertion tool from the bone fixation device.

In some embodiments, the method of inserting a bone fixation device may also include inserting a guide wire into the at least one bone of the patient. The method may further include using the guide wire to insert the bone fixation device into the at least one bone of the patient and imaging the at least one bone of the patient to check the position of the inserted bone fixation device.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

Although the example embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. A method of treating a bone fracture comprising:
   providing a device having a first member, a second member and a deformable member, the deformable member being positioned between the first and the second member;
   inserting the device between two bones at a bone fracture site in a manner to move the deformable member from an undeformed state to a deformed state;
   moving the deformable member to a deformed length corresponding to a specific bone correction length, wherein the deformed length is selected from a range of discrete deformed states that are each associated with a respective distance between the first and second member for a determined bone correction;
   releasing the deformable member so that the deformable member moves from the deformed state to the undeformed state and thereby moves the first member and the second member towards one another, and, further, so that the device shortens in length.

2. The method of claim 1, wherein the first member comprises an opening extending from a second end towards a first end along at least a portion of the first member that defines an interior surface in the first member.

3. The method of claim 2, wherein the interior surface comprises at least one channel extending along at least a portion of a length of the first member.

4. The method of claim 3, wherein the second member comprises an exterior surface having a shaft region near a first end of the second member, wherein the shaft region comprises:

at least one depression near the first end of the second member; and at least one channel extending from the first end of the second member towards a second end of the second member.

5. The method of claim 4, wherein the exterior surface of the second member further comprises a threaded region near the second end of the second member.

6. The method of claim 4, wherein the second member further comprises a cannulation extending from a first end to a second end.

7. The method of claim 1, further comprising a locking member engaging the first member at a first end and the second member at a second end.

8. The method of claim 1, wherein the first member comprises: a coupling portion at a first end of the first member; and an attachment portion at a second end of the first member.

9. A method to facilitate bone fracture healing comprising:

providing a device having a first member, a second member and an actuator, the actuator operatively connecting the first and second member;

inserting the device between two bones at a bone fracture site in a manner to move the actuator from a resting state to an energy storing state;

moving the actuator to an energy storing state length corresponding to a specific bone correction length, wherein the energy storing state length is selected from a range of discrete energy storing states that are each associated with a respective distance between the first and second member for a determined bone correction; and releasing the actuator so that the actuator moves from the energy storing state to the resting state and thereby moves the first member and the second member towards one another, and, further, so that the device shortens in length.

10. A method according to claim 9, wherein said actuator is at least one spring.

11. A method according to claim 10, wherein said actuator is at least one coil spring.

12. A method according to claim 9, wherein one of said first and second member includes a surface for receiving an insertion tool.

13. A method according to claim 12, wherein said surface provides a leverage surface for said insertion tool to compress said actuator.

14. A method according to claim 9, wherein said first and second members each have screw threads.

15. A method of urging at least two bones together for healing comprising:

providing a device having an elastic member connecting a proximal bone engagement member and a distal bone engagement member;

inserting the device between two bones at a bone fracture site in a manner to move the elastic member from a non-biased state to a biased state;

moving the elastic member to biased state length corresponding to a specific bone correction length, wherein the biased state length is selected from a range of discrete biased states that are each associated with a respective distance between the proximal and distal bone engagement members for a determined bone correction;

releasing the elastic member so that the elastic member moves from the biased state to the non-biased state and thereby moves the proximal and distal bone engagement members towards one another, and, further, so that the device shortens in length.

16. A method according to claim 15, wherein said elastic member is at least one spring.

17. A method according to claim 16, wherein said elastic member is at least one coil spring.

18. A method according to claim 15, wherein one of said proximal and distal bone engagement member includes a surface for receiving an insertion tool.

19. A method according to claim 18, wherein said surface provides a leverage surface for said insertion tool to compress said elastic member.

20. A method according to claim 15, wherein said proximal and distal bone engagement members each have screw threads.

* * * * *